(12) United States Patent
Nakai et al.

(10) Patent No.: US 7,713,998 B2
(45) Date of Patent: May 11, 2010

(54) NITROGENOUS HETEROCYCLIC COMPOUND AND PHARMACEUTICAL USE THEREOF

(75) Inventors: Hisao Nakai, Oasaka (JP); Shingo Yamamoto, Osaka (JP); Shingo Nakatani, Osaka (JP); Tomomi Hirosaki, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 11/719,058

(22) PCT Filed: Nov. 9, 2005

(86) PCT No.: PCT/JP2005/020555

§ 371 (c)(1), (2), (4) Date: May 10, 2007

(87) PCT Pub. No.: WO2006/051826

PCT Pub. Date: May 18, 2006

(65) Prior Publication Data

US 2007/0265308 A1    Nov. 15, 2007

(30) Foreign Application Priority Data

Nov. 10, 2004  (JP)  ............................ 2004-326770
Apr. 28, 2005  (JP)  ............................ 2005-130838

(51) Int. Cl.
*A61K 31/445* (2006.01)
*C07D 211/68* (2006.01)

(52) U.S. Cl. ..................................... 514/318; 546/194

(58) Field of Classification Search ............... 546/194; 514/318
See application file for complete search history.

(56) References Cited

FOREIGN PATENT DOCUMENTS

| | | |
|---|---|---|
| EP | 1 402 900 A1 | 3/2004 |
| JP | 2001-114690 A | 4/2001 |
| WO | 99-01449 A1 | 1/1999 |
| WO | 00-64894 A1 | 11/2000 |
| WO | 01/30778 A1 | 5/2001 |
| WO | 02/072576 A1 | 9/2002 |
| WO | 03-068230 A1 | 8/2003 |
| WO | 03/097062 A1 | 11/2003 |

OTHER PUBLICATIONS

Extended European Search Report for EP 05805957.7 and PCT/JP2005020555 dated Jun. 3, 2009.

*Primary Examiner*—Janet L. Andres
*Assistant Examiner*—Raymond Covington
(74) *Attorney, Agent, or Firm*—Sughrue Mion, PLLC

(57) ABSTRACT

The present invention relates to a compound that has p38 MAP kinase inhibitory activity useful as drug medicine, represented by the general formula (I):

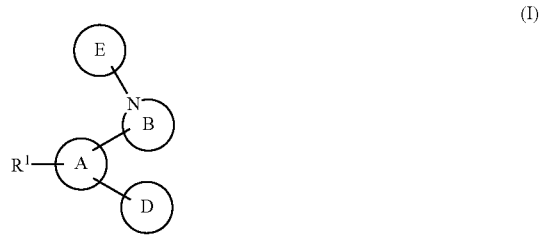

wherein all the symbols are as defined in the description, or its salt, N-oxide or solvate, or a prodrug thereof. Further, there are provided a process for producing the same and usage thereof.

The compound of the general formula (I) has a p38 MAP kinase inhibitory activity and is useful for the prevention and/or treatment of diseases in which an abnormal production of cytokine, such as inflammatory cytokine or chemokine, or an over-reaction thereto would be instrumental in the cause and aggravation of pathologic condition thereof, namely, cytokine-mediated diseases, for example, inflammatory diseases, respiratory diseases, circulatory diseases, central nervous diseases, etc.

13 Claims, No Drawings

NITROGENOUS HETEROCYCLIC COMPOUND AND PHARMACEUTICAL USE THEREOF

TECHNICAL FIELD

The present invention relates to the nitrogenous heterocyclic compound that has p38 MAP kinase inhibitory activity and is useful as drug medicine, the process for preparation thereof and the use thereof.

BACKGROUND ART p38 mitogen-activated protein (MAP) kinase (p38α/Mpk2/RK/SAPK2a/CSBP) (hereinafter referred to as "p38 MAP kinase") was cloned as an enzyme which induces tyrosine phosphorylation in monocyte after stimulation with lipopolysaccharide (LPS) (*Nature,* 372, 739 (1994)), and is activated by various extracellular stimuli [physical stimuli (osmotic shock, heat shock, UV irradiation, and so forth), chemical stimuli (endotoxin, hydrogen peroxide, arsenic trioxide, an inflammatory cytokine, a growth factor, and so forth), and so on]. Also, since p38 MAP kinase is involved in the production of an inflammatory cytokine (such as tumor necrosis factor-α (TNF-α), interleukin-1 (IL-1), IL-6, IL-8, and so forth), a chemokine, and so on, an association between the activation of this enzyme and diseases is strongly suggested. Therefore, an improvement effect on various disease symptoms typified by inflammatory diseases is expected by suppression of p38 MAP kinase activation.

Accordingly, a p38 MAP kinase inhibitor is expected to be useful in prevention and/or treatment of those diseases that are supposedly caused or deteriorated by abnormal production of cytokines including inflammatory cytokine or chemokine, or by over response thereto, namely cytokine-mediated diseases such as various inflammatory diseases [for example, inflammation, dermatitis, atopic dermatitis, hepatitis, nephritis, glomerulonephritis, pancreatitis, psoriasis, gout, Addison's disease, arthritis (e.g., rheumatoid arthritis, osteoarthritis, rheumatoid spondylitis, gouty arthritis, synovitis, etc.), inflammatory ocular diseases, inflammatory pulmonary diseases (e.g., chronic pneumonia, silicosis, pulmonary sarcoidosis, pulmonary tuberculosis, adult respiratory distress syndrome (ARDS), severe acute respiratory syndrome (SARS), etc.), inflammatory bowel diseases (e.g., Crohn's disease, ulcerative colitis, etc.), allergic diseases (e.g., allergic dermatitis, allergic rhinitis, etc.), autoimmune disease, autoimmune hemolytic anemia, systemic lupus erythematosus, rheumatism, Castleman's disease, immune rejection accompanying transplantation (e.g., graft versus host reaction, etc.), and so forth], central nervous system disorders [for example, central neuropathy (e.g., cerebrovascular disease such as cerebral hemorrhage and cerebral infarction, head trauma, spinal cord injury, cerebral edema, multiple sclerosis, etc.), neurodegenerative disease (e.g., Alzheimer's disease, Parkinson's disease, amyotrophic lateral sclerosis (ALS), AIDS encephalopathy, etc.), meningitis, Creutzfeldt-Jakob syndrome, and so forth], respiratory diseases [for example, asthma, chronic obstructive pulmonary disease (COPD), and so forth], cardiovascular diseases [for example, angina, heart failure (e.g., congestive heart failure, acute heart failure, chronic heart failure, etc.), myocardial infarction (e.g., acute myocardial infarction, myocardial infarction prognosis, etc.), atrial myxoma, arteriosclerosis, hypertension, dialysis-induced hypotension, thrombosis, disseminated intravascular coagulation (DIC), reperfusion injury, restenosis after percutaneous transluminal coronary angioplasty (PTCA), and so forth], urinary diseases [for example, renal failure, and so forth], metabolic diseases or endocrine diseases [for example, diabetes, and so forth], bone diseases [for example, osteoporosis, and so forth], cancerous diseases [for example, malignant tumor (e.g., tumor growth and metastasis, etc.), multiple myeloma, plasma cell leukemia, carcinemia, and so forth], and infectious diseases [for example, viral infection (e.g., cytomegalovirus infection, influenza virus infection, herpes virus infection, corona virus infection, etc.), cachexia associated with infections, cachexia caused by acquired immune deficiency syndrome (AIDS), toxemia (e.g., sepsis, septic shock, endotoxin shock, gram negative bacterial sepsis, toxic shock syndrome, severe acute respiratory syndrome (SARS) accompanying virus infection, etc.), and so forth], and so on.

On the other hand, WO 01/096308 discloses that the compounds represented by general formula (W), the salts thereof, or the hydrate thereof have an inhibitory effect on AMPA receptor and/or kainic acid receptor:

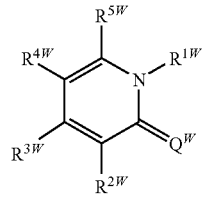

(W)

wherein $Q^W$ represents NH, O or S;

$R^{1W}$, $R^{2W}$, $R^{3W}$, $R^{4W}$ and $R^{5W}$ represent, samely or differently, hydrogen atom, halogen atom, C1-6 alkyl, or —$X^W$-$A^W$ (wherein $X^W$ represents a bond, an optionally substituted C1-6 alkylene, an optionally substituted C2-6 alkenylene, an optionally substituted C2-6 alkynylene, —O—, —S—, —CO—, —SO—, —SO$_2$—, —N($R^{6W}$)—, —N($R^{7W}$)—CO—, —CO—N($R^{8W}$)—, —N($R^{9W}$)—CH$_2$—, —CH$_2$—N($R^{10W}$)—, —CH$_2$—CO—, —CO—CH$_2$—, —N($R^{11W}$)—S(O)$_{mW}$—, —S(O)$_{nW}$—N($R^{12W}$)—, —CH$_2$—S(O)$_{pW}$—, —S(O)$_{qW}$—CH$_2$—, —CH$_2$—O—, —O—CH$_2$—, —N($R^{13W}$)—CO—N($R^{14W}$)—, or —N($R^{15W}$)—CS—N($R^{16W}$)— (wherein $R^{6W}$, $R^{7W}$, $R^{8W}$, $R^{9W}$, $R^{10W}$, $R^{11W}$, $R^{12W}$, $R^{13W}$, $R^{14W}$, $R^{15W}$ and $R^{16W}$ represent hydrogen atom, C1-6 alkyl or C1-6 alkoxy; mW, nW, pW and qW each independently represents 0 or an integer of 1 or 2); $A^W$ represents C3-8 cycloalkyl, C3-8 cycloalkenyl, a non-aromatic 5- to 14-membered hetero ring, an aromatic C6-14 hydrocarbon ring or an aromatic 5- to 14-membered hetero ring, and these rings are optionally substituted by substituent respectively);

with the proviso that, three of $R^{1W}$, $R^{2W}$, $R^{3W}$, $R^{4W}$ and $R^{5W}$, samely or differently, represent —$X^W$-$A^W$ and residual two always represent hydrogen atom, halogen atom, or C1-6 alkyl;

provided that in the above-mentioned definition, the cases where (1) $Q^W$ is O; $R^{1W}$ and $R^{5W}$ are hydrogen atom; and $R^{2W}$, $R^{3W}$ and $R^{4W}$ are phenyl groups, (2) $Q^W$ is O; $R^{1W}$ and $R^{4W}$ are hydrogen atom; and $R^{2W}$, $R^{3W}$ and $R^{5W}$ are phenyl groups, and (3) $Q^W$ is O; $R^{1W}$ and $R^{2W}$ are hydrogen atom; and $R^{3W}$, $R^{4W}$ and $R^{5W}$ are phenyl groups, are excluded.

Also, Japanese Publication Toku-Kai-Syo 60-58981 discloses that 1,3-thiazole derivatives represented by general formula (Y) or the salts thereof have inhibitory effects on pain, fever, inflammation, ulcer, thromboxane A$_2$ (TXA$_2$) synthesis, and platelet aggregation:

(Y structure with R2Y, R3Y, R1Y on thiazole)

wherein $R^{1Y}$ represents cycloalkyl, cyclic amino, amino having 1 or 2 substituent(s) selected from the group consisting of lower alkyl, phenyl, acetyl, and lower alkoxycarbonylacetyl, alkyl which may be substituted by hydroxyl, carboxyl or lower alkoxycarbonyl, or phenyl which may be substituted by carboxyl, 2-carboxyetenyl or 2-carboxy-1-propenyl;

$R^{2Y}$ represents pyridyl which may be substituted by lower alkyl;

$R^{3Y}$ represents lower alkoxy, lower alkyl, hydroxyl, halogen, or phenyl which may be substituted by methylenedioxy.

Moreover, WO 00/064894 discloses that the compounds represented by general formula (Z) which may be N-oxidated or the salts thereof are useful as p38 MAP kinase inhibitors:

(Z)

wherein $R^{1Z}$ represents hydrogen atom, an optionally substituted hydrocarbon, an optionally substituted hetero ring, an optionally substituted amino or acyl;

$R^{2Z}$ represents an optionally substituted aromatic group;

$R^{3Z}$ represents hydrogen atom, an optionally substituted pyridyl, or an optionally substituted aromatic hydrocarbon;

$X^Z$ represents oxygen atom or an optionally oxidized sulfur atom;

$Y^Z$ represents a bond, oxygen atom, an optionally oxidized sulfur atom, or $NR^{4Z}$ (wherein $R^{4Z}$ represents hydrogen atom, an optionally substituted hydrocarbon, or acyl);

$Z^Z$ represents a bond or a bivalent aliphatic hydrocarbon which may have a substituent(s).

Furthermore, WO 03/043988 discloses that the compounds represented by general formula (A) or the non-toxic salts thereof are useful as p38 MAP kinase inhibitors:

(A)

wherein $A^A$ represents a C5-10 mono- or poly-cyclic carbon ring, or a 5- to 10-membered mono- or poly-cyclic hetero ring containing 1 to 5 nitrogen atom(s), 1 to 2 oxygen atom(s) and/or 1 sulfur atom;

$R^{1A}$ represents (1) C1-8 alkyl, (2) C2-8 alkenyl, (3) C2-8 alkynyl, (4) halogen atom, (5) —$OR^{4A}$, (6) —$NR^{5A}R^{6A}$, (7) —$NR^{7A}COR^{8A}$, (8) —$CONR^{9A}R^{10A}$, (9) —$COOR^{11A}$, (10) —$SO_2NR^{12A}R^{13A}$, (11) —$NR^{14A}SO_2R^{15A}$, (12) —$SR^{16A}$, (13) —$S(O)R^{17A}$, (14) —$SO_2R^{18A}$, (15) —$NR^{22A}COOR^{23A}$, (16) —$NR^{24A}CONR^{25A}R^{26A}$, (17) —$COR^{27A}$, (18) nitro, (19) cyano, (20) trifluoromethyl, (21) trifluoromethoxy, (22) $Cyc1^A$, or the like;

$R^{4A}$-$R^{18A}$ and $R^{22A}$-$R^{27A}$ each independently represent a hydrogen atom, C1-8 alkyl $Cyc1^A$, or the like;

$Cyc1^A$ represents a C5-10 mono- or poly-cyclic carbon ring or the like (with the proviso that, the carbon ring or the like may be substituted with one to five $R^{48A}(s)$);

$R^{48A}$ represents C1-8 alkyl, halogen atom, nitro, cyano, or the like;

$R^{2A}$ represents C1-8 alkyl, —$OR^{20A}$, —$NR^{64A}R^{65A}$, —$COOR^{66A}$, —$CONR^{67A}R^{68A}$, —$NR^{69A}COR^{70A}$, —$SO_2R^{71A}$, —$SO_2NR^{72A}R^{73A}$, —$NR^{74A}SO_2R^{75A}$, —$NR^{76A}COOR^{77A}$, $Cyc2^A$ or the like;

$R^{20A}$ and $R^{64A}$-$R^{77A}$ each independently represents hydrogen atom, C1-8 alkyl, $Cyc2^A$, or the like;

$Cyc2^A$ represents a C5-6 mono-cyclic carbon ring or the like (with the proviso that, the carbon ring or the like may be substituted by one to five substituent(s) such as C1-8 alkoxy, halogen atom or the like);

$G^A$ and $J^A$ each independently represents a carbon, nitrogen, oxygen, or sulfur atom;

$E^A$ represents C1-4 alkylene, —O—, —S—, or the like (with the proviso that, the C1-4 alkylene may be substituted by one to five substituent(s) such as C1-8 alkoxy, halogen atom, hydroxy, or the like);

$B^A$ represents a C5-10 mono- or poly-cyclic carbon ring, or a 5- to 10-membered mono- or poly-cyclic hetero ring containing 1 to 4 nitrogen atom(s), 1 to 2 oxygen atom(s) and/or 1 sulfur atom;

$R^{3A}$ represents C1-8 alkyl, C2-8 alkenyl, C2-8 alkynyl, halogen atom, —$OR^{81A}$, —$NR^{82A}R^{83A}$, —$NR^{84A}COR^{85A}$, —$CONR^{86A}R^{87A}$, —$COOR^{88A}$, —$SO_2NR^{89A}R^{90A}$, —$NR^{91A}SO_2R^{92A}$, —$SR^{93A}$, —$S(O)R^{94A}$, —$SO_2R^{95A}$, —$NR^{96A}COOR^{97A}$, —$NR^{98A}CONR^{99A}R^{100A}$, —$OCONR^{101A}R^{102A}$, nitro, cyano, trifluoromethyl, trifluoromethoxy, $Cyc4^A$, or the like;

$R^{81A}$-$R^{102A}$ each independently represents hydrogen atom, C1-8 alkyl, $Cyc4^A$, or the like;

$Cyc4^A$ represents a C5-10 mono- or poly-cyclic carbon ring or the like (with the proviso that, the carbon ring or the like may be substituted by one to five substituent(s) such as C1-8 alkoxy, halogen atom or the like);

mA represents 0 or an integer of 1 to 5;

nA represents 0 or an integer of 1 to 7;

iA represents 0 or an integer of 1 to 12, with the proviso that, only necessary part of the meanings of the symbols in the formula were excerpted.

And more, WO 01/030778 discloses that the compounds represented by general formula (B), the pharmaceutically-acceptable cleavable esters thereof, or the acid-addition salts thereof are useful as p38 MAP kinase inhibitors:

(B)

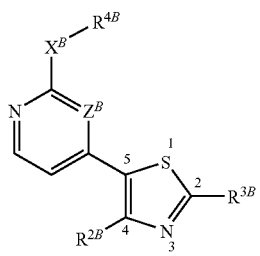

wherein $Z^B$ represents N or CH;

$X^B$ represents —$NR^{6B}$—$Y^B$—, —O— or —S— (wherein $R^{6B}$ represents hydrogen atom, C1-4 alkyl, C3-8 cycloalkyl, C3-8 cycloalkyl C1-3 alkyl, C6-18 aryl, C3-18 heteroaryl, C7-19 aralkyl, or C4-19 heteroaralkyl, and —$Y^B$— represents C1-4 alkylene or a bond);

$R^{2B}$ represents phenyl which may be substituted by one or more substituent(s), the substituent(s) are selected from the group consisting of halo, trifluoromethyl, cyano, amide, thioamide, carboxylate, thiocarboxylate, C1-4 alkoxy, C1-4 alkyl, or amino which may be substituted by one or two C1-4 alkyl;

$R^{3B}$ represents hydrogen atom, C1-10 alkyl, C3-10 cycloalkyl, C3-18 heterocycloalkyl, C6-18 aryl, or C3-18 heteroaryl, and each may have up to four substituent(s) selected from the group consisting of C1-4 alkyl, halogen atom, halogen-substituted C1-4 alkyl, hydroxy, C1-4 alkoxy, C1-4 alkylthio, or amino which may be substituted by one or two C1-4 alkyl, or 5- to 7-membered nitrogenous hetero ring optionally containing further hetero atom selected from oxygen, sulfur or nitrogen atom;

$R^{4B}$ represents C6-18 aryl, C3-18 heteroaryl or C3-12 cycloalkyl, substituted by up to four substituent(s) selected from the group consisting of C1-4 alkyl, halogen atom, halogen-substituted C1-4 alkyl, hydroxy, C1-4 alkoxy, C1-4 alkylthio, or optionally mono- or di-C1-C4alkyl substituted amino, or by N-heterocyclyl containing from 5 to 7 ring atoms and optionally containing a further hetero atom selected from O, S or N.

DISCLOSURE OF THE INVENTION

It is earnestly desired to develop p38 MAP kinase inhibitors useful for prevention and/or treatment of various diseases typically such as inflammatory diseases, which are excellent in oral absorption, and can be safely administered.

As a result of the present inventors intensively studied to find compounds which are useful as agents for treatment of various diseases typically such as inflammatory diseases by suppressing the activity of p38 MAP kinase as the subject, they found that the novel nitrogenous heterocyclic compounds represented by the following general formula (I) inhibit p38 MAP kinase strongly. Additionally, the compounds represented by general formula (I) of the present invention inhibit TNF-α production strongly in vitro and in vivo, and thus the present invention has been completed.

Thus, the present invention relates to
[1] a compound represented by general formula (I):

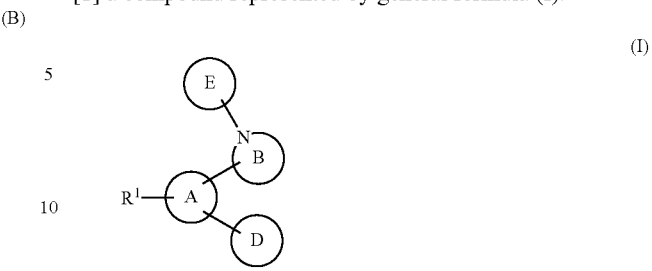

wherein ring A represents a 5-membered monocyclic hetero ring which contains 1 to 3 atom(s) selected from the group consisting of oxygen atom, nitrogen atom and sulfur atom as a hetero atom, and which may have a further substituent(s);

ring B represents an optionally substituted hetero ring containing at least one nitrogen atom;

ring D represents an optionally substituted cyclic group ring E represents an optionally substituted cyclic group; and $R^1$ represents a substituent which contains nitrogen atom(s) having basicity;

or its salt, N-oxide or solvate, or a prodrug thereof;

[2] the compound according to above [1], wherein ring A is

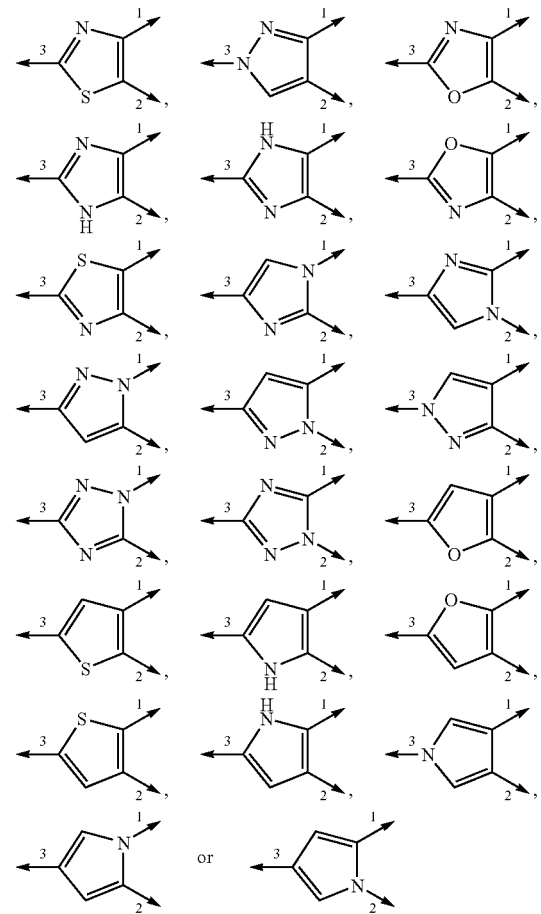

in which arrowhead 1 represents a bond with ring B;
arrowhead 2 represents a bond with ring D;
arrowhead 3 represents a bond with $R^1$; and the nitrogen atom represented by NH may have a substituent; and may have a further substituent(s);

[3] the compound according to above [1], wherein ring A is

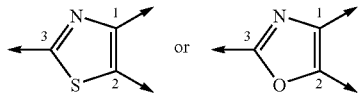

in which all symbols have the same meanings as described in above [2];

[4] the compound according to above [1], wherein ring B is

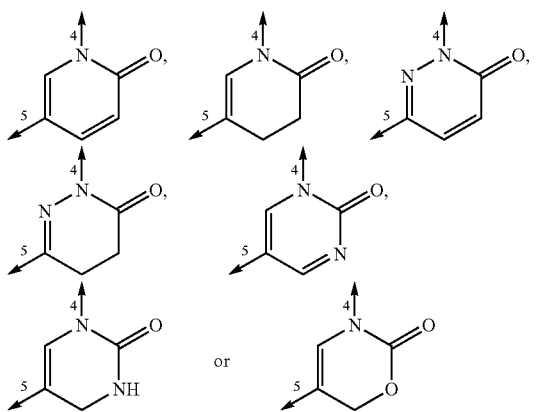

in which arrowhead 4 represents a bond with ring E; and arrowhead 5 represents a bond with ring A;

[5] the compound according to above [1], wherein $R^1$ is an optionally substituted hetero ring which contains at least one nitrogen atom having basicity, an optionally substituted amino, an aliphatic hydrocarbon group substituted by an optionally substituted amino, or an aliphatic hydrocarbon group substituted by an optionally substituted hetero ring which contains at least one nitrogen atom having basicity;

[6] the compound according to above [1], wherein $R^1$ is an optionally substituted hetero ring which contains at least one nitrogen atom having basicity;

[7] the compound according to above [1], wherein $R^1$ is pyrrolidine, piperidine or perhydroazepine ring, which may have substituent(s);

[8] the compound according to above [1], wherein $R^1$ is

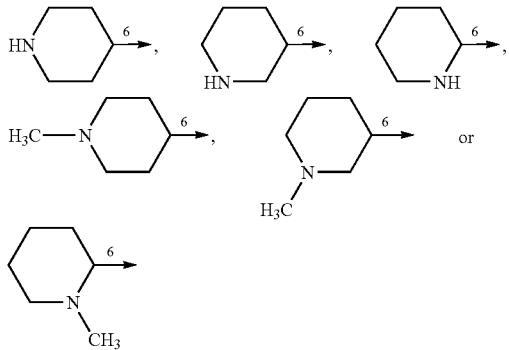

in which arrowhead 6 represents a bond with ring A;

[9] the compound according to above [1], represented by general formula (Ia), (Ib), (Ic), or (Id):

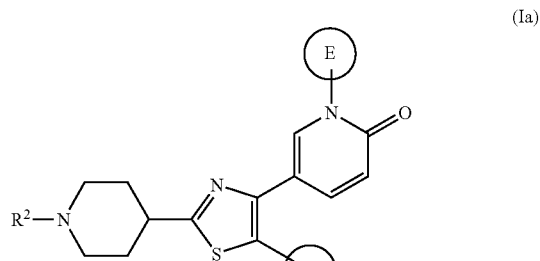

(Ia)

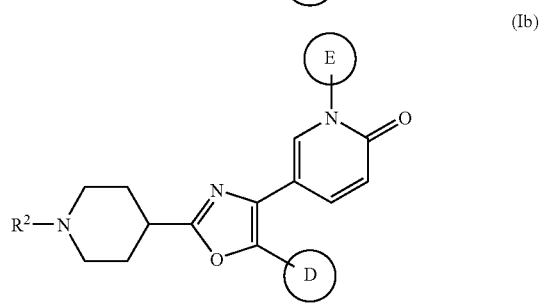

(Ib)

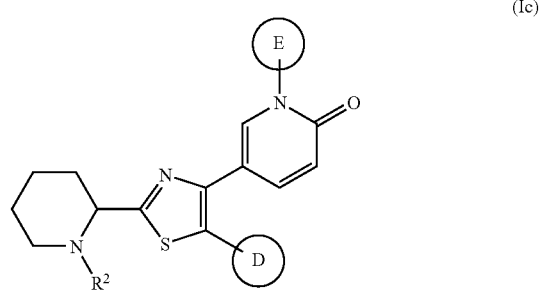

(Ic)

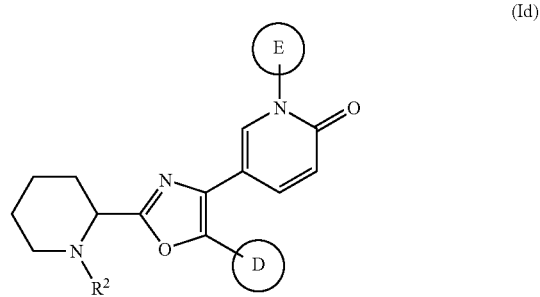

(Id)

in which $R^2$ represents a hydrogen atom or a substituent; and all other symbols have the same meanings as described in above [1];

[10] the compound according to above [2], wherein ring D is an optionally substituted 5- to 10-membered carbon ring or an optionally substituted 5- to 10-membered hetero ring;

[11] the compound according to above [10], wherein ring D is an optionally substituted benzene ring;

[12] the compound according to above [4], wherein ring E is an optionally substituted 5- to 10-membered carbon ring or an optionally substituted 5- to 10-membered hetero ring;

[13] the compound according to above [12], wherein ring E is an optionally substituted benzene ring;

[14] the compound according to above [11] or [13], wherein the substituent of ring D and/or ring E is C1-4 alkyl, C1-4 alkoxy and/or halogen atom;

[15] the compound according to above [1], selected from the group consisting of
(1) 5-[5-(2-chloro-4-fluorophenyl)-2-piperidin-4-yl-1,3-thiazol-4-yl]-1-(2,6-dichlorophenyl)pyridin-2(1H)-one,
(2) 5-[5-(2-chloro-4-fluorophenyl)-2-(1-ethylpiperidin-4-yl)-1,3-thiazol-4-yl]-1-(2,6-dichlorophenyl)pyridin-2(1H)-one,
(3) 5-[5-(2-chloro-4-fluorophenyl)-2-(1-isopropylpiperidin-4-yl)-1,3-thiazol-4-yl]-1-(2,6-dichlorophenyl)pyridin-2(1H)-one,
(4) 5-[5-(2-chloro-4-fluorophenyl)-2-(1-methylpiperidin-4-yl)-1,3-thiazol-4-yl]-1-(2,6-dichlorophenyl)pyridin-2(1H)-one,
(5) 5-(5-(2-chloro-4-fluorophenyl)-2-{1-[2-(dimethylamino)ethyl]piperidin-4-yl}-1,3-thiazol-4-yl)-1-(2,6-dichlorophenyl)pyridin-2(1H)-one,
(6) 5-[5-(2,4-difluorophenyl)-2-(1-methylpiperidin-4-yl)-1,3-thiazol-4-yl]-1-(2,6-dimethylphenyl)pyridin-2(1H)-one,
(7) 5-[5-(2,4-difluorophenyl)-2-(1-methylpiperidin-4-yl)-1,3-oxazol-4-yl]-1-(2,6-dimethylphenyl)pyridin-2(1H)-one,
(8) 1-(2,6-difluorophenyl)-5-[5-(2,4-difluorophenyl)-2-(1-methylpiperidin-4-yl)-1,3-thiazol-4-yl]pyridin-2(1H)-one,
(9) 5-[5-(2,4-difluorophenyl)-2-(1-methylpiperidin-4-yl)-1,3-oxazol-4-yl]-1-(4-fluoro-2,6-dimethylphenyl)pyridin-2(1H)-one,
(10) 1-(2,6-difluorophenyl)-5-[5-(2,4-difluorophenyl)-2-(1-methylpiperidin-4-yl)-1,3-oxazol-4-yl]pyridin-2(1H)-one,
(11) 5-[5-(2,4-difluorophenyl)-2-(1-methylpiperidin-4-yl)-1,3-thiazol-4-yl]-1-(4-methoxy-2,6-dimethylphenyl)pyridin-2(1H)-one,
(12) 1-(4-chloro-2,6-dimethylphenyl)-5-[5-(2,4-difluorophenyl)-2-(1-methylpiperidin-4-yl)-1,3-oxazol-4-yl]pyridin-2(1H)-one,
(13) 1-(2-chloro-6-methylphenyl)-5-[5-(2,4-difluorophenyl)-2-(1-methylpiperidin-4-yl)-1,3-oxazol-4-yl]pyridin-2(1H)-one,
(14) 5-[5-(2,4-difluorophenyl)-2-(1-methylpiperidin-4-yl)-1,3-oxazol-4-yl]-1-(2-fluorophenyl)pyridin-2(1H)-one,
(15) 5-[5-(2,4-difluorophenyl)-2-(1-methylpiperidin-4-yl)-1,3-oxazol-4-yl]-1-(2,4,6-trifluorophenyl)pyridin-2(1H)-one,
(16) 5-[5-(2,4-difluorophenyl)-2-(1-methylpiperidin-4-yl)-1,3-oxazol-4-yl]-1-(2,3,6-trifluorophenyl)pyridin-2(1H)-one,
(17) 5-[5-(2,4-difluorophenyl)-2-(1-methylpiperidin-4-yl)-1,3-oxazol-4-yl]-1-(2-fluoro-6-methylphenyl)pyridin-2(1H)-one,
(18) 1-(2,6-difluorophenyl)-5-[5-(4-fluorophenyl)-2-(1-methylpiperidin-4-yl)-1,3-oxazol-4-yl]pyridin-2(1H)-one,
(19) 5-[5-(2,4-difluorophenyl)-2-(1-methylpiperidin-4-yl)-1,3-oxazol-4-yl]-1-(4-methoxy-2,6-dimethylphenyl)pyridin-2(1H)-one,
(20) 1-(2,6-dimethylphenyl)-5-[5-(2-fluoro-4-methylphenyl)-2-(1-methylpiperidin-4-yl)-1,3-oxazol-4-yl]pyridin-2(1H)-one,
(21) 5-{5-(2,4-difluorophenyl)-2-[(3R)-piperidin-3-yl]-1,3-oxazol-4-yl}-1-(2,6-dimethylphenyl)pyridin-2(1H)-one,
(22) 5-{5-(2,4-difluorophenyl)-2-[(3R)-1-methylpiperidin-3-yl]-1,3-oxazol-4-yl}-1-(2,6-dimethylphenyl)pyridin-2(1H)-one,
(23) 5-{5-(2,4-difluorophenyl)-2-[(3S)-piperidin-3-yl]-1,3-oxazol-4-yl}-1-(2,6-dimethylphenyl)pyridin-2(1H)-one,
(24) 5-{5-(2,4-difluorophenyl)-2-[(3S)-1-methylpiperidin-3-yl]-1,3-oxazol-4-yl}-1-(2,6-dimethylphenyl)pyridin-2(1H)-one,
(25) 1-(2,6-difluorophenyl)-5-{5-(2,4-difluorophenyl)-2-[(2S)-1-methyl-2-piperidinyl]-1,3-oxazol-4-yl}-2(1H)-pyridinone, and
(26) 1-(2,6-difluorophenyl)-5-{5-(2,4-difluorophenyl)-2-[(2R)-1-methyl-2-piperidinyl]-1,3-oxazol-4-yl}-2(1H)-pyridinone;

[16] a pharmaceutical composition comprising a compound represented by general formula (I) depicted in above [1], or its salt, N-oxide or solvate, or a prodrug thereof;

[17] the composition according to above [16], which is a p38 MAP kinase inhibitor and/or a TNF-α production inhibitor;

[18] the composition according to above [16], which is an agent for prevention and/or treatment of a cytokine-mediated disease;

[19] the composition according to above [18], wherein the cytokine-mediated disease is an inflammatory disease, a cardiovascular disease, a respiratory disease, and/or a bone disease;

[20] the composition according to above [19], wherein the inflammatory disease is rheumatoid arthritis;

[21] a combination medicine comprising a compound represented by general formula (I) depicted in above [1], or its salt, N-oxide or solvate, or a prodrug thereof, and one or two or more compound(s) selected from the group consisting of a non-steroidal anti-inflammatory agent, a disease modifying anti-rheumatic drug, an anticytokine protein preparation, a cytokine inhibitor, an immunomodulator, a steroidal agent, an adhesion molecule inhibitor, an elastase inhibitor, a cannabinoid-2 receptor stimulant, a prostaglandin, a prostaglandin synthase inhibitor, a phosphodiesterase inhibitor and a metalloproteinase inhibitor;

[22] a method for prevention and/or treatment of a cytokine-mediated disease in a mammal, which comprises administering an effective amount of a compound represented by general formula (I) depicted in above [1], or its salt, N-oxide or solvate, or a prodrug thereof to a mammal;

[23] use of a compound represented by general formula (I) depicted in above [1], or its salt, N-oxide or solvate, or a prodrug thereof for the manufacture of an agent for prevention and/or treatment of a cytokine-mediated disease;

[24] the compound according to above [1], which inhibits TNF-α production 90% or more at the dose of 3 mg/kg in rat cytokine production model; and

[25] a process for preparation of the compound represented by general formula (I) depicted in above [1], or its salt, N-oxide or solvate, or a prodrug thereof.

Effect of the Invention

The compounds of the present invention are low toxicity and strongly inhibit p38 MAP kinase and/or TNF-α production, so they are useful as agents for prevention and/or treatment of cytokine-mediated diseases such as inflammatory diseases, central nervous system disorders, respiratory diseases, cardiovascular diseases, urinary diseases, metabolic diseases, endocrine diseases, bone diseases, cancerous diseases, infectious diseases, and so forth.

BEST MODE FOR CARRYING OUT THE INVENTION

In the description of the present invention, the "cyclic group" in the "optionally substituted cyclic group" represented by ring D or ring E includes, for example, a carbon ring, a hetero ring, and so forth. Said "carbon ring" only has to be a carbon ring, and there is no particular limitation for the number of atoms that constitute said "carbon ring". As preferable carbon ring, for example, a "5- to 10-membered mono- or poly-cyclic carbon ring" and so forth can be cited. It includes, for example, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene ring, and so forth. Also, said "5- to 10-membered mono- or poly-cyclic carbon ring" includes, a spiro-fused poly-cyclic carbon ring and a bridged poly-cyclic carbon ring, too. It includes, for example, spiro[4.4]nonane, spiro[4.5]decane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane ring, and so forth. Among these, as a "5- to 10-membered mono- or poly-cyclic aromatic carbon ring", for example, benzene ring and naphthalene ring can be cited preferably. Said "hetero ring" only has to be a hetero ring, and there is no particular limitation for the number of atoms that constitute said "hetero ring". As preferable hetero ring, for example, a "5- to 10-membered mono- or poly-cyclic hetero ring" and so forth can be cited. As said "5- to 10-membered mono- or poly-cyclic hetero ring", a "5- to 10-membered mono- or poly-cyclic hetero ring containing 1 to 5 nitrogen atom(s), 1 to 2 oxygen atom(s) and/or 1 sulfur atom, a spiro-fused poly-cyclic hetero ring, and a bridged poly-cyclic hetero ring" and so forth can be cited. It includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydroxepine, tetrahydroxepine, perhydroxepine, dihydrothiophene, tetrahydrothiophene, dihydrothiopyran, tetrahydrothiopyran, dihydrothiepine, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydrooxazine, tetrahydrooxazine, dihydroxadiazine, tetrahydroxadiazine, dihydroxazepine, tetrahydroxazepine, perhydroxazepine, dihydroxadiazepine, tetrahydroxadiazepine, perhydroxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazin, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dioxaindan, benzodioxane, chroman ring, and so forth. Moreover, among said "5- to 10-membered mono- or poly-cyclic hetero ring containing 1 to 5 nitrogen atom(s), 1 to 2 oxygen atom(s) and/or 1 sulfur atom, a spiro-fused poly-cyclic hetero ring, and a bridged poly-cyclic hetero ring", "a spiro-fused poly-cyclic hetero ring, and a bridged poly-cyclic hetero ring" includes, for example, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane ring, and so forth. Among these, as a "5- to 10-membered mono- or poly-cyclic aromatic hetero ring containing 1 to 4 nitrogen atom(s), 1 to 2 oxygen atom(s) and/or 1 sulfur atom", for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole ring, and so forth can be cited.

In the description of the present invention, there is no particular limitation for the "substituent" in the "optionally substituted cyclic group" represented by ring D or ring E so long as it can be a substituent. Said "substituent" includes, for example, (1) an optionally substituted aliphatic hydrocarbon group, (2) a substituent selected from the Group I shown below, (3) an optionally substituted 5- to 10-membered carbon ring, (4) an optionally substituted 5- to 10-membered hetero ring, or the like. One to twelve substituent(s), preferably one to three substituent(s) among these optional substituents may be located at any position where substitution is possible.

The "aliphatic hydrocarbon group" in the "optionally substituted aliphatic hydrocarbon group" includes, for example, a "straight or branched aliphatic hydrocarbon group", and so forth. Said "straight or branched aliphatic hydrocarbon group" includes, for example, a "C1-8 aliphatic hydrocarbon group", and so forth. Said "C1-8 aliphatic hydrocarbon group" includes, for example, C1-8 alkyl (e.g., methyl, ethyl, propyl, isopropyl, butyl, sec-butyl, tert-butyl, pentyl, hexyl, heptyl, octyl, and isomers thereof, etc.), C2-8 alkenyl (e.g., vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl, and isomers thereof, etc.), C2-8 alkynyl (e.g., ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl, and isomers thereof, etc.), and so forth.

There is no particular limitation for the "substituent" in the "optionally substituted aliphatic hydrocarbon group" so long as it can be a substituent. Said "substituent" includes, for example, (1) a substituent selected from the Group I shown below, (2) an optionally substituted 5- to 10-membered carbon ring, (3) an optionally substituted 5- to 10-membered hetero ring, or the like.

One to five substituent(s) among these optional substituents may be located at any position where substitution is possible.

<Group I>

(a) halogen atom (e.g., chlorine, bromine, fluorine, iodine atom), (b) —$OR^{a1}$, (c) —$NR^{a1}R^{a2}$, (d) —$NR^{a1}COR^{a2}$, (e) —$CONR^{a1}R^{a2}$, (f) —$COOR^{a1}$, (g) —$SO_2NR^{a1}R^{a2}$, (h) —$NR^{a1}SO_2R^{a2}$, (i) —$SR^{a1}$, (j) —$S(O)R^{a1}$, (k) —$SO_2R^{a1}$, (l) —$COR^{a1}$, (m) nitro, (n) cyano, (o) trifluoromethyl, (r) trifluoromethoxy, (s) —C=($NOR^{a1}$)$R^{a2}$ [in these groups, $R^{a1}$ and $R^{a2}$ each independently represents a hydrogen atom, an optionally substituted C1-8 alkyl, an optionally substituted 5- to 10-membered carbon ring, or an optionally substituted 5- to 10-membered hetero ring].

Here, the "C1-8 alkyl" in the "optionally substituted C1-8 alkyl" represented by $R^{a1}$ and $R^{a2}$ has the same meaning as defined above. Also, there is no particular limitation for the "substituent" in the "optionally substituted C1-8 alkyl" represented by $R^{a1}$ and $R^{a2}$ so long as it can be a substituent. Said "substituent" includes, for example, (1) a substituent selected from the Group II shown below, (2) an optionally substituted 5- to 10-membered carbon ring, (3) an optionally substituted 5- to 10-membered hetero ring, or the like. One to five substituent(s) among these optional substituents may be located at any position where substitution is possible.

<Group II>

(a) —$OR^{b1}$, (b) —$NR^{b1}R^{b2}$, (c) —$NR^{b1}COR^{b2}$, (d) —$CONR^{b1}R^{b2}$, (e) —$COOR^{b1}$, (f) —$SO_2NR^{b1}R^{b2}$, (g) —$NR^{b1}SO_2R^{b2}$ (h) —$CONR^{b1}NR^{b2}R^{b3}$ and (i) —$CONR^{b1}OR^{b2}$ [in these groups, $R^{b1}$, $R^{b2}$ and $R^{b3}$ each independently represents a hydrogen atom, an optionally substituted C1-8 alkyl, an optionally substituted 5- to 10-membered carbon ring, or an optionally substituted 5- to 10-membered hetero ring].

Here, the "C1-8 alkyl" in the "optionally substituted C1-8 alkyl" represented by $R^{b1}$, $R^{b2}$ and $R^{b3}$ has the same meaning as defined above. Also, there is no particular limitation for the "substituent" in the "optionally substituted C1-8 alkyl" represented by $R^{b1}$, $R^{b2}$ and $R^{b3}$ so long as it can be a substituent. Said "substituent" includes, for example, (1) a substituent selected from the Group III shown below, (2) an optionally substituted 5- to 10-membered carbon ring, (3) an optionally substituted 5- to 10-membered hetero ring, or the like. One to five substituent(s) among these optional substituents may be located at any position where substitution is possible.

<Group III>

(a) —$OR^{c1}$ and (b) —$NR^{c1}R^{c2}$ [in these groups, $R^{c1}$ and $R^{c2}$ each independently represents a hydrogen atom, an optionally substituted C1-8 alkyl, an optionally substituted 5- to 10-membered carbon ring, or an optionally substituted 5- to 10-membered hetero ring].

Here, the "C1-8 alkyl" in the "optionally substituted C1-8 alkyl" represented by $R^{c1}$ and $R^{c2}$ has the same meaning as defined above. Also, there is no particular limitation for the "substituent" in the "optionally substituted C1-8 alkyl" represented by $R^{c1}$ and $R^{c2}$ so long as it can be a substituent. Said "substituent" includes, for example, (1) an optionally substituted 5- to 10-membered carbon ring, (2) an optionally substituted 5- to 10-membered hetero ring, or the like. One to five substituent(s) among these optional substituents may be located at any position where substitution is possible.

The "5- to 10-membered carbon ring" in the "optionally substituted 5- to 10-membered carbon ring" in the "substituent" of ring D or ring E has the same meaning as the "5- to 10-membered mono- or poly-cyclic carbon ring" defined above. Also, the "5- to 10-membered hetero ring" in the "optionally substituted 5- to 10-membered hetero ring" has the same meaning as the "5- to 10-membered mono- or poly-cyclic hetero ring" defined above. Moreover, there is no particular limitation for the "substituent" in the "optionally substituted 5- to 10-membered carbon ring" or the "optionally substituted 5- to 10-membered hetero ring" so long as it can be a substituent. Said "substituent" includes, for example, (1) a substituent selected from the Group IV shown below, (2) an optionally substituted 5- to 6-membered cyclic group, or the like. One to five substituent(s) among these optional substituents may be located at any position where substitution is possible.

<Group IV>

(a) C1-8 alkyl (having the same meaning as defined above), (b) halogen atom (having the same meaning as defined above), (c) nitro, (d) cyano, (e) —$OR^{d1}$, (f) —$NR^{d1}R^{d2}$, (g) —$COOR^{d1}$, (h) —$COR^{d1}$, (i) —$CONR^{d1}R^{d2}$, (j) —$NR^{d1}COR^{d2}$, (k) —$SO_2NR^{d1}R^{d2}$, (l) —$NR^{d1}SO_2R^{d2}$, (m) —$SR^{d1}$, (n) —$SO_2R^{d1}$, (o) oxo, and (p) thioxo [in these groups, $R^{d1}$ and $R^{d2}$ each independently represents a hydrogen atom or a C1-8 alkyl (having the same meaning as defined above)].

The "5- to 6-membered cyclic group" in the "optionally substituted 5- to 6-membered cyclic group" in the "substituent" of ring D or ring E includes, for example, a "5- to 6-membered mono-cyclic carbon ring", a "5- to 6-membered mono-cyclic hetero ring", or the like. Said "5- to 6-membered mono-cyclic carbon ring" includes, for example, cyclopentane, cyclohexane, cyclopentene, cyclohexene, cyclopentadiene, cyclohexadiene, benzene ring or the like. On the other hand, as the "5- to 6-membered mono-cyclic hetero ring", for example, a "5- to 6-membered mono-cyclic hetero ring containing 1 to 4 nitrogen atom(s), 1 to 2 oxygen atom(s) and/or 1 sulfur atom", and so forth can be cited. Said "5- to 6-membered mono-cyclic hetero ring containing 1 to 4 nitrogen atom(s), 1 to 2 oxygen atom(s) and/or 1 sulfur atom" includes, for example, pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydrois othiazole (isothiazolidine), dihydrofurazan, tetrahydrofurazan, dihydroxadiazole, tetrahydroxadiazole (oxadiazolidine), dihydrooxazine, tetrahydrooxazine, dihydroxadiazine, tetrahydroxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, dioxolane, dioxane ring, and so forth.

There is no particular limitation for the "substituent" in the "optionally substituted 5- to 6-membered cyclic group" represented by ring D or ring E so long as it can be a substituent. Said "substituent" includes, for example, (1) C1-8 alkyl (having the same meaning as defined above), (2) C1-8 alkoxy (e.g., methoxy, ethoxy, propoxy, isopropoxy, butoxy, sec-butoxy, tert-butoxy, pentyloxy, hexyloxy, heptyloxy, octyloxy, and isomers thereof, etc.), (3) halogen atom (having the same meaning as defined above), (4) trifluoromethyl, (5) trifluoromethoxy, or the like. One to five substituent(s) among these optional substituents may be located at any position where substitution is possible.

In the description of the present invention, the "5-membered monocyclic hetero ring which contains 1 to 3 atom(s) selected from the group consisting of oxygen atom, nitrogen atom and sulfur atom as a hetero atom" in the "5-membered monocyclic hetero ring which contains 1 to 3 atom(s) selected from the group consisting of oxygen atom, nitrogen atom and sulfur atom as a hetero atom, and which may have a further substituent(s)" represented by ring A includes, for example, pyrrole, imidazole, triazole, pyrazole, furan, thiophene, oxazole, isoxazole, thiazole, isothiazole, pyrroline, pyrrolidine, imidazoline, imidazolidine, triazoline, triazolidine, pyrazoline, pyrazolidine, dihydrofuran, tetrahydrofuran, dihydrothiophene, tetrahydrothiophene, dihydrooxazole, tetrahydrooxazole, dihydroisoxazole, tetrahydroisoxazole, dihydrothiazole, tetrahydrothiazole, dihydroisothiazole, tetrahydroisothiazole, dioxolane, dithiolane ring, and so forth. Among these, as a "5-membered monocyclic aromatic hetero ring which contains 1 to 3 atom(s) selected from the group consisting of oxygen atom, nitrogen atom and sulfur atom", for example, pyrrole, imidazole, triazole, pyrazole, furan, thiophene, oxazole, isoxazole, thiazole, isothiazole ring, and so forth can be cited.

In the description of the present invention, there is no particular limitation for the "substituent" in the "5-membered monocyclic hetero ring which contains 1 to 3 atom(s) selected from the group consisting of oxygen atom, nitrogen atom and sulfur atom as a hetero atom, and which may have a further substituent(s)" represented by ring A so long as it can be a substituent, and the substituent may substitute to nitrogen atom in NH. Said substituent includes, for example, (1) the "optionally substituted 5- to 6-membered cyclic group" defined above, (2) a substituent selected from the Group V shown below, (3) an optionally substituted aliphatic hydrocarbon group, or the like. One or two substituent(s) among these optional substituents may be located at any position where substitution is possible.

<Group V>

(a) —$OR^{e1}$, (b) —$NR^{e1}R^{e2}$, (c) —$COOR^{e1}$, (d) —$CONR^{e1}R^{e2}$, (e) —$NR^{e1}COR^{e2}$, (f) —$SO_2R^{e1}$, (g) —$SO_2NR^{e1}R^{e2}$, (h) —$NR^{e1}SO_2R^{e2}$, (i) —$SR^{e1}$, (j) —$S(O)R^{e1}$, (k) —$COR^{e1}$, (l) —$C=(NOR^{e1})R^{e2}$, (m) nitro, (n) cyano, (o) trifluoromethyl, (p) trifluoromethoxy [in these groups, $R^{e1}$ and $R^{e2}$ each independently represents a hydrogen atom or an optionally substituted C1-8 alkyl].

Here, the "C1-8 alkyl" in the "optionally substituted C1-8 alkyl" represented by $R^{e1}$ and $R^{e2}$ has the same meaning as defined above. Also, there is no particular limitation for the "substituent" in the "optionally substituted C1-8 alkyl" represented by $R^{e1}$ and $R^{e2}$ so long as it can be a substituent. Said "substituent" includes, for example, the "optionally substituted 5- to 6-membered cyclic group" defined above or the like. One to five substituent(s) among these optional substituents may be located at any position where substitution is possible.

The "aliphatic hydrocarbon group" in the "optionally substituted aliphatic hydrocarbon group" has the same meaning as the "aliphatic hydrocarbon group" in the "optionally substituted aliphatic hydrocarbon group" as defined in the "substituent" of ring D or ring E.

There is no particular limitation for the "substituent" in the "optionally substituted aliphatic hydrocarbon group" so long as it can be a substituent. Said "substituent" includes, for example, (1) the "optionally substituted 5- to 6-membered cyclic group" defined above, (2) a substituent selected from the Group VI shown below, or the like. One to five substituent(s) among these optional substituents may be located at any position where substitution is possible.

<Group VI>

(a) —$OR^{f1}$, (b) —$NR^{f1}R^{f2}$, (c) —$COOR^{f1}$, (d) —$CONR^{f1}R^{f2}$, (e) —$NR^{f1}COR^{f2}$, (f) —$SO_2R^{f1}$, (g) —$SO_2NR^{f1}R^{f2}$, (h) —$NR^{f1}SO_2R^{f2}$, (i) —$NR^{f1}COOR^{f2}$, [in these groups, $R^{f1}$ and $R^{f2}$ each independently represents a hydrogen atom or an optionally substituted C1-8 alkyl].

Here the "C1-8 alkyl" in the "optionally substituted C1-8 alkyl" represented by $R^{f1}$ and $R^{f2}$ has the same meaning as defined above. Also, there is no particular limitation for the "substituent" in the "optionally substituted C1-8 alkyl" represented by $R^{f1}$ and $R^{f2}$ so long as it can be a substituent. Said "substituent" includes, for example, the "optionally substituted 5- to 6-membered cyclic group" defined above or the like. One to five substituent(s) among these optional substituents may be located at any position where substitution is possible.

In the description of the present invention, the "hetero ring containing at least one nitrogen atom" in the "optionally substituted hetero ring containing at least one nitrogen atom", includes any ring as long as it has one nitrogen atom as constituent atom which binds to above-mentioned ring E, and there is no limitation for the other constituent atom(s). As said "hetero ring containing at least one nitrogen atom", a "5- to 10-membered mono- or poly-cyclic hetero ring containing at least one nitrogen atom" and so forth can be cited. Said "5- to 10-membered mono- or poly-cyclic hetero ring containing at least one nitrogen atom" includes, for example, pyrrole, imidazole, triazole, tetrazole, pyrazole, pyridine, pyrazine, pyrimidine, pyridazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydrooxazine, tetrahydrooxazine, dihydroxadiazine, tetrahydroxadiazine, dihydroxazepine, tetrahydroxazepine, perhydroxazepine, dihydroxadiazepine, tetrahydroxadiazepine, perhydroxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzofurazan, benzothiadiazole, benzotriazole, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole ring, and so forth.

In the description of the present invention, there is no particular limitation for the "substituent" in the "optionally substituted hetero ring containing at least one nitrogen atom" represented by ring B so long as it can be a substituent. Said "substituent" includes, for example, (1) an optionally substituted C1-8 alkyl, (2) the "optionally substituted 5- to 6-membered cyclic group" defined above, (3) a substituent selected from the Group V shown above, (4) oxo, (5) thioxo, or the like. One to nine substituent(s), preferably one to three substituent(s) among these optional substituents may be located at any position where substitution is possible. Here, there is no particular limitation for the substituent in the "optionally substituted C1-8 alkyl" as the "substituent" of ring B. Said substituent includes, for example, (1) the "optionally substituted 5- to 6-membered cyclic group" defined above or (2) a substituent selected from the Group VI shown above, or the like. One to five substituent(s) among these optional substituents may be located at any position where substitution is possible.

In the description of the present invention, the "substituent which contains nitrogen atom(s) having basicity" represented by $R^1$ includes, for example, (1) an "optionally substituted hetero ring which contains at least one nitrogen atom having basicity", (2) an "optionally substituted amino", (3) an "aliphatic hydrocarbon group substituted by an optionally substituted amino", (4) an "aliphatic hydrocarbon group substituted by an optionally substituted hetero ring which contains at least one nitrogen atom having basicity", or the like. The "hetero ring which contains at least one nitrogen atom having basicity" in the "optionally substituted hetero ring which contains at least one nitrogen atom having basicity" or the "aliphatic hydrocarbon group substituted by an optionally substituted hetero ring which contains at least one nitrogen atom having basicity" includes, for example, azetidine, pyrrolidine, piperidine, azepine, diazepine, pyrazoline, thiazoline, isothiazoline, oxazoline, isoxazoline, imidazoline, 1,2,3- or 1,2,4-triazoline, pyridine, pyrimidine, pyrazine, pyridazine, 1,3,5- or 1,2,4-triazine, piperazine, morpholine, thiomorpholine, naphthyridine, tetrahydronaphthyridine, quinoline, isoquinoline, tetrahydroquinoline, indoline, isoindoline, quinazoline, quinoxaline, tetrahydroquinoxaline, benzooxazoline, benzothiazolone, benzimidazoline ring, or the like. The "substituent" in the "optionally substituted hetero ring which contains at least one nitrogen atom having basicity" or the "aliphatic hydrocarbon group substituted by an optionally substituted hetero ring which contains at least one nitrogen atom having basicity" has the same meaning as the "substituent" in the "optionally substituted hetero ring containing at least one nitrogen atom" as defined in the "substituent" of ring B.

The "optionally substituted amino" in the "optionally substituted amino" or the "aliphatic hydrocarbon group substituted by an optionally substituted amino" includes, for example, an "amino which may have one or two substituent(s)" or the like. The "substituent" in said "amino which may have one or two substituent(s)" includes, for example, (1) an optionally substituted C1-8 alkyl (having the same meaning as defined above), (2) an optionally substituted 5- to 6-membered cyclic group (having the same meaning as defined above), or the like. As the "amino which may have one or two substituent(s)", particularly for example, N-methylamino, N-ethylamino, N-propylamino, N-isopropylamino, N-butylamino, N-isobutylamino, N-tert-butylamino, N-pentylamino, N-hexylamino, N-benzylamino, N-cyclopropylamino, N-cyclopentylamino, N-cyclohexylamino, N-phenylamino, N-(dimethylamino)ethyl, N,N-dimethylamino, N,N-diethylamino, N,N-dipropylamino, N,N-dibutylamino, N,N-dipentylamino, N,N-dihexylamino, N-methyl-N-ethylamino, N,N-dibenzylamino, N-benzyl-N-methylamino, N-benzyl-N-ethylamino, N,N-diphenylamino, N-phenyl-N-methylamino, N-phenyl-N-ethylamino, and so forth can be cited. The "aliphatic hydrocarbon group" in the "aliphatic hydrocarbon group substituted by an optionally substituted amino" or the "aliphatic hydrocarbon group substituted by an optionally substituted hetero ring which contains at least one nitrogen atom having basicity" has the same meaning as the "aliphatic hydrocarbon group" in the "optionally substituted aliphatic hydrocarbon group" as defined in the "substituent" of ring D or ring E.

In the description of the present invention, $R^2$ means "a hydrogen atom or a substituent". Said "substituent" has the same meaning as the "substituent" in the "optionally substituted hetero ring which contains at least one nitrogen atom having basicity" or the "aliphatic hydrocarbon group substituted by an optionally substituted hetero ring which contains at least one nitrogen atom having basicity" as defined in the "substituent which contains nitrogen atom(s) having basicity" represented by $R^1$.

In the description of the present invention, any rings, any groups and any atoms represented by ring A, ring B, ring D, ring E and $R^1$ are all preferable. Hereinafter, preferable groups, preferable rings and preferable atoms are listed, and all symbols as used herein have the same meanings as those defined above.

In the description of the present invention, preferable example of the "5-membered monocyclic hetero ring which contains 1 to 3 atom(s) selected from the group consisting of oxygen atom, nitrogen atom and sulfur atom as a hetero atom" in the "5-membered monocyclic hetero ring which contains 1 to 3 atom(s) selected from the group consisting of oxygen atom, nitrogen atom and sulfur atom as a hetero atom, and which may have a further substituent(s)" represented by ring A includes, for example, a "5-membered monocyclic aromatic hetero ring which contains 1 to 3 atom(s) selected from the group consisting of oxygen atom, nitrogen atom and sulfur atom as a hetero atom", and so forth. More preferable example includes, for example, ring:

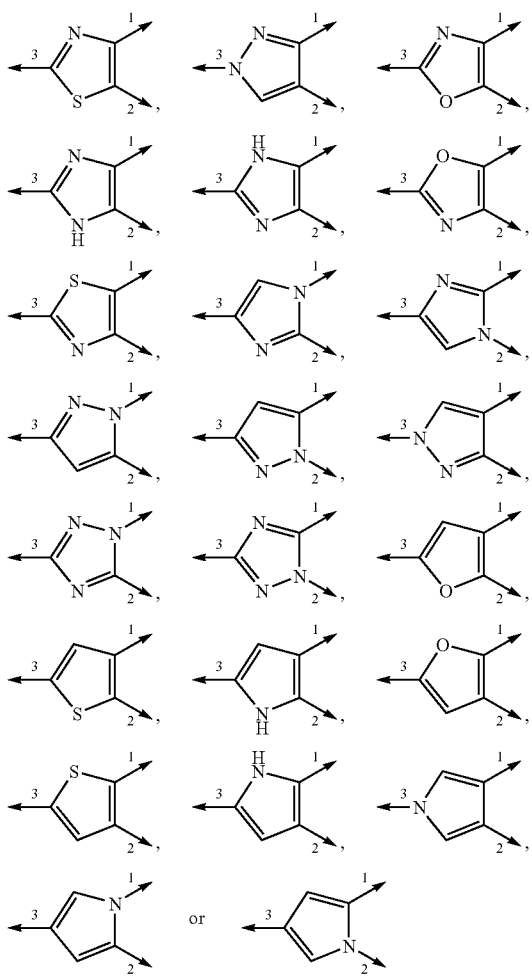

in which all other symbols have the same meanings as described above, and so forth. Most preferable example includes, for example, ring:

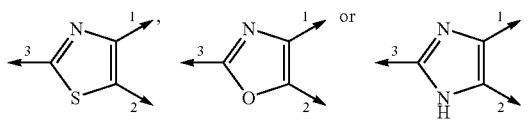

in which all other symbols have the same meaning as described above, and so forth. Above all, ring:

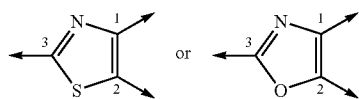

in which all other symbols have the same meanings as described above, is most preferable example.

And preferable example of the "substituent" of the "5-membered monocyclic hetero ring which contains 1 to 3 atom(s) selected from the group consisting of oxygen atom, nitrogen atom and sulfur atom as a hetero atom, and which may have a further substituent(s)" includes, for example, C1-8 alkyl, and so forth. More preferable example includes, for example, methyl, and so forth. And also, ring A is preferable at the unsubstituted state.

In the description of the present invention, preferable example of the "hetero ring containing at least one nitrogen atom" in the "optionally substituted hetero ring containing at least one nitrogen atom" includes, for example, a "5- to 10-membered mono- or poly-cyclic hetero ring containing at least one nitrogen atom", and so forth. More preferable example includes, for example, a "5- to 7-membered monocyclic hetero ring containing at least one nitrogen atom", and so forth. Most preferable example includes, for example, a "6-membered mono-cyclic hetero ring containing at least one nitrogen atom", and so forth. And preferable example of the "substituent" of the "optionally substituted hetero ring containing at least one nitrogen atom" includes, for example, a group which has one oxo without fail. More preferable example includes, for example, oxo which binds to carbon atom adjacent to nitrogen atom. It is preferable that other substituent(s) is not exist (namely unsubstituted). Also it is preferable that there is C1-4alkyl, —OR$^{e1}$, —COOR$^{e1}$, and so forth as other substituent(s). More preferably, there is no substituent(s) or there is methyl, ethyl, —OH, —OCH$_3$, —COOH, —COOCH$_3$, and so forth as substituent(s). Most preferably, there is no substituent(s). More specifically, preferable example of the "optionally substituted hetero ring containing at least one nitrogen atom" includes, for example, ring:

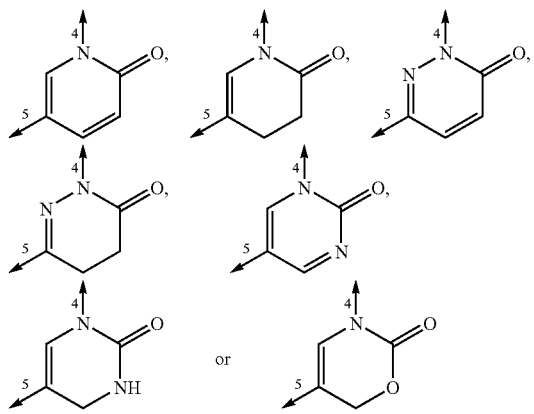

in which all other symbols have the same meanings as described above, and so forth. More preferable example includes, for example, ring:

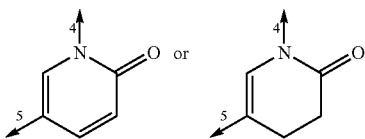

in which all other symbols have the same meanings as described above, and so forth. More preferable example includes, for example, ring:

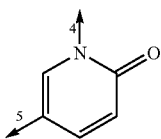

in which all other symbols have the same meanings as described above, and so forth.

In the description of the present invention, preferable example of ring D includes, for example, a "5- to 10-membered mono- or poly-cyclic carbon ring", a "5- to 10-membered mono- or poly-cyclic hetero ring", and so forth. More preferable example includes, for example, a "5- to 10-membered mono- or poly-cyclic aromatic carbon ring", a "5- to 10-membered mono- or poly-cyclic aromatic hetero ring", and so forth. More preferable example includes, for example, a "5- to 6-membered mono-cyclic aromatic carbon ring", a "5- to 6-membered mono-cyclic aromatic hetero ring having 1 to 2 nitrogen atom(s), 1 oxygen atom and/or 1 sulfur atom", and so forth. Most preferable example includes, for example, benzene, thiophen, pyrrole, pyridine ring, and so forth. Above all, benzene ring is most preferable example. And preferable example of the "substituent" of said "optionally substituted cyclic group" includes, for example, an "optionally substituted 5- to 10-membered hetero ring", C1-8 alkyl, halogen atom, $-NR^{a1}R^{a2}$, $-NR^{a1}COR^{a2}$, $-COOR^{a2}$, $-CONR^{a1}R^{a2}$, $-COR^{a1}$, $-SO_2NR^{a1}R^{a2}$, $-NR^{a1}SO_2R^{a2}$, $-OR^{a1}$, C1-4alkyl substituted by $-OR^{a1}$, and so forth. More preferable example includes, for example, C1-4 alkyl, C1-4 alkoxy, halogen atom, $-CONR^{a1}R^{a2}$, $-NR^{a1}R^{a2}$, $-NR^{a1}COR^{a2}$, and so forth. Most preferable example includes, for example, C1-4 alkyl (e.g., methyl, ethyl, propyl, isopropyl, butyl, sec-butyl, tert-butyl and isomers thereof, etc.), C1-4 alkoxy (e.g., methoxy, ethoxy, propoxy, isopropoxy, butoxy, sec-butoxy, tert-butoxy and isomers thereof, etc.), halogen atom (e.g., chlorine, bromine, fluorine, iodine atom), and so forth. Above all, methyl, ethyl, methoxy, fluorine atom or chlorine atom is preferable, and methyl, fluorine atom is more preferable. The number of substituent(s) is preferably 1 to 3, and more preferably 1 to 2. In addition, in case where ring D is benzene ring, the position of the substituent(s) of said benzene ring is preferably 2-position and/or 4-position as the position of atom that binds to ring A is 1-position.

In the description of the present invention, preferable example of ring E includes, for example, a "5- to 10-membered mono- or poly-cyclic carbon ring", a "5- to 10-membered mono- or poly-cyclic hetero ring", and so forth. More preferable example includes, for example, a "5- to 10-membered mono- or poly-cyclic aromatic carbon ring", a "5- to 10-membered mono- or poly-cyclic aromatic hetero ring", and so forth. More preferable example includes, for example, a "5- to 6-membered mono-cyclic aromatic carbon ring", a "5- to 6-membered mono-cyclic aromatic hetero ring having 1 to 2 nitrogen atom(s), 1 oxygen atom and/or 1 sulfur atom", and so forth. Most preferable example includes, for example, benzene, thiophen, pyrrole, pyridine ring, and so forth. Above all, benzene ring is most preferable. And preferable example of the "substituent" of said "optionally substituted cyclic group" includes, for example, an "optionally substituted 5- to 10-membered hetero ring", C1-8 alkyl, halogen atom, $-NR^{a1}R^{a2}$, $-NR^{a1}COR^{a2}$, $-COOR^{a2}$, $-CONR^{a1}R^{a2}$, $-COR^{a1}$, $-SO_2NR^{a1}R^{a2}$, $-NR^{a1}SO_2R^{a2}$, $-OR^{a1}$, C1-4alkyl substituted by $-OR^{a1}$, and so forth. More preferable example includes, for example, C1-4 alkyl, C1-4 alkoxy, halogen atom, $-CONR^{a1}R^{a2}$, $-NR^{a1}R^{a2}$, $-NR^{a1}COR^{a2}$, and so forth. Most preferable example includes, for example, C1-4 alkyl (e.g., methyl, ethyl, propyl, isopropyl, butyl, sec-butyl, tert-butyl and isomers thereof, etc.), C1-4 alkoxy (e.g., methoxy, ethoxy, propoxy, isopropoxy, butoxy, sec-butoxy, tert-butoxy and isomers thereof, etc.), halogen atom (e.g., chlorine, bromine, fluorine, iodine atom), and so forth. Above all, methyl, ethyl, methoxy, fluorine atom or chlorine atom is preferable, and methyl, fluorine atom is more preferable. The number of substituent(s) is preferably 1 to 3, and more preferably 1 to 2. In addition, in case where ring E is benzene ring, the position of the substituent(s) of said benzene ring is preferably 2-position, 4-position and/or 6-position as the position of atom that binds to ring B is 1-position.

In the description of the present invention, preferable example of the "substituent which contains nitrogen atom(s) having basicity" represented by $R^1$ includes, for example, an "optionally substituted hetero ring which contains at least one nitrogen atom having basicity", an "optionally substituted amino", an "aliphatic hydrocarbon group substituted by an optionally substituted amino", an "aliphatic hydrocarbon group substituted by an optionally substituted hetero ring which contains at least one nitrogen atom having basicity", and so forth. More preferable example includes, for example, an "optionally substituted hetero ring which contains at least one nitrogen atom having basicity", and so forth. Most preferable example includes, for example, an optionally substituted pyrrolidine ring, an optionally substituted piperidine ring, an optionally substituted piperazine ring, an optionally substituted perhydroazepine ring, and so forth. Above all, an optionally substituted piperidine ring is most preferable. Also, preferable example of the "substituent(s)" of the "optionally substituted hetero ring which contains at least one nitrogen atom having basicity", the "optionally substituted amino", the "aliphatic hydrocarbon group substituted by an optionally substituted amino", or the "aliphatic hydrocarbon group substituted by an optionally substituted hetero ring which contains at least one nitrogen atom having basicity" represented by the "substituent which contains nitrogen atom(s) having basicity" includes, for example, hydrogen atom, an optionally substituted C1-8 alkyl, an optionally substituted 5- to 6-membered cyclic ring, and so forth. More preferable example includes, for example, hydrogen atom, an optionally substituted C1-4 alkyl, and so forth. Most preferable example includes, for example, hydrogen atom, methyl, ethyl, isopropyl, (diethylamino)ethyl, and so forth. Specifically, the preferable group as $R^1$ includes piperidin-4-yl, 1-methylpiperidin-4-yl, piperidin-3-yl, 1-methylpiperidin-3-yl, piperidin-2-yl, 1-methylpiperidin-2-yl, 1-ethylpiperidin-4-yl, 1-isopropylpiperidin-4-yl, 1-[2-(dimethylamino)ethyl]piperidin-4-yl, 1-methylpiperazin-4-yl, 1-ethylpiperazin-4-yl, 1-isopropylpiperazin-4-yl, N-[(dimethylamino)ethyl]amino, N-methyl-N-ethylamino, (dimethylamino)propyl, (dimethylamino)ethyl, and so forth. The more preferable example group as $R^1$ includes piperidin-4-yl, 1-methylpiperidin-4-yl, piperidin-3-yl, 1-methylpiperidin-3-yl, piperidin-2-yl, 1-methylpiperidin-2-yl, 1-ethylpiperidin-4-yl, 1-isopropylpiperidin-4-yl, 1-[2-(dimethylamino)ethyl]piperidin-4-yl, and so forth. Especially, the group represented by

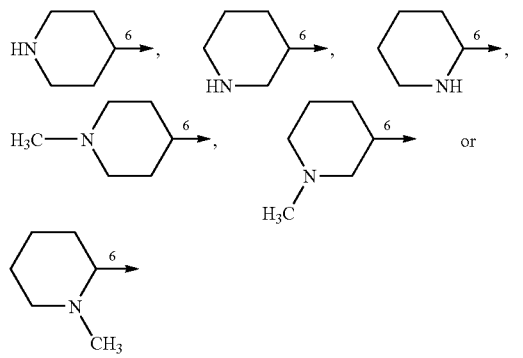

in which arrowhead 6 has the same meaning as described in above is most preferable.

In the description of the present invention, a compound represented by general formula (I) comprising a combination of preferable groups, preferable rings, and preferable atoms as defined above is preferable. The preferable example includes, for example, a compound represented by general formula (Ia):

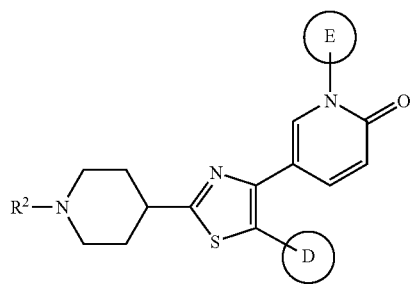

(Ia)

in which all symbols have the same meanings as described above, a compound represented by general formula (Ib):

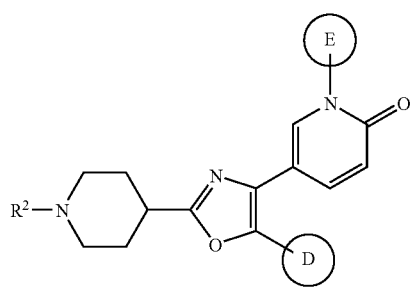

(Ib)

in which all symbols have the same meanings as described above, a compound represented by general formula (Ic):

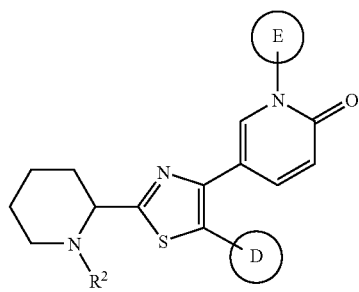

(Ic)

in which all symbols have the same meanings as described above, or a compound represented by general formula (Id):

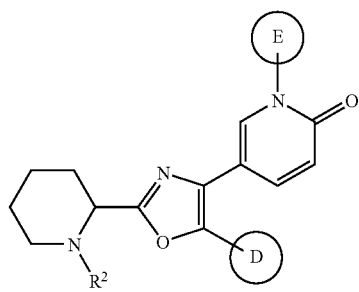

(Id)

in which all symbols have the same meanings as described above, or its salt, N-oxide or solvate, or a prodrug thereof.

The most preferable example includes, for example, a compound represented by general formula (I-A):

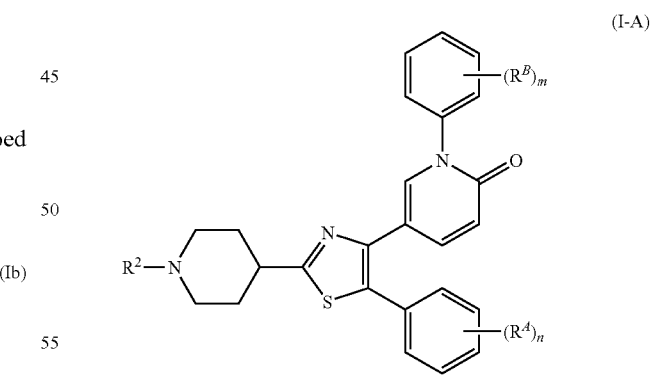

(I-A)

wherein, $R^A$ and $R^B$ represent the "substituent" in the "optionally substituted cyclic group";

n represents 0 or an integer of 1 to 5;

m represents 0 or an integer of 1 to 5 wherein when n is 2 or more, $R^A$ is same or different;

when m is 2 or more, $R^B$ is same or different); and all other symbols have the same meanings as described above, a compound represented by general formula (I-B):

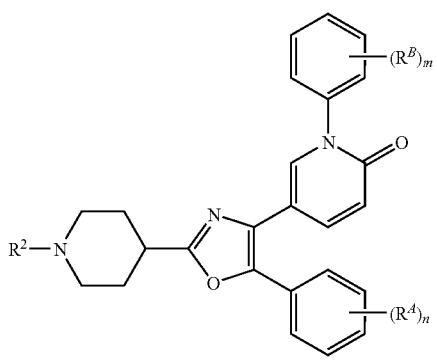

(I-B)

in which all symbols have the same meanings as described above, a compound represented by general formula (I-C):

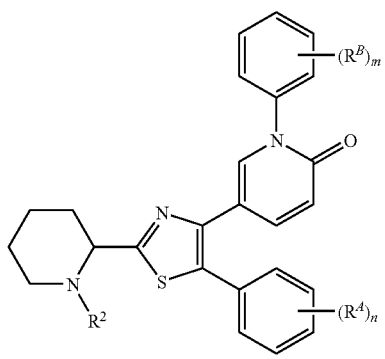

(I-C)

in which all symbols have the same meanings as described above, or a compound represented by general formula (I-D):

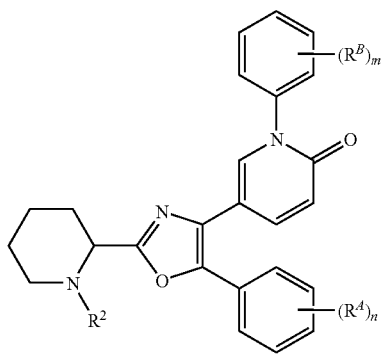

(I-D)

in which all symbols have the same meanings as described above, or its salt, N-oxide or solvate, or a prodrug thereof.

Also, in the description of the present invention, the compounds disclosed in Examples, or its salt, N-oxide or solvate, or a prodrug thereof are all preferable.

Unless otherwise specified, any isomers are all included in the present invention. For example, as structural isomer, linear or branched ones are included in the alkyl, alkoxy, and alkylene groups. Further, the present invention includes isomers due to double bond, ring, and fused ring (E-form, Z-form, cis-form, trans-form), isomers due to the presence of asymmetric carbon atom (R-form, S-form, α-form, β-form, enantiomer, diastereomer), optically active compounds with optical rotation (D-form, L-form, d-form, l-form), compounds with axial asymmetry (atropisomer), polar compounds obtained by chromatographic separation (high polar compound, low polar compound), equilibrium compounds, and mixtures of these compounds in an arbitrary ratio (for example, about from 95:5 to 55:45 (mass ratio)), and racemates. Moreover, the present invention includes all tautomers.

[Salt, N-oxide, Solvate and Prodrug]

Pharmacologically acceptable salts are all included in the salts of compounds represented by general formula (I). The pharmacologically acceptable salts are preferably those which are non-toxic and soluble in water. Examples of suitable salts are salts of alkali metals (e.g., potassium, sodium, lithium, etc.), salts of alkaline earth metals (e.g., calcium, magnesium, etc.), ammonium salts (e.g., tetramethylammonium salt, tetrabutylammonium salt, etc.), salts of organic amines (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts [inorganic acid salts (e.g., hydrochloride, hydrobromide, hydroiodide, sulfate, phosphate, nitrate, etc.), organic acid salts (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucronate, gluconate, etc.), etc.].

Further, such salts include quaternary ammonium salts. The quaternary ammonium salts can be those wherein the nitrogen atom in the compound represented by general formula (I) is quaternized by $R^O$ group. Examples of $R^O$ are a C1-8 alkyl group, and a phenyl-substituted C1-8 alkyl group.

The N-oxides of the compounds represented by general formula (I) are ones wherein the nitrogen atom of the compound represented by general formula (I) is oxidized. Also, the N-oxides of the present invention may be present in the form of alkaline (earth) metal salts, ammonium salts, organic amine salts or acid addition salts.

Suitable solvates of the compounds represented by general formula (I) includes, for example, a solvate with water or an alcoholic solvent (e.g., ethanol, etc.). The solvates are preferably non-toxic and soluble in water. The solvates of the present invention includes solvates of alkaline (earth) metal salts, ammonium salts, organic amine salts, acid addition salts or N-oxides of the compounds of the present invention represented by general formula (I).

The compounds represented by general formula (I) may be converted into the above salts, the above N-oxides, or the above solvates by the known method.

The prodrugs of the compounds represented by general formula (I) are those which can be converted into the compounds of the general formula (I) of the present invention by the in vivo action of enzymes or gastric acid. Examples of the prodrugs of compounds represented by general formula (I) are (1) those wherein the amino group is acylated, alkylated, or phosphorylated (for example, compounds wherein the amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, t-butylated, etc.), when compounds represented by general formula (I) contain an amino group; (2) those wherein the hydroxy group is acylated, alkylated, phosphorylated, or borated (for example, compounds wherein the hydroxy group is acetylated, palmitoylated, propanoylated, pivaloylated, succinylated, fumarylated, alanylated, dimethylaminocabonylated, etc.), when compounds represented by general formula (I) contain a hydroxy group; and (3) those wherein the carboxyl group is esterified, or amidated (for example, compounds wherein the carboxyl group is converted into an ester such as ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, and cyclohexyloxycarbonylethyl ester, or compounds wherein the carboxyl group is methylamidated). These compounds can be prepared by the conventional method. The prodrug of the compound represented by general formula (I) is any one of hydrates and non-hydrates. The prodrug of the compound represented by general formula (I) is a compound which may be converted into a compound represented by general formula (I) under physiological conditions as described in Development of Drugs, Molecule Design, vol. 7, pp. 163-198, (1990), published by Hirokawa Publishing Co., Japan. Further, the compound represented by general formula (I) may be labelled with an isotope (e.g., $^3$H, $^{14}$C, $^{35}$S, $^{125}$I, etc.).

Mechanical IUPAC nomenclature of the compounds of the present invention was performed using a computer program ACD/NAME (Trade Name) available from Advanced Chemistry Development Co. For example, the following compound was named 5-[5-(2-chloro-4-fluorophenyl)-2-piperidin-4-yl-1,3-thiazol-4-yl-1-(2,6-dichlorophenyl)pyridin-2(1H)-one.

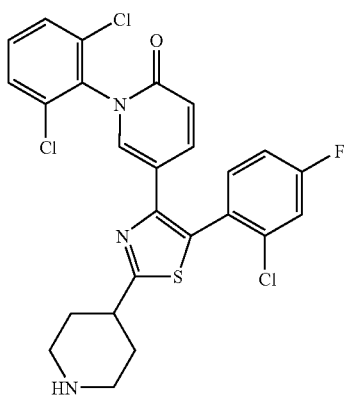

[Process for Preparation of the Compounds of the Present Invention]

The compounds represented by general formula (I), or its salt, N-oxide or solvate, or a prodrug thereof (hereinafter, abbreviated to "the compound(s) of the present invention") can be prepared by the known method, for example, an appropriately improved or combined method of Methods (A) to (F) shown below, similar methods thereof, the method as described in Examples, and the method described in Comprehensive Organic Transformations: A Guide to Functional Group Preparations, 2nd Edition (Richard C. Larock, John Wiley & Sons Inc., 1999). The starting material in each preparation method shown below may be used in the form of a salt. Such salt used is the salt of the compounds represented by general formula (I) as defined above.

(A) Among the compounds represented by general formula (I) of the present invention, a compound wherein ring A represents a thiazole ring, that is, a compound represented by general formula (I-1):

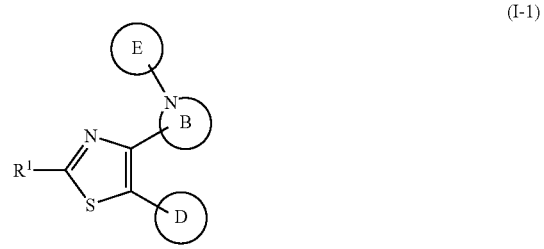

wherein all symbols have the same meanings as described above or a compound represented by general formula (I-2):

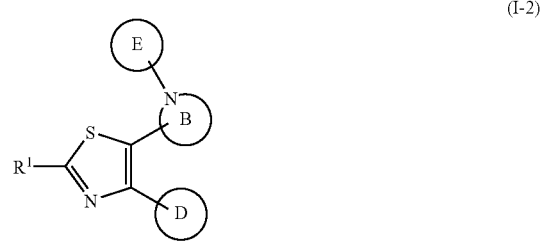

wherein all symbols have the same meanings as described above can be prepared by subjecting a compound represented by general formula (1):

wherein all symbols have the same meanings as described above or a compound represented by general formula (2):

wherein all symbols have the same meanings as described above and a compound represented by general formula (3):

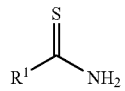

(3)

wherein R¹ has the same meaning as described above to a ring formation reaction. If required, protection and/or deprotection of functional moiety may be carried out.

The above-described thiazole ring formation reaction is known, and is carried out, for example, in water or an organic solvent (e.g., alcohols such as methanol, ethanol, propanol, isopropanol, etc., dimethylformamide, dimethylsulfoxide, acetonitrile, dichloroethane, dimethoxyethane, toluene, tetrahydrofuran, 1,4-dioxane, etc.: These solvents are used separately or are used by mixture of two or more in just proportion (for example, by a ratio of 1:1~1:10, etc.), if required.) or in the absence of solvent, in the presence or absence of a base (e.g., a hydroxide of alkali metal (e.g., potassium hydroxide, sodium hydroxide, cesium hydroxide, etc.), a carbonate (e.g., potassium carbonate, cesium carbonate, sodium carbonate, sodium hydrogen carbonate, etc.), or its aqueous solution, or a mixture thereof), with or without ultrasonic irradiation at a temperature of about −78° C. to about 100° C.

Though it is easily understood by those skilled in the art, in the case that the compounds represented by general formula (I-1) or general formula (I-2) of the present invention and the compounds represented by general formula (1), (2) or (3) used as starting materials contain a hydroxy group, carboxy group, amino group, or mercapto group, such compounds can be prepared by subjecting to a reactions of above-described ring formation reaction after appropriate protection of said group in advance, and then removing the protecting group.

As the amino-protecting group, there are exemplified benzyloxycarbonyl group, tert-butoxycarbonyl group, allyloxycarbonyl (Alloc) group, 1-methyl-1-(4-biphenyl)ethoxycarbonyl (Bpoc) group, trifluoroacetyl group, 9-fluorenylmethoxycarbonyl group, benzyl (Bn) group, p-methoxybenzyl group, benzyloxymethyl (BOM) group, 2-(trimethylsilyl)ethoxymethyl (SEM) group, and so forth.

As the hydroxy-protecting group, there are exemplified methyl group, trityl group, methoxymethyl (MOM) group, 1-ethoxyethyl (EE) group, methoxyethoxymethyl (MEM) group, 2-tetrahydropyranyl (THP) group, trimethylsilyl (TMS) group, triethylsilyl (TES) group, tert-butyldimethylsilyl (TBDMS) group, tert-butyldiphenylsilyl (TBDPS) group, acetyl (Ac) group, pivaloyl group, benzoyl group, benzyl (Bn) group, p-methoxybenzyl group, allyloxycarbonyl (Alloc) group, and 2,2,2-trichloroethoxycarbonyl (Troc) group, and so forth.

As the mercapto-protecting group, there are exemplified benzyl group, methoxybenzyl group, methoxymethyl (MOM) group, 2-tetrahydropyranyl (THP) group, diphenylmethyl group, acetyl (Ac) group, and so forth.

As the carboxyl-protecting group, there are exemplified methyl group, ethyl group, tert-butyl group, allyl group, phenacyl group, benzyl group, and so forth.

In addition to the above protecting groups for amino, hydroxy, mercapto, or carboxyl groups, there is no particular limitation so long as it can be easily and selectively removed. For example, protecting groups described in Protective Groups in Organic Synthesis (T. W. Greene, John Wiley & Sons Inc., 1999) also can be used.

The protection method for carboxy, hydroxy, amino, and mercapto group is well known. For example, it is described in Protective Groups in Organic Synthesis (T. W. Greene, John Wiley & Sons Inc., 1999).

The deprotection method for the protecting group of carboxy, hydroxy, amino, and mercapto group is well known. For example, it is described in Protective Groups in Organic Synthesis (T. W. Greene, John Wiley & Sons Inc., 1999).

Examples of such deprotection are (1) alkali hydrolysis
(2) deprotection under acidic conditions
(3) deprotection by hydrogenolysis
(4) deprotection using a metal complex
(5) deprotection using a metal, and
(6) deprotection of silyl groups.

Details of these deprotection methods are hereinafter illustrated.

(1) Deprotection by alkali hydrolysis such as deprotection of trifluoroacetyl group is performed in an organic solvent (e.g., methanol, tetrahydrofuran, 1,4-dioxane, etc.) at about 0° C. to about 40° C., using an alkali hydroxide (e.g., sodium hydroxide, potassium hydroxide, lithium hydroxide, etc.), an alkaline earth metal hydroxide (e.g., barium hydroxide, calcium hydroxide, etc.) or a carbonate (e.g., sodium carbonate, potassium carbonate, etc.) or an aqueous solution thereof or a mixture thereof.

(2) The deprotection under acidic conditions such as deprotection of tert-butoxycarbonyl, trityl, and so forth is carried out at about 0° C. to about 100° C. with an organic acid (e.g., acetic acid, trifluoroacetic acid, methanesulfonic acid, etc.) or an inorganic acid (e.g., hydrochloric acid, sulfuric acid, etc.) or a mixture thereof (e.g., hydrogen bromide/acetic acid) in water or an organic solvent (e.g., dichloromethane, chloroform, 1,4-dioxane, ethyl acetate, anisole, etc.).

(3) The deprotection by hydrogenolysis such as deprotection of benzyl, benzhydryl, benzyloxycarbonyl, allyloxycarbonyl, and so forth is carried out at about 0° C. to about 200° C. in a solvent [ethers (e.g., tetrahydrofuran, 1,4-dioxane, dimethoxyethane, diethyl ether, etc.), alcohols (e.g., methanol, ethanol, etc.), benzenes (e.g., benzene, toluene, etc.), ketones (e.g., acetone, methyl ethyl ketone, etc.), nitriles (e.g., acetonitrile, etc.), amides (e.g., N,N-dimethylformamide, etc.), water, ethyl acetate, acetic acid or a mixture of two or more solvents thereof in the presence of a catalyst (e.g., palladium-carbon, palladium black, palladium hydroxide, platinum oxide, Raney-Ni, etc.) under a normal pressure or an increased pressure in a hydrogen stream or in the presence of ammonium formate.

(4) The deprotection using a metal, such as deprotection of allyloxycarbonyl group or the like, is performed at about 0° C. to about 40° C. in an organic solvent (e.g., dichloromethane, N,N-dimethylformamide, tetrahydrofuran, ethyl acetate, acetonitrile, 1,4-dioxane, ethanol, etc.), water or a mixture thereof in the presence of a trapping reagent (e.g., tributyltin hydride, triethylsilane, dimedone, morpholine, diethylamine, pyrrolidine, etc.), an organic acid (e.g., acetic acid, formic acid, 2-ethylhexanoic acid, etc.) and/or an organic acid salt (e.g., sodium 2-ethylhexanoate, potassium 2-ethylhexanoate, etc.) and in the presence or absence of a phosphine reagent (e.g., triphenylphosphine, etc.), using a metal complex [e.g., tetrakistriphenylphosphine palladium(0), bis(triphenylphosphine)palladium(II) dichloride, palladium(II) acetate, tris(triphenylphosphine)rhodium(I)].

(5) The deprotection using a metal is performed in an acidic solvent (e.g., acetic acid, a buffer of pH 4.2 to 7.2, or a mixture thereof and an organic solvent such as tetrahydrofuran) in the presence of a zinc dust at about 0° C. to about 40° C. while applying ultrasonic waves, if required.

(6) The deprotection of the silyl group is carried out in a water-miscible organic solvent (e.g., tetrahydrofuran, acetonitrile, etc.) using tetrabutylammonium fluoride at about 0° C. to about 40° C.

Those skilled in the art can easily understand that the desired compounds of the present invention can be easily produced by selectively employing these deprotection methods. If necessary, conversion into desired non-toxic salts may be followed according to the known method.

(B) Among the compounds represented by general formula (I) of the present invention, a compound wherein ring A represents an oxazole ring, that is, a compound represented by general formula (I-3):

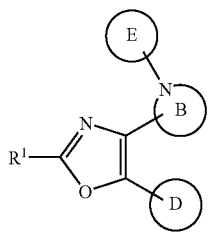

(I-3)

wherein all symbols have the same meanings as described above or a compound represented by general formula (I-4):

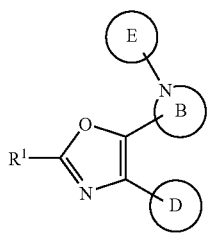

(I-4)

wherein all symbols have the same meanings as described above can be prepared by subjecting an above-described compound represented by general formula (1) or (2) and a compound represented by general formula (4):

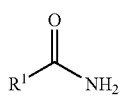

(4)

wherein $R^1$ has the same meaning as described above to a ring formation reaction. If required, protection and/or deprotection of functional moiety may be carried out.

This oxazole ring formation reaction can be carried out in the same manner as above-described thiazole ring formation reaction. Also, protection and/or deprotection of functional moiety may be carried out in the same manner as described above.

(C) Among the compounds represented by general formula (I) of the present invention, a compound wherein ring A represents a thiophene ring, that is, a compound represented by general formula (I-5):

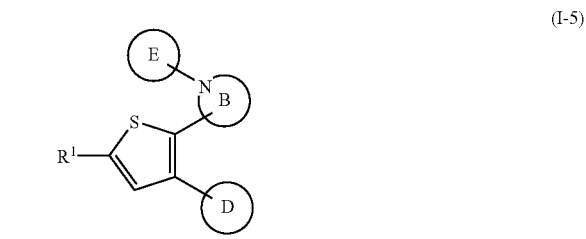

(I-5)

wherein all symbols have the same meanings as described above or a compound represented by general formula (I-6):

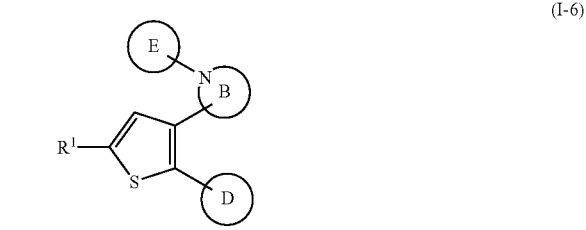

(I-6)

wherein all symbols have the same meanings as described above can be prepared by subjecting a compound represented by general formula (5):

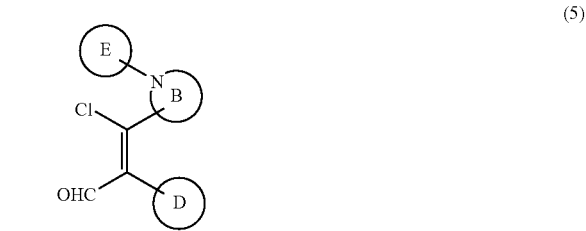

(5)

wherein all symbols have the same meanings as described above or a compound represented by general formula (6):

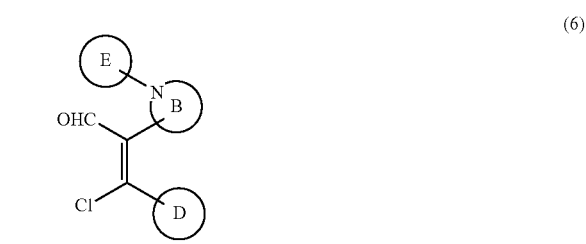

(6)

wherein all symbols have the same meanings as described above and a compound represented by general formula (7):

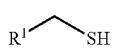
(7)

wherein R¹ has the same meaning as described above to a ring formation reaction. If required, protection and/or deprotection of functional moiety may be carried out.

The above-described thiophene ring formation reaction is known and is carried out, for example, in an organic solvent (e.g., alcohols such as methanol, ethanol, propanol, tert-butanol, etc., pyridine, etc.) in the presence of a base (e.g., sodium methoxide, sodium ethoxide, potassium tert-butoxide, triethylamine, diisopropylamine, etc.) at a temperature of about 0° C. to about 100° C.

Also, protection and/or deprotection of functional moiety may be carried out in the same manner as described above.

(D) Among the compounds represented by general formula (I) of the present invention, a compound wherein ring A represents a furan ring, that is, a compound represented by general formula (I-7):

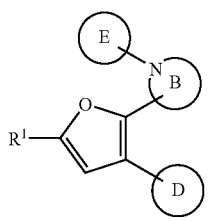
(I-7)

wherein all symbols have the same meanings as described above or a compound represented by general formula (I-8):

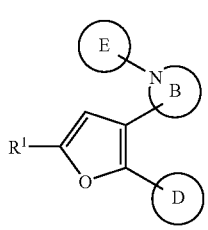
(I-8)

wherein all symbols have the same meanings as described above can be prepared by subjecting a compound represented by general formula (8):

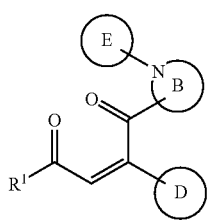
(8)

wherein all symbols have the same meanings as described above or a compound represented by general formula (9):

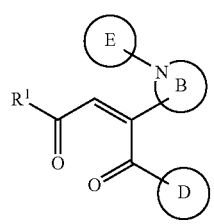
(9)

wherein all symbols have the same meanings as described above to a ring formation reaction. If required, protection and/or deprotection of functional moiety may be carried out.

The above-described furan ring formation reaction is known and is carried out, for example, in an organic solvent (e.g., polyethylene glycol 200, polyethylene glycol 400, ethanol, diethyleneglycol, triethyleneglycol, tetraethyleneglycol, etc.) in the presence of an organic acid (e.g., formic acid, etc.) and a catalyst (e.g., palladium-carbon/concentrated sulfuric acid, concentrated hydrochloric acid, etc.) at a temperature of about −78° C. to about 100° C.

Also, this furan ring formation reaction can be carried out in the same manner as described in *J. Org. Chem.*, 68(13), 5392, (2003).

Also, protection and/or deprotection of functional moiety may be carried out in the same manner as described above.

(E) Among the compounds represented by general formula (I) of the present invention, a compound wherein ring A represents a imidazole ring, that is, a compound represented by general formula (I-9):

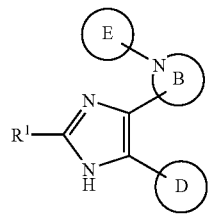
(I-9)

wherein all symbols have the same meanings as described above can be prepared by subjecting a compound represented by general formula (10):

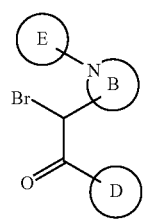
(10)

wherein all symbols have the same meanings as described above or a compound represented by general formula (11):

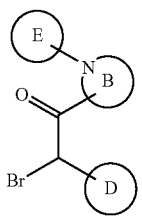

(11)

wherein all symbols have the same meanings as described above and a compound represented by general formula (12):

(12)

wherein $R^1$ has the same meaning as described above to a ring formation reaction. If required, protection and/or deprotection of functional moiety may be carried out.

The above-described imidazole ring formation reaction is known and is carried out, for example, in an organic solvent (e.g., formic acid, acetic acid, etc.) in the presence of ammonium base (e.g., ammonium formate, ammonium acetate, etc.) and copper reagent (e.g., copper acetate ($Cu(OAc)_2$), etc.) at a temperature of about 0° C. to about 100° C., after an reaction, for example, in water or an organic solvent (e.g., alcohols such as methanol, ethanol, propanol, etc., or a mixture thereof, etc.) in the presence of a base (e.g., sodium methoxide, sodium ethoxide, etc.) at a temperature of about 0° C. to about 100° C.

Also, this imidazole ring formation reaction can be carried out in the same manner as described in Bioorg. Med. Chem. Lett., 14(4), 919, (2004)

Also, protection and/or deprotection of functional moiety may be carried out in the same manner as described above.

(F) Among the compounds represented by general formula (I) of the present invention, a compound wherein ring A represents a imidazole ring, that is, an above-described compound represented by general formula (I-9) can be prepared by subjecting a compound represented by general formula (13):

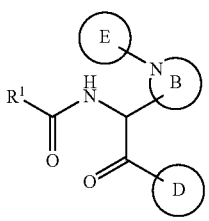

(13)

wherein all symbols have the same meanings as described above or a compound represented by general formula (14):

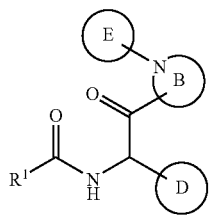

(14)

wherein all symbols have the same meanings as described above to a ring formation reaction. If required, protection and/or deprotection of functional moiety may be carried out.

The above-described imidazole ring formation reaction is known and is carried out, for example, in an organic solvent (e.g., halogenated hydrocarbons such as methylene chloride, etc., dimethylsulfoxide, dimethylformamide, acetic acid, formic acid, xylene, etc.) in the presence of an ammonium salt (e.g., ammonium acetate, ammonium formate, ammonium trifluoroacetate, etc.) and p-toluenesulfonic acid at a temperature of about −78° C. to about 150° C.

Also, this imidazole ring formation reaction can be carried out in the same manner as described in Tetrahedron Lett., 39(49), 8939, (1998).

Also, protection and/or deprotection of functional moiety may be carried out in the same manner as described above.

(G) The compounds represented by general formula (I) of the present invention can be prepared by subjecting a compound represented by general formula (15):

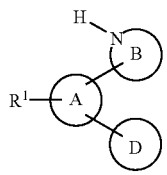

(15)

wherein all symbols have the same meanings as described above and a compound represented by general formula (16):

(16)

wherein X represents a halogen atom or —$B(OH)_2$, and ring E has the same meaning as described above to a reaction. If required, protection and/or deprotection of functional moiety may be carried out.

The above-described reaction for the case when X represents a halogen atom is known and is carried out, for example, in an organic solvent (e.g., dimethylsulfoxide, dimethylformamide, 1,4-dioxane, 1-methyl-2-pyrrolidinone, 1,3-dimethylimidazolidinone, etc.) in the presence of a base (e.g., a hydroxide of alkali metal such as potassium hydroxide, sodium hydroxide, cecium hydroxide, etc., or a carbonate such as potassium carbonate, cecium carbonate, sodium carbonate, sodium hydrogen carbonate, etc. or a mixture thereof, etc.) and copper reagent (e.g., copper iodide, copper chloride, copper cyamide, copper acetate, copper bromide, copper oxide, copper, etc.) at a temperature of about 0° C. to about 100° C.

The above-described reaction for the case when X represents —B(OH)$_2$ is known and is carried out, for example, in an organic solvent (e.g., dichloromethane, chloroform, dichloroethane, dimethylsulfoxide, dimethylformamide, etc.) in the presence of a base (e.g., pyridine, triethylamine, diisopropylamine, or a mixture thereof, etc.) and an organic metal reagent (e.g., tetrakis(triphenylphosphine)palladium Pd(PPh$_3$)$_4$), bis(triphenylphosphine)palladium dichloride (PdCl$_2$(PPh$_3$)$_2$), palladium acetate (Pd(OAc)$_2$), copper acetate (Cu(OAc)$_2$), etc.), in the presence or absence of a molecular sieves, at a temperature of about −20° C. to about 150° C.

Also, protection and/or deprotection of functional moiety may be carried out in the same manner as described above.

(H) Among the compounds represented by general formula (I) of the present invention, a compound wherein R$^1$ represents a piperidinyl group (piperidin-4-yl, piperidin-3-yl or piperidin-2-yl), and 1-position of the piperidinyl group is substituted by a substituent, that is, a compound represented by general formula (I-10):

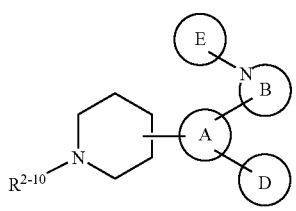

(I-10)

wherein R$^{2-10}$ represents an above-described substituent of R$^2$, and other symbols have the same meanings as described above can be prepared by subjecting a compound prepared by any of the above method (A) to (F) represented by general formula (I-11):

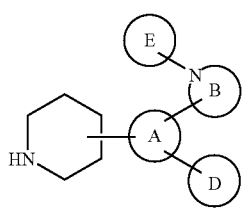

(I-11)

wherein all symbols have the same meanings as described above and a compound represented by general formula (17):

(17)

wherein Y represents a halogen atom, and R$^{2-10}$ has the same meaning as described above to an alkylation reaction. If required, protection and/or deprotection of functional moiety may be carried out.

The above-described alkylation reaction is known and is carried out, for example, in an organic solvent (e.g., acetone, acetonitrile, dimethylformamide, dimethylsulfoxide, 1,4-dioxane, etc.) in the presence or absence of a base (e.g., a hydroxide of alkali metal such as potassium hydroxide, sodium hydroxide, cecium hydroxide, etc., a carbonate such as potassium carbonate, cecium carbonate, sodium carbonate, sodium hydrogen carbonate, etc., its aqueous solution, or a mixture thereof, etc.) at a temperature of about −78° C. to about 100° C.

Also, protection and/or deprotection of functional moiety may be carried out in the same manner as described above.

(J) Among the compounds represented by general formula (I) of the present invention, a compound wherein R$^1$ represents a piperidinyl group, and 1-position of the piperidinyl group is substituted by a substituent via methylene, that is, a compound represented by general formula (I-12):

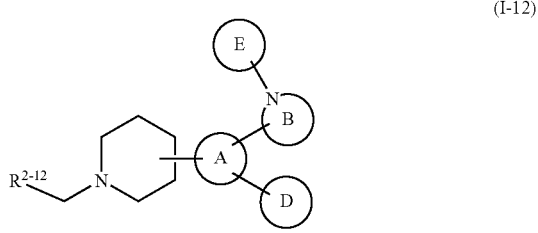

(I-12)

wherein R$^{2-12}$ represents a substituent which binds to piperidine via methylene, and other symbols have the same meanings as described above can be prepared by subjecting a compound represented by general formula (I-11) and a compound represented by general formula (18):

(18)

wherein R$^{2-12}$ has the same meaning as described above to a reductive amination reaction. If required, protection and/or deprotection of functional moiety may be carried out.

The above-described reductive amination reaction is known and is carried out, for example, in an organic solvent (e.g., dichloroethane, dichloromethane, dimethylformamide, acetic acid, a mixture thereof, etc.) in the presence of a reducer (e.g., sodium triacetoxyborohydride, sodium cyanoborohydride, sodium borohydride, etc.) at a temperature of about 0° C. to about 40° C.

Also, protection and/or deprotection of functional moiety may be carried out in the same manner as described above.

The compounds represented by general formula (1) to (18) as the starting material or the reagent to be used are known per se, or can be easily produced by the known method, for example, the method described in Comprehensive Organic Transformations: A Guide to Functional Group Preparations, 2nd Edition (Richard C. Larock, John Wiley & Sons Inc, 1999), or a combination method thereof.

In each reaction of the present invention, a reagent appropriately carried on a solid carrier of polymers (e.g., polystyrene, polyacrylamide, polypropylene, polyethylene glycol, etc.) may be used.

The end products of the present invention can be purified by the conventional purification means such as distillation under normal pressure or reduced pressure, high performance liquid chromatography with silica gel or magnesium silicate, thin layer chromatography, or column chromatography, or washing or recrystallization. Such purification may be carried out in each reaction or may be performed after several reactions.

The heating reaction in each reaction of the present invention may be performed using a water bath, an oil bath, a sand bath or a microwave, though it is apparent to those skilled in the art.

[Pharmacological Activity of the Compounds of the Present Invention]

Except for the pharmacological test described in Examples, there are exemplified the following methods to prove the pharmacological activity of the compounds of the present invention. p38 MAP kinase inhibitory activity of the compounds of the present invention can be proven by these methods.

(a) Study on p38α Map Kinase Inhibitory Activity

Using activation transcription factor 2 (activating transcription factor 2; ATF-2, Cell Signaling Inc., #9224L) which is a substrate of p38α MAP kinase, the inhibitory effect of the compound of the present invention on the ATF-2 phosphorylation by recombinant human p38α MAP kinase (Upstate Biotechnology Inc., #14-251) was studied by the Western-blotting method using the anti-phosphorylated ATF-2 antibody (Cell Signaling Inc., #9221L). In other words, 10 µL of a solution of the compound of the present invention at a known concentration is added to 10 µL of the kinase buffer (Cell Signaling Inc., #9802) containing recombinant human p38α MAP kinase (100 ng/tube) and pre-incubated for 10 minutes at 30° C. Then, 20 µL of adenosine triphosphate (ATP)/ATF-2 mixture is added, and after the incubation of 30 minutes at 30° C., 20 µL of SDS buffer (187.5 mM Tris/6% SDS/30% glycerol/150 mM DTT/0.03% bromophenol blue) is added to stop the enzyme reaction. After heating at 100° C. for 5 minutes, mixing and centrifugation are performed. After remixing, 20 µL of the sample is subjected to an electrophoresis on SDS-PAGE gel (10 to 20%, Daiichi Pure Chemicals Co., Ltd.). After the electrophoresis, blotting is performed on PVDF membrane (Sequi-Blot (proprietary name), 0.2 µm, BIO-RAD) by a conventional method. After that, the PVDF membrane is treated with Block Ace (Snow Brand Milk Products Co., Ltd.) (at room temperature, for 1 hour). After reacted with the anti-phosphorylated ATF-2 antibody for 1.5 hours, the membrane is washed with TBS-T solution (0.02 M Tris/0.137 M NaCl/0.05% Tween 20, pH 7.6). Furthermore, the reaction with a secondary antibody (anti-rabbit IgG, horse-radish peroxide linked whole antibody, Amersham LIFE SCIENCE) is carried out for 1 hour. After washing with TBS-T solution, phosphorylated ATF-2 is detected using Western blotting detection reagent (Amersham Pharmacia Biotech).

(b) Mouse Cytokine-producing Model

By the method shown below, the in vivo effect of the compounds of the present invention can be proven. The vehicle used for administering the compound of the present invention can be any vehicle so long as it is safe and is able to suspend or dissolve into an orally administrable form. For example, such medium includes methylcellulose, carboxymethylcellulose, hydroxypropylcellulose, hydroxypropylmethylcellulose, propylene glycol, polyethylene glycol, sugar, sugar alcohol, edible oil, distilled water, physiological saline, and a mixture thereof, all of which have been used for administering a compound to an animal by those skilled in the art.

[Experimental Method]

The compound of the present invention suspended or dissolved in 0.5% methylcellulose (MC) is orally administered to a male Balb/c mouse (Charles River Japan, Inc.), and after 0.5 hour, lipopolysaccharide (LPS, 055:B5, Difco) is intraperitoneally administered at the dose of 1 mg/kg (5 animals/group). MC (0.5%) is orally administered to a control group (5 animals). Ninety minutes after the LPS treatment, heparinized blood collection is performed via the abdominal main vein under anesthesia with ether, and blood plasma is obtained by centrifugation (12,000 rpm, 3 minutes, 4° C.). The obtained blood plasma sample is stored at −80° C. until it is used. TNF-α and IL-6 in the blood plasma are measured using ELISA kits from R&D Inc. (#MTA00) and Endogen Inc. (#EM2IL6), respectively.

[Toxicity]

Toxicity of the compound of the present invention is sufficiently low, and it was confirmed to be safe enough for use as pharmaceuticals.

Application for Pharmaceuticals

Since the compounds of the present invention suppress p38 MAP kinase activation in animals including human, particularly in human, they are expected to be useful in the prevention and/or the treatment of cytokine-mediated diseases such as various inflammatory diseases [for example, inflammation, dermatitis, atopic dermatitis, hepatitis, nephritis, glomerulonephritis, pancreatitis, psoriasis, gout, Addison's disease, arthritis (e.g., rheumatoid arthritis, osteoarthritis, rheumatoid spondylitis, gouty arthritis, synovitis, etc.), inflammatory ocular diseases, inflammatory pulmonary diseases (e.g., chronic pneumonia, silicosis, pulmonary sarcoidosis, pulmonary tuberculosis, adult respiratory distress syndrome (ARDS), severe acute respiratory syndrome (SARS), etc.), inflammatory bowel diseases (e.g., Crohn's disease, ulcerative colitis, etc.), allergic diseases (e.g., allergic dermatitis, allergic rhinitis, etc.), autoimmune disease, autoimmune hemolytic anemia, systemic lupus erythematosus, rheumatism, Castleman's disease, immune rejection accompanying transplantation (e.g., graft versus host reaction, etc.), and so forth], central nervous system disorders [for example, central neuropathy (e.g., cerebrovascular disease such as cerebral hemorrhage and cerebral infarction, head trauma, spinal cord injury, cerebral edema, multiple sclerosis, etc.), neurodegenerative disease (e.g., Alzheimer's disease, Parkinson's disease, amyotrophic lateral sclerosis (ALS), AIDS encephalopathy, etc.), meningitis, Creutzfeldt-Jakob syndrome, and so forth], respiratory diseases [for example, asthma, chronic obstructive pulmonary disease (COPD), and so forth], cardiovascular diseases [for example, angina, heart failure (e.g., congestive heart failure, acute heart failure, chronic heart failure, etc.), myocardial infarction (e.g., acute myocardial infarction, myocardial infarction prognosis, etc.), atrial myxoma, arteriosclerosis, hypertension, dialysis-induced hypotension, thrombosis, disseminated intravascular coagulation (DIC), reperfusion injury, restenosis after percutaneous transluminal coronary angioplasty (PTCA), and so forth], urinary diseases [for example, renal failure, and so forth], metabolic diseases or endocrine diseases [for example, diabetes, and so forth], bone diseases [for example, osteoporosis, and so forth], cancerous diseases [for example, malignant tumor (e.g., tumor growth and metastasis, etc.), multiple myeloma, plasma cell leukemia, carcinemia, and so forth], and infectious diseases [for example, viral infection (e.g., cytomegalovirus infection, influenza virus infection, herpes virus infection, corona virus infection, etc.), cachexia associated with infections, cachexia caused by acquired immune deficiency syndrome (AIDS), toxemia (e.g., sepsis, septic shock, endotoxin shock, gram negative bacterial sepsis, toxic shock syndrome, severe acute respiratory syndrome (SARS) accompanying virus infection, etc.), and so forth], and so on.

Among subtypes ($\alpha$, $\beta$, $\beta_2$, $\gamma$, $\delta$) of p38 MAP kinase, the compounds of the present invention include compounds selectively inhibiting subtype $\alpha$, and compounds inhibiting other subtypes other than subtype $\alpha$.

The compounds of the present invention can be usually administered systemically or topically in the form of oral or parenteral administration.

Since the compounds of the present invention are safe and have low toxicity, they can be administered to a human or a mammal other than humans (e.g., rat, mouse, rabbit, sheep, pig, cow, cat, dog, monkey, etc.).

Although the dose varies depending on age, body weight, symptom, therapeutic effect, administration route and treatment time, the dose for a human adult is generally within a range of about 1 mg to about 1000 mg per administration that is orally administered up to several times a day, or within a range of about 0.1 mg to about 100 mg per administration that is parenterally or preferably intravenously administered up to several times a day or intravenously administered over a period of continuous 1 to 24 hours a day.

As mentioned above, the dose to be prescribed depends upon various conditions, and thus there are cases in which doses lower than the range as specified above may be enough or doses greater than the range as specified above may be required.

In the administration of the compounds of the present invention, they are used as solid preparations or liquid preparations for oral administration, or as injections, external preparations or suppositories for parenteral administration.

In the production of these compositions, the compounds of the present invention are not limited to a substantially chemically pure single substance, they may contain impurities (for example, by-products derived from the production process, solvents, starting materials, or decomposition products) so long as such impurities are within an acceptable range as a pharmaceutical bulk.

The solid preparations for oral administration include tablets, pills, capsules, dispersible powders, granules, and so forth. The capsules include hard capsules and soft capsules.

In such solid preparations for oral use, one or more of the active compound(s) may be admixed solely or with diluents (e.g., lactose, mannitol, glucose, microcrystalline cellulose, starch, etc.), binders (e.g., hydroxypropylcellulose, polyvinylpyrrolidone, magnesium aluminometasilicate, etc.), disintegrators (e.g., cellulose calcium glycolate, etc.), lubricants (e.g., magnesium stearate, etc.), stabilizers, solubilizers (e.g., glutamic acid, aspartic acid, etc.), and then formulated into a preparation in the conventional manner. When necessary, such preparations may be coated with a coating agent (e.g., sucrose, gelatin, hydroxypropylcellulose, hydroxypropylmethyl cellulose phthalate, etc.) or they may be coated with two or more coating layers. Furthermore, the solid preparations for oral use include capsules of absorbable materials like gelatin.

The liquid preparations for oral administration include pharmaceutically acceptable aqueous solutions, suspensions, emulsions, syrups, elixirs, and so forth. In such preparations, one or more of the active compound(s) may be dissolved, suspended or emulsified in a commonly used diluent (e.g., purified water, ethanol or a mixture thereof, etc.). Besides such diluents, said compositions may also contain wetting agents (e.g., glycerin, propylene glycol, etc.), suspending agents (e.g., Carmellose, agar, gelatin, methylcellulose, etc.), emulsifiers (e.g., gum acacia, povidone, glyceryl monostearate, etc.), sweetening agents (e.g., fructose, glucose, etc.), flavouring agents (e.g., coffee, tea, cocoa, etc.), perfumes (e.g., orange oil, thymol, etc.), preservatives (e.g., benzoic acid, sodium benzoate, ethyl parahydroxybenzoate, propyl parahydroxybenzoate, etc.), and buffers (e.g., citric acid, disodium hydrogen phosphate, sodium citrate, sodium hydrogen carbonate, acetic acid, lactic acid, etc.), and so forth.

Injections for parenteral administration include any injection and also include instillation solutions. For example, such injections for parenteral administration include intramuscular injection, subcutaneous injection, intracutaneous injection, intraarterial injection, intravenous injection, intraperitoneal injection, intraspinally injection, and intravenous instillation.

Injections for parenteral administration include solutions, suspensions, emulsions, and solid injection which are dissolved or suspended in a solvent immediately before use. The injections are used by dissolving, suspending or emulsifying one or more of the active compound(s) in a diluent. Said diluents may contain distilled water for injection, physiological saline, vegetable oil, alcohol (e.g., propylene glycol, polyethylene glycol, ethanol, etc.), and a combination thereof. Further, the injections may contain stabilizers, solubilizers (e.g., glutamic acid, aspartic acid, polysorbate 80 (registered trade mark), etc.), suspending agents (e.g. methylcellulose, carboxymethylcellulose, etc.), emulsifiers (e.g., polysorbate 80, etc.), soothing agents (e.g., procaine, lidocaine hydrochloride, etc.), buffers (e.g., sodium hydrochloride, potassium hydrochloride, disodium hydrogen phosphate, citric acid, sodium citrate, etc.), preservatives (e.g., benzylalcohol, etc.), etc. The injections are sterilized in the final formulation step or prepared by sterile procedure. The injections may also be formulated into sterile solid preparation, for example, by freeze-drying, and may be used after sterilized or dissolved in sterile injectable water or other sterile diluent(s) immediately before use.

Other preparations for parenteral administration may contain one or more active compounds, and as such compositions, there are exemplified conventionally formulated external solutions, ointments, pastes, inhalations, sprays, suppositories, or vaginal pessaries.

Sprays may contain stabilizers such as sodium hydrogen sulfite, and buffers capable of imparting isotonicity, including isotonic agents such as sodium chloride, sodium citrate and citric acid.

The compounds of the present invention may be administered in combination with other drugs for the purpose of:
1) complement and/or enhancement of preventing and/or treating effect of the compound,
2) improvement of dynamics and absorption of the compound, and lowering of dose, and/or
3) alleviation of side effect of the compound.

Also, a combination of the compounds of the present invention may be administered as a combination drug for the purpose of:
1) complement and/or enhancement of preventing and/or treating effect of the other drugs,
2) improvement of dynamics and absorption of the other drugs, and lowering of dose, and/or
3) alleviation of side effect of the other drugs.

The compounds of the present invention may be administered in combination with other drugs as a preparation in one drug product comprising these components, or may be administered separately. When they are administered independently, they may be administered simultaneously or with time lag. Administration with time lag includes the method of administering first the compounds of the present invention and subsequently administering other drugs, and the method of administering first the other drug and subsequently administering the compound of the present invention, and they may be administered in the same route or not.

There is no limitation on the diseases on which the above combination drugs have a preventing and/or treatment effect, so long as the preventing and/or treatment effect of the compound of the present invention is complemented and/or enhanced in the disease.

The weight proportion of the compounds of the present invention and the other drugs is not specifically limited.

Arbitrary two or more of the other drugs may be administered in combination.

Examples of the other drugs for compensating for and/or enhancing the preventive and/or treatment effect of the compounds of the present invention include not only those which have so far been found but also those which will be found on the basis of the aforementioned mechanism.

Other agents to complement and/or enhance a prevention and/or a treatment effect of the compound of the present invention on rheumatoid arthritis, osteoarthritis, arthritis or the like include a steroidal agent, an elastase inhibitor, a cannabinoid-2 receptor stimulating agent, a prostaglandin, a prostaglandin synthase inhibitor, a phosphodiesterase inhibitor, a metalloproteinase inhibitor, an adhesion molecule inhibitor, an anti-cytokine protein preparation, a cytokine inhibitor, an immunomodulator, a disease modifying anti-rheumatic drug, a non-steroidal anti-inflammatory agent, c-Jun N-terminal kinase inhibitor, and so forth.

Other agents to complement and/or enhance prevention and/or treatment effect of the compound of the present invention on inflammatory bowel disease, Crohn's disease or ulcerative colitis include a steroidal agent, an elastase inhibitor, a cannabinoid-2 receptor stimulating agent, a prostaglandin, a prostaglandin synthase inhibitor, a phosphodiesterase inhibitor, a metalloproteinase inhibitor, an adhesion molecule inhibitor, an anti-cytokine protein preparation, a cytokine inhibitor, an immunomodulator, a leukotriene receptor antagonist, an anticholinergic agent, a 5-lipoxygenase inhibitor, a nitric monoxide synthase inhibitor, an interleukin-8 antagonist, a poly(ADP)-ribose polymerase inhibitor, a mitochondrial benzodiazepine receptor agonist, an anti-oxidation agent, a local anesthetic, an agent for digestive tract ulcer, a defense factor enhancing agent, mesalazine, salazosulfapyridine and so forth.

Other agents to complement and/or enhance prevention and/or treatment effect of the compound of the present invention on asthma, chronic pulmonary inflammatory diseases or adult respiratory distress syndrome (ARDS) include a steroidal agent, an elastase inhibitor, a cannabinoid-2 receptor stimulating agent, a prostaglandin, a prostaglandin synthase inhibitor, a phosphodiesterase inhibitor, a metalloproteinase inhibitor, an adhesion molecule inhibitor, a leukotriene receptor antagonist, an anticholinergic agent, a thromboxane A2 receptor antagonist, a thromboxane synthase inhibitor, a $\beta_2$ adrenergic receptor stimulating agent, a xanthine derivative, an expectorant agent, an antibiotic, an anti-histamine agent, an anti-cytokine protein preparation, a cytokine inhibitor, a forskolin preparation, a mediator release inhibitor, and so forth.

Examples of the steroidal agent include, for example, clobetasol propionate, diflorasone diacetate, fluocinonide, mometasone furoate, betamethasone dipropionate, betamethasone butyrate propionate, betamethasone valerate, difluprednate, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone acetate valerate, fluocinolone acetonide, beclomethasone dipropionate, triamcinolone acetonide, flumetasone pivalate, alclometasone dipropionate, clobetasone butyrate, prednisolone, fludroxycortide, cortisone acetate, hydrocortisone, hydrocortisone sodium phosphate, hydrocortisone sodium succinate, fludrocortisone acetate, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, dexamethasone sodium phosphate, dexamethasone palmitate, paramethason acetate, betamethasone, fluticasone propionate, budesonide, flunisolide, ST-126P, ciclesonide, dexamethasone palmitate, mometasone furoate, prasterone sulfonate, deflazacort, methylprednisolone suleptanate, methylprednisolone sodium succinate, and so forth.

Examples of an elastase inhibitor include, for example, ONO-5046, ONO-6818, MR-889, PBI-1101, EPI-HNE-4, R-665, ZD-0892, ZD-8321, GW-311616, DMP-777, L-659286, L-658758, L-680833, L-683845, AE-3763, and so forth.

Examples of a prostaglandin (hereinafter abbreviated to PG) include, for example, PG receptor agonist, PG receptor antagonist, and so forth.

Examples of PG receptor include, for example, PGE receptor ($EP_1$, $EP_2$, $EP_3$, $EP_4$), PGD receptor (DP, $CRTH_2$), PGF receptor (FP), PGI receptor (IP), TX receptor (TP), and so forth.

Examples of a prostaglandin synthase inhibitor include, for example, salazosulfapyridine, mesalazine, olsalazine, 4-aminosalicylic acid, JTE-522, auranofin, carprofen, diphenpyramide, flunoxaprofen, flurbiprofen, indometacin, ketoprofen, lornoxicam, loxoprofen, meloxicam, oxaprozin, parsalmide, piproxen, piroxicam, piroxicam betadex, piroxicam cinnamate, tropine indometacinate, zaltoprofen, pranoprofen, and so forth.

Examples of a cannabinoid-2 receptor stimulating agent include, for example, N-arachidonoylethanolamine (anandamide), 2-arachidonoylglycerol (2-AG), and so forth.

Examples of a phosphodiesterase inhibitor include, for example, PDE4 inhibitor such as rolipram, cilomilast (proprietary name: Ariflo), Bay19-8004, NIK-616, roflumilast (BY-217), cipamfylline (BRL-61063), atizoram (CP-80633), SCH-351591, YM-976, V-11294A, PD-168787, D-4396, and IC-485, and a PDE5 inhibitor such as sildenafil, and so forth.

Examples of a metalloproteinase inhibitor include, for example, BB94, ONO-4817, and so forth.

Examples of an adhesion molecule inhibitor include, for example, an antagonist for α-4-integrin, and so forth.

Examples of an anticytokine protein preparation include, for example, an anti-TNF-α preparations, an anti-IL-1 preparations, an anti-IL-6 preparations, and so forth.

Examples of an anti-TNF-α preparations include a preparation containing an anti-TNF-α antibody, a soluble TNF-α receptor, an anti-TNF-α receptor antibody or a protein bound to a soluble TNF-α, such as a preparation containing infliximab or etanercept, or the like.

Examples of the anti-IL-1 preparations include a preparation containing an anti-IL-1 antibody, a soluble IL-1 receptor, IL-1Ra or an anti-IL-1 receptor antibody, such as a preparation containing anakinra or the like.

Examples of the anti-IL-6 preparations include a preparation containing an anti-IL-6 antibody, a soluble IL-6 receptor or an anti-IL-6 receptor antibody, such as a preparation containing MRA or the like.

Examples of an immunomodulator include, for example, methotrexate, cyclosporine, ascomycin, leflunomide, bucillamine, salazosulfapyridine, azathioprine, tacrolimus, cyclophosphamide, and so forth.

Examples of a disease modifying anti-rheumatic drug include, for example, gold thioglucose, sodium aurothiomalate, auranofin, chloroquine, actarit, D-penicillamine preparation, lobenzarit disodium, bucillamine, hydroxychloroquine, salazosulfapyridine, and so forth.

Examples of a non-steroidal anti-inflammatory agents include, for example, sasapyrine, sodium salicylate, aspirin, aspirin/dialuminate composition, diflunisal, indomethacin, suprofen, ufenamate, dimethyl isopropylazulene, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofenaxetil, ketoprofen, fenoprofen calcium, thiaprofen, oxaprozin, pranoprofen, loxoprofen sodium, alminoprofen, zaltoprofen, mefenamic acid, aluminum mefenamate, tolfenamic acid, floctafenine, ketophenylbutazon, oxyphenbutasone, piroxicam, tenoxicam, ampiroxicam, Napageln ointment, epirizole, tiaramide hydrochloride, tinoridine hydrochloride, emorfazone, sulpyrine, migrenin, Saridon, Sedes G, Amipylo-N, Sorbon, pyrine preparation for cold syndrome, acetaminophen, phenacetin, dimetotiazine mesilate, simetride combinations, a non-pyrine cough and cold preparation, and so forth.

Examples of a leukotriene receptor antagonist include, for example, pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057, and so forth.

Examples of an anti-cholinergic agents include, for example, ipratropium bromide, oxitropium bromide, flutropium bromide, cimetropium bromide, temiverine, tiotropium bromide, revatropate (UK-112166), and so forth.

Examples of a topical anesthetics include, for example, cocaine hydrochloride, procaine hydrochloride, lidocaine, dibucaine hydrochloride, tetracaine hydrochloride, and so forth.

Examples of a defense factor enhancing agents include sucralfate, aldioxa, teprenone, cetraxate hydrochloride, ornoprostil, and so forth.

Examples of a thromboxane $A_2$ receptor antagonist include, for example, seratrodast, ramatroban, domitroban calcium hydrate, KT-2-962, and so forth.

Examples of a thromboxane synthase inhibitor include ozagrel hydrochloride, imitrodast sodium, and so forth.

Examples of a $\beta_2$ adrenergic receptor stimulating agent include, for example, fenoterol hydrobromide, salbutamol sulfate, terbutaline sulfate, formoterol fumarate, salmeterol xinafoate, isoproterenol sulfate, orciprenaline sulfate, chlorprenaline sulfate, epinephrine, trimetoquinol hydrochloride, hexoprenalinemesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, R,R-formoterol, KUR-1246, KUL-7211, AR-C89855, S-1319, and so forth.

Examples of a xanthine derivative include, for example, aminophylline, theophylline, doxophylline, cipamfylline, diprophylline, and so forth.

Examples of a expectorant agent include, for example, foeniculated ammonia spirit, sodium hydrogen carbonate, bromhexine hydrochloride, carbocysteine, ambroxol hydrochloride, ambroxol hydrochloride sustained preparation, methylcysteine hydrochloride, acetylcysteine, L-ethylcysteine hydrochloride, tyloxapol, and so forth.

Examples of the antibiotic include, for example, cefuroxime sodium, meropenem trihydrate, netilmicin sulfate, sisomicin sulfate, ceftibuten, PA-1806, IB-367, tobramycin, PA-1420, doxorubicin, astromicin sulfate, cefetamet pivoxil hydrochloride, and so forth. Examples of the antibiotic as an inhalation include, for example, PA-1806, IB-367, tobramycin, PA-1420, doxorubicin, astromicin sulfate, cefetamet pivoxil hydrochloride, and so forth.

Examples of an anti-histamine agent include, for example, ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastine, and so forth.

Examples of the cytokine inhibitors include any one of non-protein preparations which can block the action of cytokines, containing a MAP kinase inhibitor, a gene regulating agent, a cytokine production inhibitor, a TNF-α converting enzyme inhibitor, an IL-1β converting enzyme inhibitor, an IL-6 antagonist, an IL-8 antagonist, a chemokine antagonist, a gene therapy agent, and an anti-sense compound, and so forth. The MAP kinase inhibitor includes, for example, PD-98059 and so forth. The gene regulating agent includes an inhibitor to molecules involved in signal transmission, such as NF-κB, IKK-1, IKK-2, and AP-1, and so forth. The cytokine production inhibitor includes, for example, suplatast tosilate (proprietary name: IPD), T-614, SR-31747, sonatimod, and so forth. The chemokine antgonist includes, for example, ONO-4128 and so forth. The gene therapy agent includes, for example, a gene therapy agent for accelerating expression of genes having antiinflammatory action, such as interleukin-4, interleukin-10, a soluble IL-1 receptor and a soluble TNF-α receptor, and so forth.

Examples of a mediator release inhibitor include, for example, tranilast, sodium cromoglicate, amlexanox, repirinast, ibudilast, tazanolast, pemirolast potassium, and so forth.

Examples of the c-Jun N-terminal kinase inhibitor include compounds described in WO 00/35906, WO 00/35909, WO 00/35921, WO 00/64872, WO 00/75118, and so forth.

Examples of an antioxidant, for example, vitamin E, edaravone, and so forth.

EXAMPLES

The present invention is explained below in detail based on Examples, but the present invention is not limited thereto.

In chromatographic separations and TLC, the solvents in parenthesis show the eluting and developing solvents and the ratios of the solvents used are by volume. As ammonia water, a commercially available 28% ammonia water was used.

Unless otherwise specified, $^1$H-NMR data was measured with heavy chloroform ($CDCl_3$).

Example 1 ethyl 1-(2,6-dichlorophenyl)-2-hydroxy-6-oxopiperidine-3-carboxylate

Under an atmosphere of nitrogen, to a solution of ethyl 5-[(2,6-dichlorophenyl)amino]-5-oxopentanoate (9.22 g, the compound described in Reference Example 1 of WO03/043988) in tetrahydrofuran (150 mL) were added a solution of lithium bis(trimethylsilyl)amide (1.6 mol/L) in tetrahydrofuran (56.8 mL) and ethyl formate (4.90 mL) at −78° C. and the mixture was stirred on ice bath for 2 hours and then at room temperature for 4 days. The reaction mixture was added by hydrochloric acid (1 mol/L) and ethyl acetate on ice bath, then the water layer was extracted with ethyl acetate. The obtained extract was dried with anhydrous sodium sulfate, filtrated and concentrated to give the title compound. The obtained compound was used in the following reaction without further purification.

Example 2 ethyl 1-(2,6-dichlorophenyl)-6-oxo-1,4,5,6-tetrahydropyridine-3-carboxylate

To a solution of the compound prepared in Example 1 in dichloromethane (150 mL) were added triethylamine (12.27 g) and methanesulfonyl chloride (6.65 g) on ice bath and the mixture was stirred at same temperature for 15 minutes. The reaction mixture was added by hydrochloric acid (1 mol/L), then the water layer was extracted with dichloromethane. The obtained extract was dried with anhydrous sodium sulfate and concentrated. The obtained residue was purified by column chromatography on silica gel (hexane:ethyl acetate=2:1) to give the title compound (4.00 g) having the following physical data.

TLC: Rf 0.42 (hexane:ethyl acetate=3:2); NMR: δ 1.30 (t, J=7.14 Hz, 3H), 2.71-2.86 (m, 4H), 4.22 (q, J=7.14 Hz, 2H), 7.07-7.16 (m, 1H), 7.27-7.36 (m, 1H), 7.40-7.48 (m, 2H).

Example 3 ethyl 1-(2,6-dichlorophenyl)-6-oxo-1,6-dihydropyridine-3-carboxylate

To a solution of the compound prepared in Example 2 (3.87 g) in benzene (80 mL) was added manganese dioxide (32.14 g) and the solution was refluxed for 8 hours. The reaction mixture was filtrated and concentrated. The obtained residue was purified by column chromatography on silica gel (hexane:diisopropyl ether=1:1) to give the title compound (2.34 g) having the following physical data.

TLC: Rf 0.60 (hexane:ethyl acetate=1:1); NMR: δ 1.36 (t, J=7.14 Hz, 3H), 4.34 (q, J=7.14 Hz, 2H), 6.69 (dd, J=9.52, 0.92 Hz, 1H), 7.34-7.44 (m, 1H), 7.48-7.56 (m, 2H), 7.91-8.04 (m, 2H).

Example 4

1-(2,6-dichlorophenyl)-6-oxo-1,6-dihydropyridine-3-carboxylic acid

To a solution of the compound prepared in Example 3 (2.34 g) in ethanol (30 mL) was added aqueous sodium hydroxide (1 mol/L) (15 mL) and the mixture was stirred at room temperature for 1.5 hours. The reaction mixture was concentrated. The obtained residue was added by hydrochloric acid (1 mol/L) and ethyl acetate, then the water layer was extracted with ethyl acetate. The obtained extract was dried with anhydrous sodium sulfate, filtrated and concentrated to give the title compound (2.13 g) having the following physical data.

TLC: Rf 0.28 (ethyl acetate); NMR: δ 6.72 (dd, J=9.70, 0.73 Hz, 1H), 7.35-7.45 (m, 1H), 7.48-7.56 (m, 2H), 7.99 (dd, J=9.70, 2.56 Hz, 1H), 8.03-8.08 (m, 1H).

Example 5

1-(2,6-dichlorophenyl)-6-oxo-1,6-dihydropyridine-3-carbonylchloride

To a solution of the compound prepared in Example 4 (330 mg) in dichloromethane (10 mL) were added oxalyl chloride (134 mg) and N,N-dimethylformamide (0.1 mL) and the mixture was stirred at room temperature for 30 minutes. The reaction mixture was concentrated to give the title compound. The obtained compound was used in the following reaction without further purification.

Example 6

5-[(2-chloro-4-fluorophenyl)acetyl]-1-(2,6-dichlorophenyl)pyridin-2(1H)-one

To a mixture of zinc powder (208 mg) and ethylene glycol dimethyl ether (10 mL) were added 1,2-dibromoethane (20 mg) and 2-chloro-4-fluorobenzyl bromide (473 mg) and the mixture was stirred at 75° C. for 1 hour. The compound prepared in Example 5 and tetrakis(triphenylphosphine)-palladium (123 mg) were added hereto and the reaction mixture was stirred at same temperature for 15 minutes. The reaction mixture was added by hydrochloric acid (1 mol/L) and ethyl acetate, then the water layer was extracted with ethyl acetate. The obtained extract was dried with anhydrous sodium sulfate and concentrated. The obtained residue was purified by column chromatography on silica gel (hexane:ethyl acetate=2:1) to give the title compound (171 mg) having the following physical data.

TLC: Rf 0.36 (hexane:ethyl acetate=3:2); NMR: δ 4.18 (s, 2H), 6.73 (dd, J=9.61, 0.82 Hz, 1H), 6.93-7.04 (m, 1H), 7.16 (dd, J=8.42, 2.56 Hz, 1H), 7.20-7.29 (m, 1H), 7.38-7.48 (m, 1H), 7.50-7.58 (m, 2H), 7.98-8.09 (m, 2H).

Example 7

5-[bromo(2-chloro-4-fluorophenyl)acetyl]-1-(2,6-dichlorophenyl)pyridin-2(1H)-one To a solution of the compound prepared in Example 6 (384 mg) in tetrahydrofuran (10 mL) was added phenyltrimethylammonium tribromide (351 mg) and the mixture was stirred at 60° C. for 1 hour. The solid separated out was filtrated and the filtrate was concentrated. The obtained residue was purified by column chromatography on silica gel (hexane:ethyl acetate=2:1) to give the title compound (413 mg) having the following physical data.

TLC: Rf 0.58 (hexane:ethyl acetate=1:1); NMR: δ 6.49 (s, 1H), 6.71 (d, J=9.79 Hz, 1H), 7.02-7.20 (m, 2H), 7.38-7.48 (m, 1H), 7.49-7.57 (m, 2H), 7.72 (dd, J=8.70, 5.77 Hz, 1H), 7.98 (dd, J=9.79, 2.65 Hz, 1H), 8.01-8.06 (m, 1H).

Example 8 tert-butyl 4-{5-(2-chloro-4-fluorophenyl)-4-[1-(2,6-dichlorophenyl)-6-oxo-1,6-dihydropyridin-3-yl]-1,3-thiazol-2-yl}piperidine-1-carboxylate To a solution of the compound prepared in Example 7 (413 mg) and tert-butyl 4-(aminocarbonothioyl)piperidine-1-carboxylate (206 mg) in isopropanol (10 mL) was added potassium carbonate (350 mg) and the mixture was stirred at 70° C. for 2 hours. The reaction mixture was filtrated and the filtrate was concentrated. The obtained residue was added by ethyl acetate and water, then the water layer was extracted with ethyl acetate. The obtained organic layer was dried with anhydrous sodium sulfate and concentrated. The obtained residue was purified by column chromatography on silica gel (hexane:ethyl acetate=1:1) to give the title compound (419 mg) having the following physical data.

TLC: Rf 0.35 (hexane:ethyl acetate=2:3); NMR: δ 1.47 (s, 9H), 1.67-1.87 (m, 2H), 2.07-2.20 (m, J=6.00, 3.00 Hz, 2H), 2.79-2.99 (m, 2H), 3.07-3.22 (m, 1H), 4.15-4.29 (m, 2H), 6.58 (d, J=9.70 Hz, 1H), 6.98-7.09 (m, 1H), 7.19-7.40 (m, 4H), 7.41-7.49 (m, 3H).

Example 9

5-[5-(2-chloro-4-fluorophenyl)-2-piperidin-4-yl-1,3-thiazol-4-yl]-1-(2,6-dichlorophenyl)pyridin-2(1H)-one

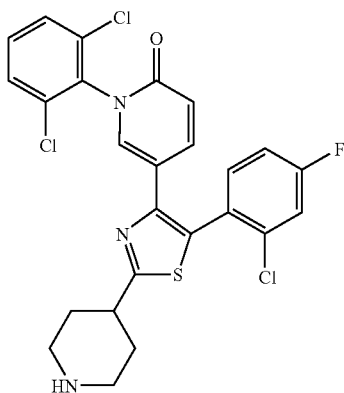

To a solution of the compound prepared in Example 8 (414 mg) in ethyl acetate (10 mL) was added 4 mol/L hydrogen chloride/ethyl acetate (5 mL) and the mixture was stirred at room temperature for 12 hours. The reaction mixture was filtrated and dried to give the compound of the present invention (370 mg) having the following physical data.

TLC: Rf 0.64 (chloroform:methanol:triethylamine=30:10:1); NMR: δ 1.98-2.23 (m, 2H), 2.33-2.49 (m, J=5.00, 4.00 Hz, 2H), 3.12-3.27 (m, 2H), 3.38-3.62 (m, 3H), 6.63 (dd, J=9.70, 0.73 Hz, 1H), 7.12-7.23 (m, 1H), 7.31 (dd, J=2.56, 0.73 Hz, 1H), 7.38 (dd, J=8.60, 2.56 Hz, 1H), 7.44-7.62 (m, 4H), 7.72 (dd, J=9.70, 2.56 Hz, 1H).

Example 10

5-[5-(2-chloro-4-fluorophenyl)-2-(1-ethylpiperidin-4-yl)-1,3-thiazol-4-yl]-1-(2,6-dichlorophenyl)pyridin-2(1H)-one

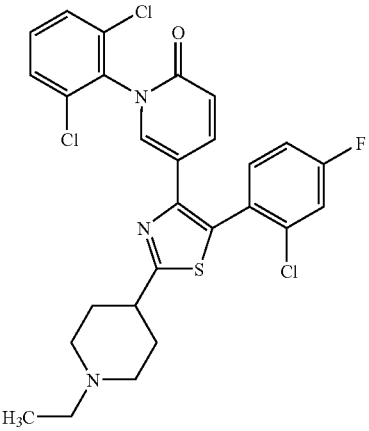

To a solution of the compound prepared in Example 9 (40 mg) in acetonitrile (1.5 mL) were added ethyl bromide (15 mg) and potassium carbonate (29 mg) and the mixture was stirred at 100° C. for 30 minutes. The reaction mixture was filtrated and the filtrate was concentrated. The obtained residue was purified by preparative TLC (chloromethane:methanol:triethylamine=120:20:1) to give the compound of the present invention (32 mg) having the following physical data.

TLC: Rf 0.61 (chloromethane:methanol:triethylamine=120:20:1); NMR: δ 1.07-1.18 (m, 3H), 1.85-2.26 (m, 6H), 2.40-2.55 (m, 2H), 2.92-3.15 (m, 3H), 6.58 (d, J=9.70 Hz, 1H), 6.99-7.07 (m, 1H), 7.23 (dd, J=8.51, 2.47 Hz, 1H), 7.29-7.48 (m, 6H).

Example 10(1)-Example 10 (3)

By the same procedure as a reaction of Example 10, using the corresponding halides instead of ethyl bromide, the compounds of the present invention having the following physical data were obtained.

Example 10(1)

5-[5-(2-chloro-4-fluorophenyl)-2-(1-isopropylpiperidin-4-yl)-1,3-thiazol-4-yl]-1-(2,6-dichlorophenyl)pyridin-2(1H)-one TLC: Rf 0.48 (chloromethane:methanol:triethylamine=120:20:1); NMR: δ 1.09 (d, J=6.59 Hz, 6H), 1.81-2.00 (m, 2H), 2.10-2.40 (m, 4H), 2.72-2.89 (m, 1H), 2.92-3.10 (m, 3H), 6.57 (d, J=9.70 Hz, 1H), 6.98-7.08 (m, 1H), 7.23 (dd, J=8.42, 2.56 Hz, 1H), 7.29-7.49 (m, 6H).

Example 10(2)

5-[5-(2-chloro-4-fluorophenyl)-2-(1-methylpiperidin-4-yl)-1,3-thiazol-4-yl]-1-(2,6-dichlorophenyl)pyridin-2(1H)-one TLC: Rf 0.45 (chloromethane:methanol:triethylamine=120:20:1); NMR: δ 1.83-2.01 (m, 2H), 2.04-2.22 (m, 4H), 2.33 (s, 3H), 2.89-3.06 (m, 3H), 6.58 (dd, J=9.70, 0.73 Hz, 1H), 6.98-7.08 (m, 1H), 7.23 (dd, J=8.33, 2.65 Hz, 1H), 7.27-7.49 (m, 6H).

Example 10(3)

5-(5-(2-chloro-4-fluorophenyl)-2-{1-[2-(dimethylamino)ethyl]piperidin-4-yl}-1,3-thiazol-4-yl)-1-(2,6-dichlorophenyl)pyridin-2(1H)-one TLC: Rf 0.46 (chloromethane:methanol:triethylamine=120:20:1); NMR: δ 1.82-2.02 (m, 2H), 2.06-2.21 (m, 4H), 2.26 (s, 6H), 2.40-2.58 (m, 4H), 2.91-3.12 (m, 3H), 6.57 (d, J=9.52 Hz, 1H), 6.98-7.09 (m, 1H), 7.19-7.41 (m, 4H), 7.41-7.49 (m, 3H).

Example 11

5-[(2,4-difluorophenyl)acetyl]-2H-pyran-2-one

By the same procedure as a series of reactions of Example 5 Example 6, using coumaric acid instead of the compound prepared in Example 4 used in the reaction of Example 5 and 2,4-difluorobenzyl bromide instead of 2-chloro-4-fluorobenzyl bromide used in the reaction of Example 6, the title compound having the following physical data was obtained.

TLC: Rf 0.36 (hexane:ethyl acetate=2:1); NMR: δ 8.41 (dd, J=2.7, 1.2 Hz, 1H), 7.87 (dd, J=9.9, 2.7 Hz, 1H), 7.20 (m, 1H), 6.94-6.82 (m, 2H), 6.39 (dd, J=9.9, 1.2 Hz, 1H), 4.03 (s, 2H).

Example 12

1-(2,6-difluorophenyl)-5-[(2,4-difluorophenyl)acetyl]pyridin-2(1H)-one

To a solution of the compound prepared in Example 11 (800 mg) in 2-propanol (15 mL) was added 2,6-difluoroaniline (1.0 mL) at room temperature and the mixture was stirred at 80° C. for 4.5 hours. The reaction mixture was poured into 1 mol/L hydrochloric acid, then extracted with ethyl acetate. The obtained organic layer was washed with 1 mol/L hydrochloric acid, an aqueous saturated sodium bicarbonate solution and brine sequentially, dried and concentrated. The obtained residue was purified by column chromatography on silica gel (hexane:ethyl acetate=6:1→3:1→3:2) to give the title compound (375 mg) having the following physical data.

TLC: Rf 0.51 (hexane:ethyl acetate=1:1); NMR: δ 8.12 (m, 1H), 8.02 (dd, J=9.9, 2.4 Hz, 1H), 7.50 (m, 1H), 7.27-7.08 (m, 3H), 6.92-6.80 (m, 2H), 6.71 (dd, J=9.9, 0.6 Hz, 1H), 4.07 (s, 2H).

Example 13

5-[bromo(2,4-difluorophenyl)acetyl]-1-(2,6-difluorophenyl)pyridin-2(1H)-one

By the same procedure as a reaction of Example 7, using the compound prepared in Example 12 instead of the compound prepared in Example 6, the title compound having the following physical data was obtained.

TLC: Rf 0.35 (hexane:ethyl acetate=2:1); NMR: δ 8.17 (d, J=2.7 Hz, 1H), 7.98 (dd, J=9.9, 2.7 Hz, 1H), 7.69 (m, 1H), 7.50 (m, 1H), 7.20-7.10 (m, 2H), 6.98 (m, 1H), 6.84 (m, 1H), 6.71 (d, J=9.9 Hz, 1H), 6.29 (s, 1H).

Example 14

1-(2,6-difluorophenyl)-5-[5-(2,4-difluorophenyl)-2-(4-piperidinyl)-1,3-thiazol-4-yl]-2(1H)-pyridinone

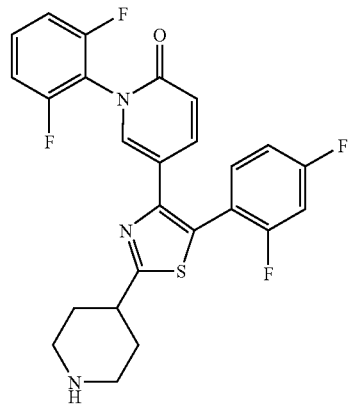

By the same procedure as a series of reactions of Example 8 Example 9, using the compound prepared in Example 13 instead of the compound prepared in Example 7, the compound of the present invention having the following physical data was obtained.

TLC: Rf 0.50 (dichloromethane:methanol:acetic acid=10:2:1); NMR: δ 7.56-7.29 (m, 4H), 7.12-6.89 (m, 4H), 6.58 (d, J=9.6 Hz, 1H), 3.30-3.06 (m, 3H), 2.83-2.75 (m, 2H), 2.21-2.08 (m, 2H), 2.00-1.60 (m, 2H), 1.80 (brs, 1H).

Example 15(1)-Example 15(2)

By the same procedure as a series of reactions of Example 12→Example 13→Example 14, using the corresponding aniline compounds instead of 2,6-difluoroaniline used in the reaction of Example 12, the compounds of the present invention having the following physical data were obtained.

Example 15(1)

5-[5-(2,4-difluorophenyl)-2-(piperidin-4-yl)-1,3-thiazol-4-yl]-1-(2,6-dimethylphenyl)pyridin-2(1H)-one TLC: Rf 0.29 (dichloromethane:methanol:acetic acid=10:2:1); NMR: δ 7.51 (dd, J=9.6, 2.7 Hz, 1H), 7.40-7.10 (m, 5H), 6.98-6.84 (m, 2H), 6.63 (d, J=9.6 Hz, 1H), 3.38-3.26 (m, 2H), 3.18 (m, 1H), 2.94-2.82 (m, 2H), 2.50 (brs, 1H), 2.30-2.20 (m, 2H), 2.04 (s, 6H), 2.06-1.86 (m, 2H).

Example 15(2)

5-[5-(2,4-difluorophenyl)-2-(piperidin-4-yl)-1,3-thiazol-4-yl]-1-(4-methoxy-2,6-dimethylphenyl)pyridin-2(1H)-one TLC: Rf 0.33 (ethyl acetate:methanol:triethylamine=1:2:1); NMR: δ 1.71-2.34 (m, 11H), 2.74-2.89 (m, 2H), 3.07-3.18 (m, 1H), 3.21-3.32 (m, 2H), 3.79 (s, 3H), 6.61 (d, J=9.5 Hz, 1H), 6.65 (s, 2H), 6.82-6.98 (m, 2H), 7.28-7.37 (m, 2H), 7.45-7.53 (m, 1H).

Example 16

1-(2,6-difluorophenyl)-5-[5-(2,4-difluorophenyl)-2-(1-methylpiperidin-4-yl)-1,3-thiazol-4-yl]pyridin-2(1H)-one

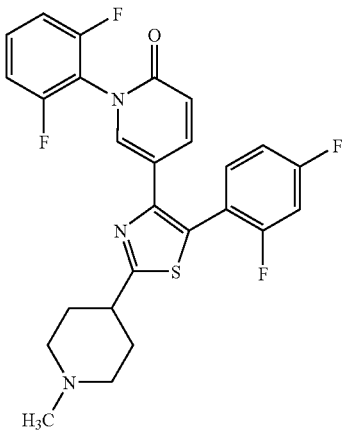

To a solution of the compound prepared in Example 14 (190 mg) in methanol (4 mL) were added 37% aqueous formaldehyde solution (64 mg) and sodium borohydride (30 mg) and the mixture was stirred at room temperature for 10 minutes. The reaction mixture was added by iced water, then extracted with ethyl acetate. The obtained organic layer was washed with brine, dried and concentrated to give the compound of the present invention (193 mg) having the following physical data.

TLC: Rf 0.57 (dichloromethane:methanol:water=80:20:1); NMR: δ 7.55-7.30 (m, 4H), 7.10-6.88 (m, 4H), 6.57 (dd, J=9.6, 0.6 Hz, 1H), 3.04-2.90 (m, 3H), 2.33 (s, 3H), 2.22-1.82 (m, 6H).

Example 16(1)-Example 16(2)

By the same procedure as a reaction of Example 16, using the compound prepared in Example 15(1)-Example 15(2) instead of the compound prepared in Example 14, the compounds having the following physical data were obtained.

Example 16(1)

5-[5-(2,4-difluorophenyl)-2-(1-methylpiperidin-4-yl)-1,3-thiazol-4-yl]-1-(2,6-dimethylphenyl)pyridin-2(1H)-one TLC: Rf 0.64 (dichloromethane:methanol:water=80:20:1); NMR: δ 7.51 (dd, J=9.6, 2.7 Hz, 1H), 7.40-7.10 (m, 5H), 6.98-6.84 (m, 2H), 6.62 (dd, J=9.6, 0.6 Hz, 1H), 3.04-2.90 (m, 3H), 2.33 (s, 3H), 2.20-1.80 (m, 6H), 2.04 (s, 6H).

Example 16(2)

5-[5-(2,4-difluorophenyl)-2-(1-methylpiperidin-4-yl)-1,3-thiazol-4-yl]-1-(4-methoxy-2,6-dimethylphenyl)pyridin-2(1H)-one TLC: Rf 0.51 (ethyl acetate:methanol:triethylamine=8:1:1); NMR: δ 1.76-2.04 (m, 8H), 2.05-2.24 (m, 4H), 2.34 (s, 3H), 2.90-3.07 (m, 3H), 3.79 (s, 3H), 6.61 (d, J=9.7 Hz, 1H), 6.65 (s, 2H), 6.82-6.98 (m, 2H), 7.27-7.38 (m, 2H), 7.44-7.53 (m, 1H).

Example 17

1-tert-butyl-4-{1-(2,4-difluorophenyl)-2-[1-(2,6-difluorophenyl)-6-oxo-1,6-dihydropyridin-3-yl]-2-oxoethyl}piperidine-1,4-dicarboxylate To a solution of the compound prepared in Example 13 (471 mg) in ethanol (20 mL) was added sodium N-Boc-isonipecotate (537 mg: prepared as follows; To a solution of N-Boc-isonipecotic acid (25 g) in tetrahydrofuran (150 mL) was added 5 N aqueous sodium hydroxide (21.8 mL) and the mixture was stirred at room temperature for 3 hours. The reaction mixture was concentrated, azeotropied with toluene, dried at 110° C. for 5 hours.) and the mixture was heated to reflux for 30 minutes. The reaction mixture was added by iced water, then extracted with ethyl acetate. The obtained organic layer was washed with brine, dried and concentrated. The obtained residue was purified by column chromatography on silica gel (hexane:ethyl acetate=4:1→3:1→2:1) to give the compound of the present invention (538 mg) having the following physical data.

TLC: Rf 0.50 (hexane:ethyl acetate=1:1); NMR: δ 8.13 (d, J=2.4 Hz, 1H), 7.88 (dd, J=9.9, 2.4 Hz, 1H), 7.54-7.39 (m, 2H), 7.15-7.09 (m, 2H), 7.00-6.85 (m, 2H), 6.82 (s, 1H), 6.66 (d, J=9.9 Hz, 1H), 4.10-3.90 (m, 2H), 3.00-2.80 (m, 2H), 2.63 (m, 1H), 2.05-1.82 (m, 2H), 1.80-1.60 (m, 2H), 1.45 (s, 9H).

Example 18

1-(2,6-difluorophenyl)-5-[5-(2,4-difluorophenyl)-2-(4-piperidinyl)-1,3-oxazol-4-yl]-2(1H)-pyridinone

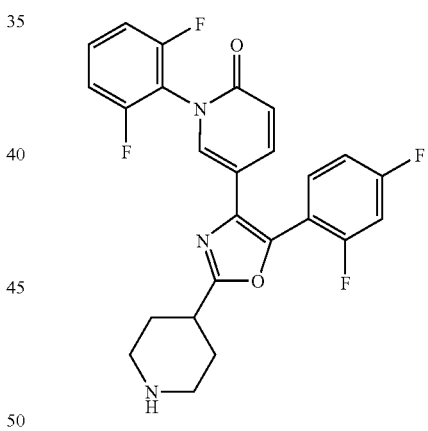

To a solution of the compound prepared in Example 17 (533 mg) in acetic acid (10 mL) was added ammonium acetate (1.05 g) and the mixture was heated to reflux at 100° C. for 1 hour. The reaction mixture was added by iced 5 N aqueous sodium hydroxide, then extracted with ethyl acetate. The obtained organic layer was washed with brine, dried and concentrated. The obtained residue was purified by column chromatography on silica gel (hexane:ethyl acetate=5:1→3:1→2:1→3:2) to give tert-butyl 4-{5-(2,4-difluorophenyl)-4-[1-(2,6-difluorophenyl)-6-oxo-1,6-dihydropyridin-3-yl]-1,3-oxazol-2-yl}piperidine-1-carboxylate (230 mg). To a solution of the obtained compound (220 mg) in methanol (0.5 mL) was added a solution of 4 N hydrogen chloride in ethyl acetate (5 mL) and the mixture was stirred at room temperature for 30 minutes. The reaction mixture was added by iced 5 N aqueous sodium hydroxide, then extracted with ethyl acetate. The obtained organic layer was washed with brine, dried and concentrated to give the compound of the present invention (170 mg) having the following physical data.

TLC: Rf 0.55 (dichloromethane:methanol:acetic acid=10: 2:1); NMR: δ 7.63 (m, 1H), 7.54-7.37 (m, 3H), 7.10-6.91 (m, 4H), 6.63 (dd, J=9.6, 0.6 Hz, 1H), 3.26-3.14 (m, 2H), 2.99 (m, 1H), 2.84-2.72 (m, 2H), 2.20-1.70 (m, 5H).

Example 19

1-(2,6-difluorophenyl)-5-[5-(2,4-difluorophenyl)-2-(1-methylpiperidin-4-yl)-1,3-oxazol-4-yl]pyridin-2(1H)-one

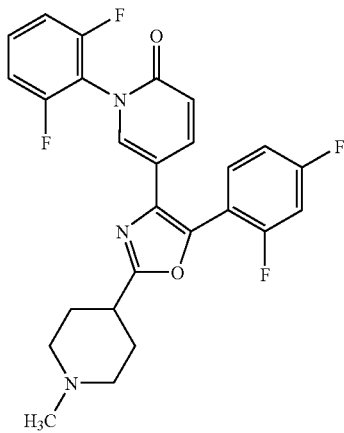

By the same procedure as a reaction of Example 16, using the compound prepared in Example 18 instead of the compound prepared in Example 14, the compound of the present invention having the following physical data was obtained.

TLC: Rf 0.65 (dichloromethane:methanol:water=80:20: 1); NMR: δ 7.62 (m, 1H), 7.54-7.37 (m, 3H), 7.14-6.90 (m, 4H), 6.63 (d, J=9.6 Hz, 1H), 3.00-2.75 (m, 3H), 2.33 (s, 3H), 2.25-1.90 (m, 6H).

Example 20(1)-Example 20(14)

By the same procedure as a series of reactions of Example 11→Example 12→Example 13→Example 17→Example 18, using the corresponding halides instead of 2,4-difluorobenzyl bromide used in the reaction of Example 11, the corresponding aniline compounds instead of 2,6-difluoroaniline used in the reaction of Example 12, and sodium salts of corresponding carboxylic acids instead of sodium N-Boc-isonipecotate used in the reaction of Example 17, the compounds of the present invention having the following physical data were obtained.

Example 20(1)

5-[5-(2,4-difluorophenyl)-2-(piperidin-4-yl)-1,3-oxazol-4-yl]-1-(2-fluorophenyl)pyridin-2(1H)-one TLC: Rf 0.56 (dichloromethane:methanol:acetic acid=10: 2:1); NMR: δ 7.72 (d, J=2.7 Hz, 1H), 7.54-7.20 (m, 6H), 7.06-6.91 (m, 2H), 6.61 (d, J=9.9 Hz, 1H), 3.23-3.17 (m, 2H), 2.98 (m, 1H), 2.82-2.73 (m, 2H), 2.20-1.60 (m, 5H).

Example 20(2)

5-[5-(2,4-difluorophenyl)-2-(piperidin-4-yl)-1,3-oxazol-4-yl]-1-(2,4,6-trifluorophenyl)pyridin-2(1H)-one TLC: Rf 0.34 (dichloromethane:methanol:triethylamine=40:10:1); NMR: δ 1.74-1.91 (m, 2H), 2.02-2.14 (m, 2H), 2.69-2.83 (m, 2H), 2.91-3.05 (m, 1H), 3.13-3.25 (m, 2H), 6.62 (d, J=9.7 Hz, 1H), 6.80-6.91 (m, 2H), 6.92-7.06 (m, 2H), 7.42-7.56 (m, 2H), 7.59 (d, J=2.4 Hz, 1H).

Example 20(3)

5-[5-(2,4-difluorophenyl)-2-(piperidin-4-yl)-1,3-oxazol-4-yl]-1-(2,3,6-trifluorophenyl)pyridin-2(1H)-one TLC: Rf 0.23 (ethyl acetate:methanol:triethylamine=6:3: 1); NMR: δ 1.79-1.99 (m, 3H), 2.05-2.17 (m, 2H), 2.74-2.86 (m, 2H), 2.94-3.06 (m, 1H), 3.17-3.28 (m, 2H), 6.64 (d, J=9.7 Hz, 1H), 6.92-7.09 (m, 3H), 7.23-7.35 (m, 1H), 7.42-7.56 (m, 2H), 7.60-7.64 (m, 1H).

Example 20(4)

5-[5-(2,4-difluorophenyl)-2-(piperidin-4-yl)-1,3-oxazol-4-yl]-1-(2-fluoro-6-methylphenyl)pyridin-2(1H)-one TLC: Rf 0.15 (dichloromethane:methanol:ammonia water=90:10:1); NMR: δ 2.11-2.25 (m, 5H), 2.25-2.37 (m, 2H), 2.97-3.20 (m, 3H), 3.31-3.45 (m, 2H), 6.65 (d, J=9.51 Hz, 1H), 6.89-7.16 (m, 4H), 7.27-7.37 (m, 1H), 7.42-7.57 (m, 3H).

Example 20(5)

1-(2-chloro-6-methylphenyl)-5-[5-(2,4-difluorophenyl)-2-(piperidin-4-yl)-1,3-oxazol-4-yl]pyridin-2(1H)-one TLC: Rf 0.22 (dichloromethane:methanol:ammonia water=90:10:1); NMR: δ 1.75-1.92 (m, 2H), 2.02-2.14 (m, 2H), 2.18 (s, 3H), 2.69-2.83 (m, 2H), 2.90-3.06 (m, 1H), 3.14-3.24 (m, 2H), 6.67 (d, J=9.51 Hz, 1H), 6.89-7.04 (m, 2H), 7.21-7.33 (m, 2H), 7.35-7.41 (m, 1H), 7.42-7.58 (m, 3H).

Example 20(6)

5-[5-(2,4-difluorophenyl)-2-(piperidin-4-yl)-1,3-oxazol-4-yl]-1-(2,6-dimethylphenyl)pyridin-2(1H)-one TLC: Rf 0.37 (dichloromethane:methanol:triethylamine=50:10:1); NMR: δ 1.76-1.95 (m, 2H), 2.10 (s, 9H), 2.72-2.84 (m, 2H), 2.91-3.05 (m, 1H), 3.15-3.26 (m, 2H), 6.67 (d, J=9.52 Hz, 1H), 6.85-7.05 (m, 2H), 7.12-7.19 (m, 2H), 7.20-7.25 (m, 1H), 7.46 (d, J=2.01 Hz, 1H), 7.48-7.56 (m, 2H).

Example 20(7)

5-[5-(2,4-difluorophenyl)-2-(piperidin-4-yl)-1,3-oxazol-4-yl]-1-(4-fluoro-2,6-dimethylphenyl)pyridin-2(1H)-one TLC: Rf 0.60 (dichloromethane:methanol:acetic acid=10:2:1); NMR (CD₃OD): δ 7.72-7.60 (m, 2H), 7.55 (d, J=2.1 Hz, 1H), 7.17-7.09 (m, 2H), 6.99 (s, 1H), 6.96 (s, 1H), 6.70 (d, J=9.6 Hz, 1H), 3.20-3.00 (m, 3H), 2.80-2.70 (m, 2H), 2.15-2.00 (m, 2H), 2.05 (s, 6H), 1.95-1.75 (m, 2H).

Example 20(8)

1-(4-chloro-2,6-dimethylphenyl)-5-[5-(2,4-difluorophenyl)-2-(piperidin-4-yl)-1,3-oxazol-4-yl]pyridin-2(1H)-one TLC: Rf 0.21 (ethyl acetate:methanol:ammonia water=80:10:1); NMR: δ 1.64-1.93 (m, 5H), 2.08 (s, 6H), 2.69-2.84 (m, 2H), 2.91-3.03 (m, 1H), 3.13-3.26 (m, 2H), 6.67 (d, J=9.1 Hz, 1H), 6.86-7.06 (m, 2H), 7.16 (s, 2H), 7.41 (d, J=2.4 Hz, 1H), 7.45-7.57 (m, 2H).

Example 20(9)

5-[5-(2,4-difluorophenyl)-2-(piperidin-4-yl)-1,3-oxazol-4-yl]-1-(4-methoxy-2,6-dimethylphenyl)pyridin-2(1H)-one TLC: Rf 0.35 (ethyl acetate:methanol:triethylamine=1:2:1); NMR: δ 1.85-1.98 (m, 2H), 2.03-2.28 (m, 9H), 2.74-2.87 (m, 2H), 2.94-3.08 (m, 1H), 3.17-3.27 (m, 2H), 3.80 (s, 3H), 6.64-6.72 (m, 3H), 6.87-7.04 (m, 2H), 7.43-7.55 (m, 3H).

Example 20(10)

1-(2,6-difluorophenyl)-5-[5-(4-fluorophenyl)-2-(piperidin-4-yl)-1,3-oxazol-4-yl]pyridin-2(1H)-one TLC: Rf 0.19 (dichloromethane:methanol:ammonia water=90:10:1); NMR: δ 2.28-2.50 (m, 4H), 3.09-3.28 (m, 3H), 3.42-3.57 (m, 2H), 6.67 (d, J=9.88 Hz, 1H), 7.03-7.20 (m, 4H), 7.37-7.49 (m, 1H), 7.50-7.63 (m, 4H).

Example 20(11)

1-(2,6-dimethylphenyl)-5-[5-(2-fluoro-4-methylphenyl)-2-(piperidin-4-yl)-1,3-oxazol-4-yl]pyridin-2(1H)-one TLC: Rf 0.59 (dichloromethane:methanol:acetic acid=10:2:1); NMR: δ 7.56 (m, 1H), 7.47 (d, J=2.1 Hz, 1H), 7.41 (t, J=7.8 Hz, 1H), 7.25 (m, 1H), 7.20-7.12 (m, 2H), 7.04 (m, 1H), 6.97 (m, 1H), 6.67 (dd, J=9.6, 0.6 Hz, 1H), 3.26-3.14 (m, 2H), 2.98 (m, 1H), 2.84-2.72 (m, 2H), 2.41 (s, 3H), 2.20-1.78 (m, 5H), 2.11 (s, 6H).

Example 20(12)

5-{5-(2,4-difluorophenyl)-2-[(3R)-piperidin-3-yl]-1,3-oxazol-4-yl}-1-(2,6-dimethylphenyl)pyridin-2(1H)-one

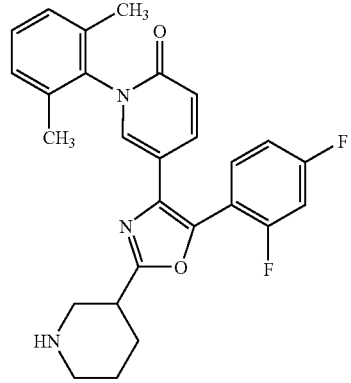

TLC: Rf 0.40 (dichloromethane:methanol:ammonia water=90:10:1); NMR: δ 1.50-1.67 (m, 1H), 1.70-1.99 (m, 2H), 2.11 (s, 6H), 2.13-2.26 (m, 1H), 2.65-2.80 (m, 1H), 2.92-3.10 (m, 3H), 3.28-3.45 (m, 1H), 6.68 (d, J=9.5 Hz, 1H), 6.86-7.06 (m, 2H), 7.14-7.21 (m, 2H), 7.21-7.30 (m, 1H), 7.42-7.57 (m, 3H).

Example 20(13)

5-{5-(2,4-difluorophenyl)-2-[(3S)-piperidin-3-yl]-1,3-oxazol-4-yl}-1-(2,6-dimethylphenyl)pyridin-2(1H)-one

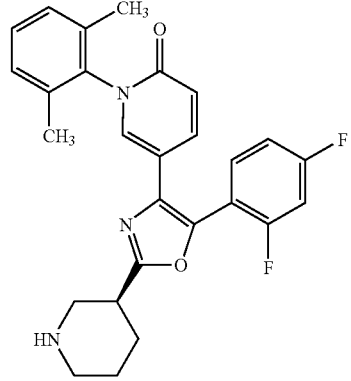

TLC: Rf 0.44 (dichloromethane:methanol:ammonia water=90:10:1); NMR: δ 1.48-1.67 (m, 1H), 1.70-1.97 (m, 2H), 2.11 (s, 6H), 2.12-2.26 (m, 1H), 2.64-2.80 (m, 1H), 2.93-3.09 (m, 3H), 3.27-3.44 (m, 1H), 6.68 (d, J=9.5 Hz, 1H), 6.85-7.06 (m, 2H), 7.14-7.20 (m, 2H), 7.21-7.31 (m, 1H), 7.43-7.58 (m, 3H).

Example 20(14)

1-(2,6-difluoro-4-methoxyphenyl)-5-[5-(2,4-difluorophenyl)-2-(4-piperidinyl-1,3-oxazol-4-yl]-2(1H)-pyridinone TLC: Rf 0.37 (dichloromethane:methanol:triethylamine=60:10:1); NMR: δ 1.73-1.92 (m, 2H), 2.01-2.15 (m, 2H), 2.68-2.83 (m, 2H), 2.89-3.06 (m, 1H), 3.12-3.25 (m, 2H), 3.83 (s, 3H), 6.52-6.67 (m, 3H), 6.89-7.06 (m, 2H), 7.40-7.56 (m, 2H), 7.60 (d, J=2.4 Hz, 1H).

Example 21(1)-Example 21(14)

By the same procedure as a reaction of Example 19, using the compounds prepared in Example 20(1)-Example 20(14) instead of the compound prepared in Example 18, the compounds of the present invention having the following physical data were obtained.

Example 21(1)

5-[5-(2,4-difluorophenyl)-2-(1-methylpiperidin-4-yl)-1,3-oxazol-4-yl]-1-(2-fluorophenyl)pyridin-2(1H)-one TLC: Rf 0.64 (dichloromethane:methanol:water=80:20:1); NMR: δ 7.71 (d, J=2.7 Hz, 1H), 7.54-7.20 (m, 6H), 7.04-6.91 (m, 2H), 6.60 (dd, J=9.9, 0.9 Hz, 1H), 3.06-2.76 (m, 3H), 2.36 (s, 3H), 2.28-1.90 (m, 6H).

Example 21(2)

5-[5-(2,4-difluorophenyl)-2-(1-methylpiperidin-4-yl)-1,3-oxazol-4-yl]-1-(2,4,6-trifluorophenyl)pyridin-2(1H)-one TLC: Rf 0.56 (dichloromethane:methanol:triethylamine=40:10:1); NMR: δ 1.87-2.19 (m, 6H), 2.31 (s, 3H), 2.74-3.00 (m, 3H), 6.62 (d, J=9.7 Hz, 1H), 6.80-6.91 (m, 2H), 6.91-7.06 (m, 2H), 7.40-7.55 (m, 2H), 7.59 (d, J=2.2 Hz, 1H).

Example 21(3)

5-[5-(2,4-difluorophenyl)-2-(1-methylpiperidin-4-yl)-1,3-oxazol-4-yl]-1-(2,3,6-trifluorophenyl)pyridin-2(1H)-one TLC: Rf 0.37 (ethyl acetate:triethylamine=9:1); NMR: δ 1.92-2.22 (m, 6H), 2.33 (s, 3H), 2.76-3.00 (m, 3H), 6.63 (d, J=9.7 Hz, 1H), 6.92-7.10 (m, 3H), 7.24-7.36 (m, 1H), 7.43-7.55 (m, 2H), 7.59-7.64 (m, 1H).

Example 21(4)

5-[5-(2,4-difluorophenyl)-2-(1-methylpiperidin-4-yl)-1,3-oxazol-4-yl]-1-(2-fluoro-6-methylphenyl)pyridin-2(1H)-one TLC: Rf 0.37 (dichloromethane:methanol:ammonia water=90:10:1); NMR: δ 1.92-2.25 (m, 9H), 2.35 (s, 3H), 2.75-3.02 (m, 3H), 6.65 (d, J=9.51 Hz, 1H), 6.89-7.16 (m, 4H), 7.27-7.38 (m, 1H), 7.44-7.55 (m, 3H).

Example 21(5)

1-(2-chloro-6-methylphenyl)-5-[5-(2,4-difluorophenyl)-2-(1-methylpiperidin-4-yl)-1,3-oxazol-4-yl]pyridin-2(1H)-one TLC: Rf 0.38 (dichloromethane:methanol:ammonia water=90:10:1); NMR: δ 1.89-2.21 (m, 9H), 2.34 (s, 3H), 2.74-2.89 (m, 1H), 2.89-3.00 (m, 2H), 6.67 (d, J=9.70Hz, 1H), 6.88-7.03 (m, 2H), 7.20-7.33 (m, 2H), 7.35-7.41 (m, 1H), 7.42-7.57 (m, 3H).

Example 21(6)

5-[5-(2,4-difluorophenyl)-2-(1-methylpiperidin-4-yl)-1,3-oxazol-4-yl]-1-(2,6-dimethylphenyl)pyridin-2(1H)-one TLC: Rf 0.30 (ethyl acetate:methanol:triethylamine=20:10:1); NMR: δ 1.89-2.20 (m, 12H), 2.33 (s, 3H), 2.71-2.88 (m, 1H), 2.89-3.00 (m, 2H), 6.67 (dd, J=9.52, 0.73 Hz, 1H), 6.86-7.04 (m, 2H), 7.14-7.19 (m, 2H), 7.20-7.25 (m, 1H), 7.43-7.47 (m, 1H), 7.47-7.56 (m, 2H).

Example 21(7)

5-[5-(2,4-difluorophenyl)-2-(1-methylpiperidin-4-yl)-1,3-oxazol-4-yl]-1-(4-fluoro-2,6-dimethylphenyl)pyridin-2(1H)-one TLC: Rf 0.86 (dichloromethane:methanol:water=80:20:1); NMR: δ 7.56-7.42 (m, 3H), 7.03-6.85 (m, 2H), 6.89 (s, 1H), 6.86 (s, 1H), 6.67 (d, J=9.6 Hz, 1H), 3.00-2.90 (m, 2H), 2.81 (m, 1H), 2.32 (s, 3H), 2.20-1.90 (m, 6H), 2.09 (s, 6H).

Example 21(8)

1-(4-chloro-2,6-dimethylphenyl)-5-[5-(2,4-difluorophenyl)-2-(1-methylpiperidin-4-yl)-1,3-oxazol-4-yl]pyridin-2(1H)-one TLC: Rf 0.45 (ethyl acetate:methanol:ammonia water=80:10:1); NMR: δ 1.90-2.19 (m, 12H), 2.34 (s, 3H), 2.75-2.88 (m, 1H), 2.88-3.01 (m, 2H), 6.66 (d, J=9.7 Hz, 1H), 6.85-7.07 (m, 2H), 7.16 (s, 2H), 7.40 (d, J=2.6 Hz, 1H), 7.44-7.57 (m, 2H).

Example 21(9)

5-[5-(2,4-difluorophenyl)-2-(1-methylpiperidin-4-yl)-1,3-oxazol-4-yl]-1-(4-methoxy-2,6-dimethylphenyl)pyridin-2(1H)-one TLC: Rf 0.49 (ethyl acetate:methanol:triethylamine=8:1:1); NMR: δ 1.89-2.20 (m, 12H), 2.32 (s, 3H), 2.74-2.99 (m, 3H), 3.80 (s, 3H), 6.63-6.72 (m, 3H), 6.87-7.04 (m, 2H), 7.42-7.56 (m, 3H).

Example 21(10)

1-(2,6-difluorophenyl)-5-[5-(4-fluorophenyl)-2-(1-methylpiperidin-4-yl)-1,3-oxazol-4-yl]pyridin-2(1H)-one TLC: Rf 0.39 (dichloromethane:methanol:ammonia water=90:10:1); NMR: δ 1.93-2.20 (m, 6H), 2.33 (s, 3H), 2.75-2.87 (m, 1H), 2.89-3.00 (m, 2H), 6.69 (d, J=10.43 Hz, 1H), 7.03-7.17 (m, 4H), 7.37-7.48 (m, 1H), 7.53-7.63 (m, 4H).

Example 21(11)

1-(2,6-dimethylphenyl)-5-[5-(2-fluoro-4-methylphenyl)-2-(1-methylpiperidin-4-yl)-1,3-oxazol-4-yl]pyridin-2(1H)-one TLC: Rf 0.53 (dichloromethane:methanol:water=80:20:1); NMR: δ 7.57 (m, 1H), 7.46 (d, J=2.1 Hz, 1H), 7.38 (t, J=7.8 Hz, 1H), 7.25 (m, 1H), 7.20-7.12 (m, 2H), 7.04 (m, 1H), 6.97

(m, 1H), 6.67 (dd, J=9.6, 0.6 Hz, 1H), 3.30-2.74 (m, 3H), 2.41 (s, 3H), 2.33 (s, 3H), 2.24-1.90 (m, 6H), 2.11 (s, 6H).

Example 21(12)

5-{5-(2,4-difluorophenyl)-2-[(3R)-1-methylpiperidin-3-yl]-1,3-oxazol-4-yl}-1-(2,6-dimethylphenyl)pyridin-2(1H)-one TLC: Rf 0.58 (dichloromethane:methanol:ammonia water=90:10:1); NMR: δ 1.49-1.93 (m, 3H), 1.97-2.22 (m, 8H), 2.22-2.41 (m, 4H), 2.75-2.89 (m, 1H), 3.05-3.23 (m, 2H), 6.67 (d, J=9.7 Hz, 1H), 6.85-7.06 (m, 2H), 7.13-7.21 (m, 2H), 7.20-7.31 (m, 1H), 7.42-7.59 (m, 3H).

Example 21(13)

5-{5-(2,4-difluorophenyl)-2-[(3S)-1-methylpiperidin-3-yl]-1,3-oxazol-4-yl}-1-(2,6-dimethylphenyl)pyridin-2(1H)-one TLC: Rf 0.58 (dichloromethane:methanol:ammonia water=90:10:1); NMR: δ 1.50-1.96 (m, 3H), 1.95-2.20 (m, 8H), 2.21-2.42 (m, 4H), 2.75-2.88 (m, 1H), 3.05-3.24 (m, 2H), 6.67 (d, J=9.7 Hz, 1H), 6.85-7.06 (m, 2H), 7.13-7.20 (m, 2H), 7.21-7.31 (m, 1H), 7.41-7.57 (m, 3H).

Example 21(14)

1-(2,6-difluoro-4-methoxyphenyl)-5-[5-(2,4-difluorophenyl)-2-(1-methyl-4-piperidinyl)-1,3-oxazol-4-yl]-2(1H)-pyridinone TLC: Rf 0.49 (dichloromethane:methanol:triethylamine=60:10:1); NMR: δ 1.88-2.20 (m, 6H), 2.32 (s, 3H), 2.70-3.03 (m, 3H), 3.82 (s, 3H), 6.54-6.65 (m, 3H), 6.89-7.03 (m, 2H), 7.39-7.53 (m, 2H), 7.58 (d, J=2.4 Hz, 1H).

Example 22

1-(2,6-dimethylphenyl)-5-[5-(2-fluoro-4-methylphenyl)-2-(4-piperidinyl)-1,3-thiazol-4-yl]-2(1H)-pyridinone By the same procedure as a series of reactions of Example 5→Example 6→Example 12→Example 7→Example 8→Example 9, using coumaric acid instead of the compound prepared in Example 4 used in the reaction of Example 5, 2-fluoro-4-methylbenzyl bromide instead of 2-chloro-4-fluorobenzyl bromide used in the reaction of Example 6, and 2,6-dimethylaniline instead of 2,6-difluoroaniline used in the reaction of Example 12, the compound of the present invention having the following physical data was obtained.

TLC: Rf 0.41 (dichloromethane:methanol:acetic acid=10:2:1); NMR: δ 7.53 (dd, J=9.6, 2.4 Hz, 1H), 7.35 (dd, J=2.4, 0.6 Hz, 1H), 7.28-7.16 (m, 2H), 7.16-7.08 (m, 2H), 6.99-6.89 (m, 2H), 6.60 (dd, J=9.6, 0.6 Hz, 1H), 3.32-3.19 (m, 2H), 3.13 (m, 1H), 2.89-2.73 (m, 2H), 2.38 (s, 3H), 2.25-1.70 (m, 5H), 2.03 (s, 6H).

Example 22(1)-Example 22(5)

By the same procedure as a reaction of Example 22, using coumaric acid instead of the compound prepared in Example 4, 2,4-difluorobenzyl bromide instead of 2-chloro-4-fluorobenzyl bromide, the corresponding aniline compounds instead of 2,6-difluoroaniline, and the corresponding thioamide compounds instead of tert-butyl 4-(aminocarbonothioyl)piperidine-1-carboxylate, the compounds of the present invention having the following physical data were obtained.

Example 22(1)

1-(4-chloro-2,6-dimethylphenyl)-5-[5-(2,4-difluorophenyl)-2-(4-piperidinyl-1,3-thiazol-4-yl]-2(1H)-pyridinone TLC: Rf 0.20 (ethyl acetate:methanol:triethylamine=6:3:1); NMR: δ 1.73-1.90 (m, 2H), 1.98-2.04 (m, 7H), 2.12-2.23 (m, 2H), 2.74-2.87 (m, 2H), 3.07-3.30 (m, 3H), 6.62 (dd, J=9.5, 0.7 Hz, 1H), 6.85-6.99 (m, 2H), 7.15 (s, 2H), 7.29-7.39 (m, 2H), 7.51 (dd, J=9.5, 2.6 Hz, 1H).

Example 22(2)

5-[5-(2,4-difluorophenyl)-2-(4-piperidinyl)-1,3-thiazol-4-yl]-1-(2-fluorophenyl)-2(1H)-pyridinone TLC: Rf 0.24 (ethyl acetate:methanol:triethylamine=2:2:1); NMR: δ 1.82-1.96 (m, 2H), 2.15-2.26 (m, 2H), 2.79-2.91 (m, 2H), 3.08-3.22 (m, 2H), 3.24-3.35 (m, 2H), 6.55 (dd, J=9.6, 0.6 Hz, 1H), 6.89-7.01 (m, 2H), 7.18-7.48 (m, 6H), 7.60-7.65 (m, 1H).

Example 22(3)

5-{5-(2,4-difluorophenyl)-2-[(2R)-2-piperidinyl]-1,3-thiazol-4-yl}-1-(2,6-dimethylphenyl)-2(1H)-pyridinone TLC: Rf 0.41 (dichloromethane:methanol=9:1); NMR: δ 1.47-1.77 (m, 4H), 1.87-1.99 (m, 1H), 2.03 (s, 6H), 2.10-2.22 (m, 1H), 2.75-2.92 (m, 1H), 3.15-3.27 (m, 1H), 3.98-4.09 (m, 1H), 6.62 (dd, J=9.51, 0.64 Hz, 1H), 6.83-6.98 (m, 2H), 7.10-7.17 (m, 2H), 7.18-7.27 (m, 1H), 7.28-7.38 (m, 2H), 7.50 (dd, J=9.51, 2.56 Hz, 1H).

Example 22(4)

5-[5-(2,4-difluorophenyl)-2-(4-piperidinyl)-1,3-thiazol-4-yl]-1-(4-fluoro-2,6-dimethylphenyl)-2(1H)-pyridinone TLC: Rf 0.24 (dichloromethane:methanol:acetic acid=10:2:1); NMR: δ 7.50 (dd, J=9.6, 2.7 Hz, 1H), 7.38-7.25 (m, 2H), 6.98-6.84 (m, 4H), 6.62 (d, J=9.6 Hz, 1H), 3.38-3.26 (m, 2H), 3.18 (m, 1H), 2.92-2.83 (m, 2H), 2.90 (brs, 1H), 2.30-2.18 (m, 2H), 2.03 (s, 6H), 2.02-1.86 (m, 2H).

Example 22(5)

5-[5-(2,4-difluorophenyl)-2-(4-morpholinyl)-1,3-thiazol-4-yl]-1-(2,6-dimethylphenyl)-2(1H)-pyridinone TLC: Rf 0.40 (hexane:ethyl acetate=1:2); NMR: δ 2.04 (s, 6H), 3.45-3.54 (m, 4H), 3.78-3.85 (m, 4H), 6.58 (d, J=9.5 Hz, 1H), 6.82-6.94 (m, 2H), 7.11-7.18 (m, 2H), 7.19-7.39 (m, 3H), 7.47 (dd, J=9.5, 2.6 Hz, 1H).

Example 23

1-(2,6-dimethylphenyl)-5-[5-(2-fluoro-4-methylphenyl)-2-(1-methyl-4-piperidinyl)-1,3-thiazol-4-yl]-2(1H)-pyridinone By the same procedure as a reaction of Example 16, using the compound prepared in Example 22 instead of the compound prepared in Example 14, the compound of the present invention having the following physical data was obtained.

TLC: Rf 0.49 (dichloromethane:methanol:water=80:20:1); NMR: δ 7.54 (dd, J=9.6, 2.4 Hz, 1H), 7.37 (dd, J=2.4, 0.6 Hz, 1H), 7.30-7.17 (m, 2H), 7.16-7.09 (m, 2H), 7.00-6.89 (m, 2H), 6.61 (dd, J=9.6, 0.6 Hz, 1H), 3.06-2.88 (m, 3H), 2.38 (s, 3H), 2.33 (s, 3H), 2.23-1.80 (m, 6H), 2.03 (s, 6H).

Example 23(1)-Example 23(3)

By the same procedure as a reaction of Example 23, using the compounds prepared in Example 22(1)-Example 22(3) instead of the compound prepared in Example 22, the compounds of the present invention having the following physical data were obtained.

Example 23(1)

1-(4-chloro-2,6-dimethylphenyl)-5-[5-(2,4-difluorophenyl)-2-(1-methyl-4-piperidinyl)-1,3-thiazol-4-yl]-2(1H)-pyridinone TLC: Rf 0.54 (ethyl acetate:methanol:triethylamine=8:1:1); NMR: δ 1.84-1.97 (m, 2H), 2.01 (s, 6H), 2.05-2.21 (m, 4H), 2.33 (s, 3H), 2.91-3.04 (m, 3H), 6.61 (d, J=9.6 Hz, 1H), 6.85-6.98 (m, 2H), 7.14 (s, 2H), 7.29-7.39 (m, 2H), 7.51 (dd, J=9.6, 2.7 Hz, 1H).

Example 23(2)

5-[5-(2,4-difluorophenyl)-2-(1-methyl-4-piperidinyl)-1,3-thiazol-4-yl]-1-(2-fluorophenyl)-2(1H)-pyridinone TLC: Rf 0.49 (ethyl acetate:methanol:triethylamine=8:1:1); NMR: δ 1.83-2.00 (m, 2H), 2.03-2.22 (m, 4H), 2.33 (s, 3H), 2.89-3.05 (m, 3H), 6.53 (dd, J=9.7, 0.7 Hz, 1H), 6.87-6.99 (m, 2H), 7.17-7.46 (m, 6H), 7.59-7.65 (m, 1H).

Example 23(3)

5-{5-(2,4-difluorophenyl)-2-[(2R)-1-methyl-2-piperidinyl]-1,3-thiazol-4-yl}-1-(2,6-dimethylphenyl)-2(1H)-pyridinone TLC: Rf 0.46 (dichloromethane:methanol=9:1); NMR: δ 1.31-1.48 (m, 1H), 1.58-1.77 (m, 3H), 1.78-1.90 (m, 1H), 1.97-2.09 (m, 7H), 2.12-2.28 (m, 4H), 3.01-3.10 (m, 1H), 3.32-3.39 (m, 1H), 6.63 (d, J=9.51 Hz, 1H), 6.84-7.00 (m, 2H), 7.09-7.17 (m, 2H), 7.18-7.27 (m, 1H), 7.28-7.42 (m, 2H), 7.51 (dd, J=9.51, 2.56 Hz, 1H).

Example 24

5-{5-(2,4-difluorophenyl)-2-[1-(2-methoxyethyl)-4-piperidinyl]-1,3-thiazol-4-yl}-1-(2,6-dimethylphenyl)-2(1H)-pyridinone By the same procedure as a reaction of Example 10, using the compound prepared in Example 15(1) instead of the compound prepared in Example 9 and methoxyethyl bromide instead of ethyl bromide, the compound of the present invention having the following physical data was obtained.

TLC: Rf 0.58 (dichloromethane:methanol=9:1); NMR: δ 1.81-2.08 (m, 8H), 2.07-2.27 (m, 4H), 2.62 (t, J=5.4 Hz, 2H), 2.89-3.17 (m, 3H), 3.37 (s, 3H), 3.54 (t, J=5.4 Hz, 2H), 6.62 (d, J=9.6 Hz, 1H), 6.82-6.99 (m, 2H), 7.10-7.19 (m, 2H), 7.18-7.29 (m, 1H), 7.29-7.41 (m, 2H), 7.50 (dd, J=9.6, 2.3 Hz, 1H).

Example 24(1)-Example 24(5)

By the same procedure as a reaction of Example 24, using the corresponding amine compounds instead of the compound prepared in Example 15(1), the compounds of the present invention having the following physical data were obtained.

Example 24(1)

1-(4-chloro-2,6-dimethylphenyl)-5-{5-(2,4-difluorophenyl)-2-[1-(2-methoxyethyl)-4-piperidinyl]-1,3-thiazol-4-yl}-2(1H)-pyridinone TLC: Rf 0.54 (dichloromethane:methanol=9:1); NMR: δ 1.81-2.05 (m, 8H), 2.06-2.25 (m, 4H), 2.62 (t, J=5.5 Hz, 2H), 2.90-3.15 (m, 3H), 3.37 (s, 3H), 3.54 (t, J=5.5 Hz, 2H), 6.61 (d, J=9.5 Hz, 1H), 6.82-6.99 (m, 2H), 7.11-7.18 (m, 2H), 7.29-7.41 (m, 2H), 7.50 (dd, J=9.5, 2.6 Hz, 1H).

Example 24(2)

5-{5-(2,4-difluorophenyl)-2-[1-(2-methoxyethyl)-4-piperidinyl]-1,3-thiazol-4-yl}-1-(4-fluoro-2,6-dimethylphenyl)-2(1H)-pyridinone TLC: Rf 0.37 (dichloromethane:methanol:ammonia water=90:10:1); NMR: δ 1.83-2.04 (m, 8H), 2.06-2.21 (m, 4H), 2.61 (t, J=5.58 Hz, 2H), 2.92-3.15 (m, 3H), 3.37 (s, 3H), 3.53 (t, J=5.58 Hz, 2H), 6.61 (dd, J=9.51, 0.64 Hz, 1H), 6.82-6.98 (m, 4H), 7.29-7.39 (m, 2H), 7.49 (dd, J=9.51, 2.56 Hz, 1H).

Example 24(3)

5-{5-(2,4-difluorophenyl)-2-[1-(2-methoxyethyl)-4-piperidinyl]-1,3-oxazol-4-yl}-1-(2,6-dimethylphenyl)-2(1H)-pyridinone TLC: Rf 0.73 (dichloromethane:methanol:water=80:20:1); NMR: δ 7.55-7.41 (m, 3H), 7.27-7.11 (m, 3H), 7.03-6.87 (m, 2H), 6.67 (dd, J=9.3, 0.6 Hz, 1H), 3.53 (t, J=5.4 Hz, 2H), 3.36 (s, 3H), 3.07-2.96 (m, 2H), 2.83 (m, 1H), 2.61 (t, J=5.4 Hz, 2H), 2.30-1.90 (m, 6H), 2.10 (s, 6H).

Example 24(4)

5-{5-(2,4-difluorophenyl)-2-[1-(2-methoxyethyl)-4-piperidinyl]-1,3-oxazol-4-yl}-1-(4-fluoro-2,6-dimethylphenyl)-2(1H)-pyridinone TLC: Rf 0.55 (dichloromethane:methanol:triethylamine=60:10:1); NMR: δ 1.93-2.25 (m, 12H), 2.60 (t, J=5.7 Hz, 2H), 2.75-2.91 (m, 1H), 2.95-3.10 (m, 2H), 3.36 (s, 3H), 3.53 (t, J=5.7 Hz, 2H), 6.66 (d, J=9.5 Hz, 1H), 6.84-7.05 (m, 4H), 7.42 (d, J=2.6 Hz, 1H), 7.45-7.54 (m, 2H).

Example 24(5)

1-(4-chloro-2,6-dimethylphenyl)-5-{5-(2,4-difluorophenyl)-2-[1-(2-methoxyethyl)-4-piperidinyl]-1,3-oxazol-4-yl}-2(1H)-pyridinone TLC: Rf 0.20 (dichloromethane:methanol:triethylamine=75:5:2); NMR: δ 1.88-2.26 (m, 12H), 2.60 (t, J=5.6 Hz, 2H), 2.74-2.93 (m, 1H), 2.96-3.09 (m, 2H), 3.36 (s, 3H), 3.53 (t, J=5.6 Hz, 2H), 6.66 (d, J=9.1 Hz, 1H), 6.87-7.06 (m, 2H), 7.16 (s, 2H), 7.40 (d, J=2.2 Hz, 1H), 7.44-7.56 (m, 2H).

Example 25

5-{5-(2,4-difluorophenyl)-2-[1-(2-hydroxyethyl)-4-piperidinyl]-1,3-thiazol-4-yl}-1-(2,6-dimethylphenyl)-2(1H)-pyridinone To a solution of the compound prepared in Example 15(1) (300 mg) in acetonitrile (5 mL) were added 2-(2-bromoethoxy)tetrahydro-(2H)-pyran (285 µL) and triethylamine (263 µL) and the mixture was stirred at 70° C. for 6 hours and concentrated. The obtained residue was dissolved in tetrahydrofuran (4 mL), added by 5 N hydrochloric acid (2 mL) and stirred at 50° C. for 40 minutes. The reaction mixture was poured into 5 N aqueous sodium hydroxide—ice, then extracted with ethyl acetate. The obtained organic layer was washed with brine, dried and concentrated. The obtained residue was purified by preparative TLC (dichloromethane: methanol: ammonia water=90:10:1) to give the compound of the present invention (230 mg) having the following physical data.

TLC: Rf 0.52 (dichloromethane:methanol:ammonia water=90:10:1); NMR: δ 1.78-1.98 (m, 2H), 2.04 (s, 6H), 2.08-2.33 (m, 4H), 2.58 (t, J=5.4 Hz, 2H), 2.93-3.11 (m, 3H), 3.63 (t, J=5.4 Hz, 2H), 6.63 (d, J=9.5 Hz, 1H), 6.83-6.99 (m, 2H), 7.10-7.17 (m, 2H), 7.18-7.28 (m, 1H), 7.29-7.40 (m, 2H), 7.51 (dd, J=9.5, 2.6 Hz, 1H).

Example 25(1)-Example 25(5)

By the same procedure as a reaction of Example 25, using the corresponding amine compounds instead of the compound prepared in Example 15(1), the compounds of the present invention having the following physical data were obtained.

Example 25(1)

1-(4-chloro-2,6-dimethylphenyl)-5-{5-(2,4-difluorophenyl)-2-[1-(2-hydroxyethyl)-4-piperidinyl]-1,3-thiazol-4-yl}-2(1H)-pyridinone TLC: Rf 0.57 (dichloromethane:methanol:ammonia water=90:10:1); NMR: δ 1.79-1.98 (m, 2H), 2.01 (s, 6H), 2.09-2.33 (m, 4H), 2.59 (t, J=5.3 Hz, 2H), 2.93-3.15 (m, 3H), 3.64 (t, J=5.3 Hz, 2H), 6.62 (d, J=9.6 Hz, 1H), 6.84-6.99 (m, 2H), 7.11-7.18 (m, 2H), 7.28-7.41 (m, 2H), 7.51 (dd, J=9.6, 2.5 Hz, 1H).

Example 25(2)

5-{5-(2,4-difluorophenyl)-2-[1-(2-hydroxyethyl)-4-piperidinyl]-1,3-thiazol-4-yl}-1-(4-fluoro-2,6-dimethylphenyl)-2(1H)-pyridinone TLC: Rf 0.33 (dichloromethane:methanol:ammonia water=90:10:1); NMR: δ 1.80-2.05 (m, 8H), 2.12-2.37 (m, 4H), 2.61 (t, J=5.49 Hz, 2H), 2.95-3.14 (m, 3H), 3.66 (t, J=5.49 Hz, 2H), 6.62 (dd, J=9.51, 0.64 Hz, 1H), 6.82-6.98 (m, 4H), 7.29-7.39 (m, 2H), 7.51 (dd, J=9.51, 2.56 Hz, 1H).

Example 25(3)

5-{5-(2,4-difluorophenyl)-2-[1-(2-hydroxyethyl)-4-piperidinyl]-1,3-oxazol-4-yl}-1-(2,6-dimethylphenyl)-2(1H)-pyridinone TLC: Rf 0.49 (dichloromethane:methanol:water=80:20:1); NMR: δ 7.56-7.44 (m, 3H), 7.30-7.12 (m, 3H), 7.04-6.88 (m, 2H), 6.68 (dd, J=9.3, 0.6 Hz, 1H), 3.63 (t, J=5.4 Hz, 2H), 3.06-2.93 (m, 2H), 2.87 (m, 1H), 2.58 (t, J=5.4 Hz, 2H), 2.55 (m, 1H), 2.33-1.88 (m, 6H), 2.11 (s, 6H).

Example 25(4)

5-{5-(2,4-difluorophenyl)-2-[1-(2-hydroxyethyl)-4-piperidinyl]-1,3-oxazol-4-yl}-1-(4-fluoro-2,6-dimethylphenyl)-2(1H)-pyridinone TLC: Rf 0.57 (dichloromethane:methanol:triethylamine=60:10:1); NMR: δ 1.86-2.17 (m, 10H), 2.20-2.33 (m, 2H), 2.58 (t, J=5.4 Hz, 2H), 2.79-2.94 (m, 1H), 2.94-3.06 (m, 2H), 3.62 (t, J=5.4 Hz, 2H), 6.65 (d, J=10.1 Hz, 1H), 6.82-7.05 (m, 4H), 7.42 (d, J=2.2 Hz, 1H), 7.45-7.55 (m, 2H).

Example 25(5)

1-(4-chloro-2,6-dimethylphenyl)-5-{5-(2,4-difluorophenyl)-2-[1-(2-hydroxyethyl)-4-piperidinyl]-1,3-oxazol-4-yl}-2(1H)-pyridinone TLC: Rf 0.44 (dichloromethane:methanol:triethylamine=60:10:1); NMR: δ 1.82-2.18 (m, 10H), 2.18-2.32 (m, 2H), 2.58 (t, J=5.4 Hz, 2H), 2.79-2.94 (m, 1H), 2.94-3.05 (m, 2H), 3.63 (t, J=5.4 Hz, 2H), 6.67 (dd, J=9.6, 0.6 Hz, 1H), 6.86-7.07 (m, 2H), 7.17 (s, 2H), 7.42 (d, J=2.0 Hz, 1H), 7.45-7.57 (m, 2H).

Example 26(1)-Example 26(10)

By the same procedure as a reaction of Example 10, using the compound prepared in Example 20(6) instead of the compound prepared in Example 9 and the corresponding halides instead of ethyl bromide, the compounds of the present invention having the following physical data were obtained.

Example 26(1)

5-[5-(2,4-difluorophenyl)-2-(1-ethyl-4-piperidinyl)-1,3-oxazol-4-yl]-1-(2,6-dimethylphenyl)-2(1H)-pyridinone TLC: Rf 0.36 (dichloromethane:methanol:ammonia water=90:10:1); NMR: δ 1.07-1.19 (m, 3H), 1.92-2.22 (m, 12H), 2.38-2.58 (m, 2H), 2.78-2.93 (m, 1H), 2.95-3.10 (m, 2H), 6.67 (dd, J=9.70, 0.73 Hz, 1H), 6.87-7.03 (m, 2H), 7.13-7.29 (m, 3H), 7.44-7.55 (m, 3H).

Example 26(2)

5-[5-(2,4-difluorophenyl)-2-(1-isopropyl-4-piperidinyl)-1,3-oxazol-4-yl]-1-(2,6-dimethylphenyl)-2(1H)-pyridinone TLC: Rf 0.38 (dichloromethane:methanol:ammonia water=90:10:1); NMR: δ 1.07 (d, J=5.67 Hz, 6H), 1.85-2.16 (m, 10H), 2.18-2.38 (m, 2H), 2.69-2.90 (m, 2H), 2.90-3.04 (m, 2H), 6.67 (dd, J=9.51, 0.55 Hz, 1H), 6.86-7.04 (m, 2H), 7.13-7.28 (m, 3H), 7.43-7.55 (m, 3H).

Example 26(3)

5-[2-[1-(cyclopropylmethyl)-4-piperidinyl]-5-(2,4-difluorophenyl)-1,3-oxazol-4-yl]-1-(2,6-dimethylphenyl)-2(1H)-pyridinone TLC: Rf 0.71 (dichloromethane:methanol:water-80:20:1); NMR: δ 7.54-7.42 (m, 3H), 7.30-7.10 (m, 3H), 7.02-6.86 (m, 2H), 6.66 (dd, J=9.3, 0.6 Hz, 1H), 3.20-3.05 (m, 2H), 2.84 (m, 1H), 2.40-1.80 (m, 8H), 2.10 (s, 6H), 0.90 (m, 1H), 0.60-0.45 (m, 2H), 0.20-0.05 (m, 2H).

Example 26(4)

5-(5-(2,4-difluorophenyl)-2-{1-[2-(methylthio)ethyl]-4-piperidinyl}-1,3-oxazol-4-yl)-1-(2,6-dimethylphenyl)-2(1H)-pyridinone TLC: Rf 0.36 (ethyl acetate:methanol=9:1); NMR: δ 1.88-2.22 (m, 15H), 2.58-2.69 (m, 4H), 2.75-2.90 (m, 1H), 2.93-3.06 (m, 2H), 6.67 (dd, J=9.51, 0.73 Hz, 1H), 6.87-7.04 (m, 2H), 7.13-7.29 (m, 3H), 7.44-7.55 (m, 3H).

Example 26(5)

5-{5-(2,4-difluorophenyl)-2-[1-(3,3,3-trifluoropropyl)-4-piperidinyl]-1,3-oxazol-4-yl}-1-(2,6-dimethylphenyl)-2(1H)-pyridinone TLC: Rf 0.58 (ethyl acetate:triethylamine=19:1); NMR: δ 1.90-2.03 (m, 2H), 2.04-2.23 (m, 10H), 2.25-2.39 (m, 2H), 2.58-2.68 (m, 2H), 2.77-2.89 (m, 1H), 2.90-3.00 (m, 2H), 6.68 (dd, J=9.5, 0.5 Hz, 1H), 6.88-7.04 (m, 2H), 7.14-7.26 (m, 3H), 7.45-7.55 (m, 3H).

Example 26(6)

(4-{5-(2,4-difluorophenyl)-4-[1-(2,6-dimethylphenyl)-6-oxo-1,6-dihydro-3-pyridinyl]-1,3-oxazol-2-yl}-1-piperidinyl)acetonitrile

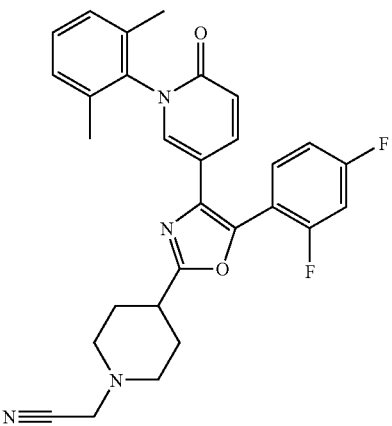

TLC: Rf 0.54 (dichloromethane:methanol=9:1); NMR: δ 1.88-2.05 (m, 2H), 2.11 (s, 6H), 2.12-2.23 (m, 2H), 2.42-2.57 (m, 2H), 2.78-2.96 (m, 3H), 3.56 (s, 2H), 6.68 (d, J=9.5 Hz, 1H), 6.87-7.05 (m, 2H), 7.12-7.20 (m, 2H), 7.21-7.29 (m, 1H), 7.41-7.57 (m, 3H).

Example 26(7)

3-(4-{5-(2,4-difluorophenyl)-4-[1-(2,6-dimethylphenyl)-6-oxo-1,6-dihydro-3-pyridinyl]-1,3-oxazol-2-yl}-1-piperidinyl)propanenitrile TLC: Rf 0.33 (ethyl acetate:methanol=19:1); NMR: δ 1.88-2.15 (m, 10H), 2.18-2.31 (m, 2H), 2.52 (t, J=6.86 Hz, 2H), 2.72 (t, J=6.86 Hz, 2H), 2.77-2.90 (m, 1H), 2.91-3.01 (m, 2H), 6.68 (dd, J=9.51, 0.73 Hz, 1H), 6.88-7.05 (m, 2H), 7.13-7.28 (m, 3H), 7.45-7.55 (m, 3H).

Example 26(8)

5-{5-(2,4-difluorophenyl)-2-[1-(2-oxopropyl)-4-piperidinyl]-1,3-oxazol-4-yl}-1-(2,6-dimethylphenyl)-2(1H)-pyridinone TLC: Rf 0.38 (dichloromethane:methanol:ammonia water=90:10:1); NMR: δ 2.01-2.13 (m, 10H), 2.17 (s, 3H), 2.20-2.39 (m, 2H), 2.78-3.00 (m, 3H), 3.23 (s, 2H), 6.67 (dd, J=9.51, 0.73 Hz, 1H), 6.88-7.04 (m, 2H), 7.14-7.28 (m, 3H), 7.45-7.55 (m, 3H).

Example 26(9)

(4-{5-(2,4-difluorophenyl)-4-[1-(2,6-dimethylphenyl)-6-oxo-1,6-dihydro-3-pyridinyl]-1,3-oxazol-2-yl}-1-piperidinyl)acetic acid

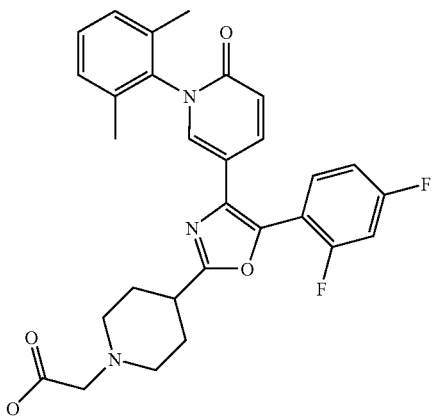

TLC: Rf 0.46 (dichloromethane:methanol=4:1); NMR (CD$_3$OD): δ 2.05 (s, 6H), 2.15-2.31 (m, 2H), 2.31-2.44 (m, 2H), 3.12-3.28 (m, 3H), 3.55-3.68 (m, 4H), 6.70 (d, J=9.51 Hz, 1H), 7.07-7.32 (m, 5H), 7.57 (d, J=2.01 Hz, 1H), 7.60-7.75 (m, 2H).

Example 26(10)

2-(4-{5-(2,4-difluorophenyl)-4-[1-(2,6-dimethylphenyl)-6-oxo-1,6-dihydro-3-pyridinyl]-1,3-oxazol-2-yl}-1-piperidinyl)-N,N-dimethylacetamide TLC: Rf 0.42 (dichloromethane:methanol:ammonia water=90:10:1); NMR: δ 1.91-2.19 (m, 10H), 2.21-2.42 (m, 2H), 2.78-2.92 (m, 1H), 2.92-3.05 (m, 5H), 3.09 (s, 3H), 3.23 (s, 2H), 6.67 (d, J=9.51 Hz, 1H), 6.88-7.04 (m, 2H), 7.13-7.29 (m, 3H), 7.44-7.55 (m, 3H).

Example 27(1)-Example 27(4)

By the same procedure as a reaction of Example 10, using the compound prepared in Example 20(8) instead of the compound prepared in Example 9 and the corresponding halides instead of ethyl bromide, the compounds of the present invention having the following physical data were obtained.

Example 27(1)

1-(4-chloro-2,6-dimethylphenyl)-5-(5-(2,4-difluorophenyl)-2-{1-[2-(methylthio)ethyl]-4-piperidinyl}-1,3-oxazol-4-yl)-2(1H)-pyridinone TLC: Rf 0.21 (ethyl acetate:methanol=19:1); NMR: δ 1.88-2.25 (m, 15H), 2.57-2.70 (m, 4H), 2.75-2.90 (m, 1H), 2.93-3.06 (m, 2H), 6.65 (d, J=9.70 Hz, 1H), 6.85-7.05 (m, 2H), 7.15 (s, 2H), 7.39 (d, J=2.56 Hz, 1H), 7.43-7.54 (m, 2H).

Example 27(2)

1-(4-chloro-2,6-dimethylphenyl)-5-{5-(2,4-difluorophenyl)-2-[1-(3,3,3-trifluoropropyl)-4-piperidinyl]-1,3-oxazol-4-yl}-2(1H)-pyridinone TLC: Rf 0.36 (ethyl acetate); NMR: δ 1.91-2.03 (m, 2H), 2.04-2.24 (m, 10H), 2.26-2.40 (m, 2H), 2.58-2.68 (m, 2H), 2.78-2.88 (m, 1H), 2.89-2.99 (m, 2H), 6.66 (d, J=9.5 Hz, 1H), 6.88-7.04 (m, 2H), 7.17 (s, 2H), 7.41 (d, J=2.7 Hz, 1H), 7.45-7.55 (m, 2H).

Example 27(3)

3-{4-[4-[1-(4-chloro-2,6-dimethylphenyl)-6-oxo-1,6-dihydro-3-pyridinyl]-5-(2,4-difluorophenyl)-1,3-oxazol-2-yl]-1-piperidinyl}propanenitrile TLC: Rf 0.30 (ethyl acetate:methanol=19:1); NMR: δ 1.92-2.16 (m, 10H), 2.18-2.32 (m, 2H), 2.52 (t, J=6.86 Hz, 2H), 2.72 (t, J=6.86 Hz, 2H), 2.78-2.90 (m, 1H), 2.91-3.01 (m, 2H), 6.66 (dd, J=9.70, 0.73 Hz, 1H), 6.87-7.06 (m, 2H), 7.17 (s, 2H), 7.41 (d, J=2.20 Hz, 1H), 7.45-7.56 (m, 2H).

Example 27(4)

1-(4-chloro-2,6-dimethylphenyl)-5-{5-(2,4-difluorophenyl)-2-[1-(2-oxopropyl)-4-piperidinyl]-1,3-oxazol-4-yl}-2(1H)-pyridinone TLC: Rf 0.15 (ethyl acetate:methanol=19:1); NMR: δ 1.99-2.12 (m, 10H), 2.16 (s, 3H), 2.19-2.31 (m, 2H), 2.77-2.98 (m, 3H), 3.20 (s, 2H), 6.65 (d, J=9.51 Hz, 1H), 6.86-7.04 (m, 2H), 7.15 (s, 2H), 7.40 (d, J=2.56 Hz, 1H), 7.43-7.55 (m, 2H).

Example 28

5-{5-(2,4-difluorophenyl)-2-[1-(2,2,2-trifluoroethyl)-4-piperidinyl]-1,3-oxazol-4-yl}-1-(2,6-dimethylphenyl)-2(1H)-pyridinone To a solution of the compound prepared in Example 20(6) (102 mg) in tetrahydrofuran (5 mL) were added triethylamine (67 mg) and 2,2,2-trifluoroethyltrifluoromethanesulfonic acid (77 mg) and the mixture was stirred at room temperature. The reaction mixture was added by water, then extracted with ethyl acetate. The obtained organic layer was dried and concentrated. The obtained residue was purified by preparative TLC (dichloromethane:methanol:triethylamine=100:10:1) to give the compound of the present invention (73 mg) having the following physical data.

TLC: Rf 0.57 (dichloromethane:methanol:triethylamine=60:10:1); NMR: δ 1.87-2.15 (m, 10H), 2.45-2.58 (m, 2H), 2.75-2.91 (m, 1H), 2.94-3.09 (m, 4H), 6.67 (dd, J=9.5, 0.7 Hz, 1H), 6.87-7.06 (m, 2H), 7.12-7.20 (m, 2H), 7.21-7.28 (m, 1H), 7.44-7.55 (m, 3H).

Example 28(1)

1-(4-chloro-2,6-dimethylphenyl)-5-{5-(2,4-difluorophenyl)-2-[1-(2,2,2-trifluoroethyl)-4-piperidinyl]-1,3-oxazol-4-yl}-2(1H)-pyridinone By the same procedure as a reaction of Example 28, using the compound prepared in Example 20(8) instead of the compound prepared in Example 20(6), the compound of the present invention having the following physical data was obtained.

TLC: Rf 0.33 (hexane:ethyl acetate=1:1); NMR: δ 1.89-2.12 (m, 10H), 2.45-2.59 (m, 2H), 2.77-2.90 (m, 1H), 2.94-3.10 (m, 4H), 6.66 (dd, J=9.61, 0.64 Hz, 1H), 6.87-7.05 (m, 2H), 7.17 (s, 2H), 7.41 (d, J=2.01 Hz, 1H), 7.45-7.55 (m, 2H).

Example 29

5-{5-(2,4-difluorophenyl)-2-[1-(3-oxobutyl)-4-piperidinyl]-1,3-oxazol-4-yl}-1-(2,6-dimethylphenyl)-2(1H)-pyridinone To a solution of the compound prepared in Example 20(6) (150 mg) in tetrahydrofuran (3.2 mL) was added methyvinylketone (0.054 mL) and the mixture was stirred at room temperature for 10 hours and concentrated. The obtained residue was purified by column chromatography on silica gel (ethyl acetate:methanol:triethylamine=1:0:0→13:1:1) to give the compound of the present invention (132 mg) having the following physical data.

TLC: Rf 0.24 (ethyl acetate:triethylamine=19:1); NMR: δ 1.84-2.00 (m, 2H), 2.01-2.15 (m, 10H), 2.18 (s, 3H), 2.59-2.73 (m, 4H), 2.76-2.88 (m, 1H), 2.89-2.99 (m, 2H), 6.67 (d, J=9.5 Hz, 1H), 6.87-7.04 (m, 2H), 7.13-7.25 (m, 3H), 7.43-7.55 (m, 3H).

Example 29(1)-Example 29(4)

By the same procedure as a reaction of Example 29, using the corresponding amine compounds instead of the compound prepared in Example 20(6) and the corresponding olefin compounds instead of methylvinylketone, the compounds of the present invention having the following physical data were obtained.

Example 29(1)

1-(4-chloro-2,6-dimethylphenyl)-5-{5-(2,4-difluorophenyl)-2-[1-(3-oxobutyl)-4-piperidinyl]-1,3-oxazol-4-yl}-2(1H)-pyridinone TLC: Rf 0.25 (ethyl acetate:triethylamine=19:1); NMR: δ 1.87-2.00 (m, 2H), 2.01-2.14 (m, 10H), 2.17 (s, 3H), 2.58-2.72 (m, 4H), 2.76-2.86 (m, 1H), 2.88-3.00 (m, 2H), 6.65 (dd, J=9.5, 0.7 Hz, 1H), 6.85-7.03 (m, 2H), 7.15 (s, 2H), 7.39 (d, J=2.4 Hz, 1H), 7.43-7.54 (m, 2H).

Example 29(2)

methyl 3-(4-{5-(2,4-difluorophenyl)-4-[1-(2,6-dimethylphenyl)-6-oxo-1,6-dihydro-3-pyridinyl]-1,3-oxazol-2-yl}-1-piperidinyl)propanoate TLC: Rf 0.35 (ethyl acetate:triethylamine=19:1); NMR: δ 1.86-2.22 (m, 12H), 2.53 (t, J=7.4 Hz, 2H), 2.72 (t, J=7.4 Hz, 2H), 2.77-2.89 (m, 1H), 2.90-3.00 (m, 2H), 3.68 (s, 3H), 6.67 (dd, J=9.5, 0.7 Hz, 1H), 6.87-7.04 (m, 2H), 7.13-7.25 (m, 3H), 7.43-7.55 (m, 3H).

Example 29(3)

5-(5-(2,4-difluorophenyl)-2-{1-[2-(methylsulfonyl)ethyl]-4-piperidinyl}-1,3-oxazol-4-yl)-1-(2,6-dimethylphenyl)-2(1H)-pyridinone TLC: Rf 0.26 (ethyl acetate:triethylamine=19:1); NMR: δ 1.85-1.99 (m, 2H), 2.06-2.29 (m, 10H), 2.79-2.86 (m, 1H), 2.90 (t, J=6.3 Hz, 2H), 2.94-3.03 (m, 2H), 3.05 (s, 3H), 3.15 (t, J=6.3 Hz, 2H), 6.67 (d, J=9.5 Hz, 1H), 6.88-7.04 (m, 2H), 7.14-7.29 (m, 3H), 7.44-7.54 (m, 3H).

Example 29(4)

1-(4-chloro-2,6-dimethylphenyl)-5-(5-(2,4-difluorophenyl)-2-{1-[2-(methylsulfonyl)ethyl]-4-piperidinyl}-1,3-oxazol-4-yl)-2(1H)-pyridinone TLC: Rf 0.64 (ethyl acetate:methanol:triethylamine=8:1:1); NMR: δ 1.83-2.00 (m, 2H), 2.05-2.30 (m, 10H), 2.78-2.87 (m, 1H), 2.90 (t, J=6.1 Hz, 2H), 2.94-3.03 (m, 2H), 3.04 (s, 3H), 3.15 (t, J=6.1 Hz, 2H), 6.67 (dd, J=9.5, 0.5 Hz, 1H), 6.88-7.07 (m, 2H), 7.17 (s, 2H), 7.40 (d, J=2.0 Hz, 1H), 7.44-7.56 (m, 2H).

Example 30

5-[2-(1-cyclopropyl-4-piperidinyl)-5-(2,4-difluorophenyl)-1,3-oxazol-4-yl]-1-(2,6-dimethylphenyl)-2(1H)-pyridinone Under an atmosphere of argon, to a solution of the compound prepared in Example 20(6) (100 mg) in methanol (12 mL) were added (1-ethoxycyclopropoxy)trimethylsilane (0.26 mL), sodium cyanoborohydride (68 mg) and acetic acid (0.12 mL) and the mixture was heated to reflux for 3.5 hours. The reaction mixture was poured into iced 2 N aqueous sodium hydroxide, then extracted with ethyl acetate. The obtained organic layer was washed with brine, dried and concentrated. The obtained residue was purified by column chromatography on silica gel (hexane:ethyl acetate=1:1→0:1→ethyl acetate:methanol=20:1→ethyl acetate:methanol:water=8:2:0.1) to give the compound of the present invention (108 mg) having the following physical data.

TLC: Rf 0.84 (dichloromethane:methanol:water=80:20:1); NMR: δ 7.54-7.44 (m, 3H), 7.27-7.12 (m, 3H), 7.03-6.87 (m, 2H), 6.67 (dd, J=9.6, 0.6 Hz, 1H), 3.16-3.02 (m, 2H), 2.85 (m, 1H), 2.40-2.23 (m, 2H), 2.16-1.98 (m, 2H), 2.10 (s, 6H), 1.98-1.80 (m, 2H), 1.63 (m, 1H), 0.52-0.38 (m, 4H).

Example 31

5-(5-(2,4-difluorophenyl)-2-{1-[(dimethylamino)acetyl]-4-piperidinyl}-1,3-oxazol-4-yl)-1-(2,6-dimethylphenyl)-2(1H)-pyridinone To a solution of the compound prepared in Example 20(6) (144 mg) in N,N-dimethylformamide (3 mL) were added N,N-dimethylglycine (96 mg), hydroxybenzotriazole monohydrate (126 mg) and 1-ethyl-3-[3-dimethylaminopropyl]carbodiimide hydrochloride (EDC) (179 mg) and the mixture was stirred at room temperature for 5 hours. The reaction mixture was extracted with ethyl acetate, washed with saturated sodium hydrogen carbonate solution, water and brine sequentially, dried and concentrated. The obtained residue was purified by column chromatography on silica gel (ethyl acetate→ethyl acetate:methanol (19:1→9:1)→ethyl acetate:

methanol:triethylamine (9:1:0.3)) to give the compound of the present invention (141 mg) having the following physical data.

TLC: Rf 0.49 (dichloromethane:methanol:ammonia water=4:1:0.1); NMR: δ 1.71-2.01 (m, 2H), 2.06-2.19 (m, 8H), 2.29 (s, 6H), 2.83-2.99 (m, 1H), 3.02-3.29 (m, 4H), 4.10-4.23 (m, 1H), 4.42-4.56 (m, 1H), 6.67 (dd, J=9.33, 0.91 Hz, 1H), 6.89-7.04 (m, 2H), 7.14-7.28 (m, 3H), 7.44-7.54 (m, 3H).

Example 31(1)

1-(4-chloro-2,6-dimethylphenyl)-5-(5-(2,4-difluorophenyl)-2-{1-[(dimethylamino)acetyl]-4-piperidinyl}-1,3-oxazol-4-yl)-2(1H)-pyridinone By the same procedure as a reaction of Example 31, using the compound prepared in Example 20(8) instead of the compound prepared in Example 20(6), the compound of the present invention having the following physical data was obtained.

TLC: Rf 0.49 (dichloromethane:methanol:ammonia water=90:10:1); NMR: δ 1.73-1.99 (m, 2H), 2.02-2.21 (m, 8H), 2.30 (s, 6H), 2.84-2.99 (m, 1H), 3.01-3.33 (m, 4H), 4.08-4.24 (m, 1H), 4.41-4.58 (m, 1H), 6.67 (dd, J=9.51, 0.73 Hz, 1H), 6.88-7.05 (m, 2H), 7.17 (s, 2H), 7.42 (d, J=2.01 Hz, 1H), 7.44-7.55 (m, 2H).

Example 32

5-[5-(2,4-difluorophenyl)-2-(1-phenyl-4-piperidinyl)-1,3-oxazol-4-yl]-1-(2,6-dimethylphenyl)-2(1H)-pyridinone To a solution of the compound prepared in Example 20(6) (102 mg) in dichloromethane (6 mL) were added phenylboric acid (54 mg), cupric acetate (II) monohydrate (88 mg) and molecular sieves 4A (100 mg) and the mixture was stirred at 40° C. and concentrated. The obtained residue was purified by preparative TLC (hexane:ethyl acetate=2:3→toluene:ethyl acetate=3:2) to give the compound of the present invention (13 mg) having the following physical data.

TLC: Rf 0.23 (hexane:ethyl acetate=1:1); NMR: δ 1.98-2.28 (m, 10H), 2.83-3.08 (m, 3H), 3.67-3.79 (m, 2H), 6.68 (dd, J=9.5, 0.7 Hz, 1H), 6.81-7.06 (m, 5H), 7.13-7.20 (m, 2H), 7.20-7.32 (m, 3H), 7.45-7.58 (m, 3H).

Example 33

5-{5-(2,4-difluorophenyl)-2-[1-(2-pyridinyl)-4-piperidinyl]-1,3-oxazol-4-yl}-1-(2,6-dimethylphenyl)-2(1H)-pyridinone To a solution of the compound prepared in Example 20(6) (101 mg) in N,N-dimethylformamide (1 mL) were added 2-fluoropyridine (43 mg) and calcium carbonate (91 mg) and the mixture was microwaved (150 W, 200° C.) for 1 hour. The reaction mixture was added by water, then extracted with ethyl acetate. The obtained organic layer was dried and concentrated. The obtained residue was purified by preparative TLC (dichloromethane:methanol:triethylamine=100:10:1) to give the compound of the present invention (23 mg) having the following physical data.

TLC: Rf 0.67 (dichloromethane:methanol:triethylamine=60:10:1); NMR: δ 1.89-2.28 (m, 10H), 2.99-3.19 (m, 3H), 4.24-4.40 (m, 2H), 6.55-6.75 (m, 3H), 6.87-7.06 (m, 2H), 7.12-7.20 (m, 2H), 7.20-7.31 (m, 2H), 7.43-7.57 (m, 3H), 8.19 (dd, J=4.8, 1.2 Hz, 1H).

Example 34

5-(5-(2,4-difluorophenyl)-2-{1-[2-hydroxy-1-(hydroxymethyl)ethyl]-4-piperidinyl}-1,3-oxazol-4-yl)-1-(4-fluoro-2,6-dimethylphenyl)-2(1H)-pyridinone To a solution of the compound prepared in Example 20(7) (249 mg) were added methyl 1,3-dioxolan-5-one (101 mg) and titanium (IV) tetraisopropoxide (295 mg) and the mixture was stirred at room temperature for 5 hours. The reaction mixture was added by sodium triacetoxyborohydride (329 mg), stirred and concentrated. The obtained residue was added by sodium acetate and water, then extracted with ethyl acetate. The obtained organic layer was dried and concentrated. The obtained residue was purified by preparative TLC (dichloromethane:methanol:triethylamine=60:6:1) to give the acetonide compound (92 mg). To a solution of thus obtained acetonide compound (92 mg) in tetrahydrofuran (6 mL) was added 5 N hydrochloric acid (1 mL) and the mixture was stirred at room temperature. The reaction mixture was added by sodium hydrogen carbonate solution, then extracted with ethyl acetate. The obtained organic layer was dried and concentrated. The obtained residue was purified by preparative TLC (dichloromethane:methanol:triethylamine=60:6:1) to give the compound of the present invention (46 mg) having the following physical data.

TLC: Rf 0.52 (dichloromethane:methanol:triethylamine=60:10:1); NMR: δ 1.79-2.00 (m, 2H), 2.06-2.19 (m, 8H), 2.60-2.73 (m, 2H), 2.77-2.94 (m, 2H), 2.95-3.06 (m, 2H), 3.59-3.71 (m, 4H), 6.65 (d, J=9.5 Hz, 1H), 6.83-7.05 (m, 4H), 7.42 (d, J=2.0 Hz, 1H), 7.44-7.55 (m, 2H).

Example 34(1)

1-(4-chloro-2,6-dimethylphenyl)-5-(5-(2,4-difluorophenyl)-2-{1-[2-hydroxy-1-(hydroxymethyl)ethyl]-4-piperidinyl}-1,3-oxazol-4-yl)-2(1H)-pyridinone By the same procedure as a reaction of Example 34, using the compound prepared in Example 20(8) instead of the compound prepared in Example 20(7), the compound of the present invention having the physical data was obtained.

TLC: Rf 0.46 (dichloromethane:methanol:triethylamine=60:10:1); NMR: δ 1.79-2.22 (m, 10H), 2.61-2.76 (m, 2H), 2.78-2.95 (m, 2H), 2.96-3.08 (m, 2H), 3.56-3.77 (m, 4H), 6.67 (d, J=9.7 Hz, 1H), 6.87-7.06 (m, 2H), 7.17 (s, 2H), 7.41 (d, J=2.4 Hz, 1H), 7.46-7.57 (m, 2H).

Example 35

1-(4-chloro-2,6-dimethylphenyl)-5-{5-(2,4-difluorophenyl)-2-[(2R)-2-pyrrolidinyl]-1,3-oxazol-4-yl}-2(1H)-pyridinone By the same procedure as a series of reactions of Example 5→Example 6→Example 12→Example 7→Example 17→Example 18, using coumaric acid instead of the compound prepared in Example 4 used in the reaction of Example 5, 2,4-difluorobenzyl bromide instead of 2-chloro-4-fluorobenzyl bromide used in the reaction of Example 6, 2,6-dimethyl-4-chloroaniline instead of 2,6-difluoroaniline used in the reaction of Example 12, and the sodium salts of corresponding carboxylic acids instead of sodium N-Boc-isonipecotate used in the reaction of Example 17, the compound of the present invention having the following physical data was obtained.

TLC: Rf 0.50 (dichloromethane:methanol=9:1); NMR: δ 1.81-2.04 (m, 2H), 2.03-2.35 (m, 8H), 2.98-3.11 (m, 1H), 3.11-3.26 (m, 1H), 4.37 (dd, J=7.8, 6.1 Hz, 1H), 6.66 (d, J=9.5 Hz, 1H), 6.85-7.06 (m, 2H), 7.12-7.21 (m, 2H), 7.38-7.59 (m, 3H).

Example 35(1)-Example 35(15)

By the same procedure as a reaction of Example 35, using the corresponding aniline compounds instead of 2,6-difluoroaniline and the sodium salts of corresponding carboxylic acids instead of sodium N-Boc-isonipecotate, the compounds of the present invention having the following physical data were obtained.

Example 35(1)

1-(4-chloro-2,6-dimethylphenyl)-5-[5-(2,4-difluorophenyl)-2-(2-pyrrolidinyl)-1,3-oxazol-4-yl]-2(1H)-pyridinone TLC: Rf 0.37 (dichloromethane:methanol:triethylamine=300:10:3); NMR: δ 1.78-2.34 (m, 10H), 2.97-3.11 (m, 1H), 3.12-3.24 (m, 1H), 4.37 (dd, J=8.0, 6.1 Hz, 1H), 6.65 (dd, J=9.5, 0.7 Hz, 1H), 6.87-7.06 (m, 2H), 7.17 (s, 2H), 7.41-7.58 (m, 3H).

Example 35(2)

1-(2,6-difluorophenyl)-5-{5-(2,4-difluorophenyl)-2-[(2S)-2-piperidinyl]-1,3-oxazol-4-yl}-2(1H)-pyridinone TLC: Rf 0.33 (dichloromethane:methanol=9:1); NMR: δ 1.48-1.97 (m, 5H), 2.04-2.16 (m, 1H), 2.73-2.85 (m, 1H), 3.14-3.25 (m, 1H), 3.95 (dd, J=10.25, 3.11 Hz, 1H), 6.61 (dd, J=9.70, 0.73 Hz, 1H), 6.90-7.12 (m, 4H), 7.35-7.57 (m, 3H), 7.67-7.72 (m, 1H).

Example 35(3)

1-(2,6-difluorophenyl)-5-{5-(2,4-difluorophenyl)-2-[(2R)-2-piperidinyl]-1,3-oxazol-4-yl}-2(1H)-pyridinone TLC: Rf 0.33 (dichloromethane:methanol=9:1); NMR: δ 1.44-1.96 (m, 5H), 2.03-2.14 (m, 1H), 2.72-2.83 (m, 1H), 3.13-3.23 (m, 1H), 3.93 (dd, J=10.34, 3.02 Hz, 1H), 6.60 (d, J=9.70 Hz, 1H), 6.87-7.13 (m, 4H), 7.34-7.56 (m, 3H), 7.68 (d, J=1.83 Hz, 1H).

Example 35(4)

1-(4-chloro-2,6-dimethylphenyl)-5-[5-(2,4-difluorophenyl)-2-(2-piperidinyl)-1,3-oxazol-4-yl]-2(1H)-pyridinone TLC: Rf 0.38 (ethyl acetate:triethylamine=19:1); NMR: δ 1.48-1.59 (m, 2H), 1.62-1.80 (m, 2H), 1.85-1.96 (m, 1H), 2.03-2.15 (m, 8H), 2.73-2.84 (m, 1H), 3.14-3.23 (m, 1H), 3.94 (dd, J=10.4, 3.1 Hz, 1H), 6.62-6.67 (m, 1H), 6.88-7.05 (m, 2H), 7.16 (s, 2H), 7.45-7.56 (m, 3H).

Example 35(5)

1-(4-chloro-2,6-dimethylphenyl)-5-{5-(2,4-difluorophenyl)-2-[(2R)-2-piperidinyl]-1,3-oxazol-4-yl}-2(1H)-pyridinone TLC: Rf 0.48 (dichloromethane:methanol=9:1); NMR: δ 1.44-1.97 (m, 4H), 2.00-2.17 (m, 8H), 2.70-2.85 (m, 1H), 3.11-3.25 (m, 1H), 3.93 (dd, J=10.34, 3.02 Hz, 1H), 6.63 (d, J=10.25 Hz, 1H), 6.86-7.04 (m, 2H), 7.15 (s, 2H), 7.44-7.56 (m, 3H).

Example 35(6)

1-(4-chloro-2,6-dimethylphenyl)-5-{5-(2,4-difluorophenyl)-2-[(3R)-1,2,3,4-tetrahydro-3-isoquinolinyl]-1,3-oxazol-4-yl}-2(1H)-pyridinone TLC: Rf 0.46 (hexane:ethyl acetate=1:4); NMR: δ 2.08 (s, 6H), 3.14-3.33 (m, 2H), 4.14-4.28 (m, 2H), 4.33 (dd, J=8.0, 6.9 Hz, 1H), 6.61-6.73 (m, 1H), 6.89-7.12 (m, 3H), 7.12-7.23 (m, 5H), 7.46-7.60 (m, 3H).

Example 35(7)

1-(4-chloro-2,6-dimethylphenyl)-5-[5-(2,4-difluorophenyl)-2-(3-piperidinyl)-1,3-oxazol-4-yl]-2(1H)-pyridinone TLC: Rf 0.42 (dichloromethane:methanol:triethylamine=60:10:1); NMR: δ 1.49-2.28 (m, 10H), 2.67-2.81 (m, 1H), 2.94-3.13 (m, 3H), 3.31-3.46 (m, 1H), 6.66 (d, J=9.5 Hz, 1H), 6.88-7.06 (m, 2H), 7.17 (s, 2H), 7.41 (d, J=2.6 Hz, 1H), 7.45-7.56 (m, 2H).

Example 35(8)

1-(4-chloro-2,6-dimethylphenyl)-5-[5-(2,4-difluorophenyl)-2-(3-piperidinyl)-1,3-oxazol-4-yl]-2(1H)-pyridinone TLC: Rf 0.42 (dichloromethane:methanol:triethylamine=60:10:1); NMR: δ 1.48-2.28 (m, 10H), 2.65-2.83 (m, 1H), 2.94-3.13 (m, 3H), 3.30-3.47 (m, 1H), 6.66 (d, J=9.5 Hz, 1H), 6.87-7.07 (m, 2H), 7.17 (s, 2H), 7.41 (d, J=2.4 Hz, 1H), 7.45-7.58 (m, 2H).

Example 35(9)

1-(4-chloro-2,6-dimethylphenyl)-5-[5-(2,4-difluorophenyl)-2-(1,2,5,6-tetrahydro-3-pyridinyl)-1,3-oxazol-4-yl]-2(1H)-pyridinone TLC: Rf 0.44 (dichloromethane:methanol:triethylamine=60:10:1); NMR: δ 2.09 (s, 6H), 2.31-2.43 (m, 2H), 3.07 (t, J=5.6 Hz, 2H), 3.79-3.89 (m, 2H), 6.67 (d, J=9.5 Hz, 1H), 6.85-7.08 (m, 3H), 7.17 (s, 2H), 7.43 (d, J=2.0 Hz, 1H), 7.47-7.58 (m, 2H).

Example 35(10)

5-[5-(2,4-difluorophenyl)-2-(2-morpholinyl)-1,3-oxazol-4-yl]-1-(2,6-dimethylphenyl)-2(1H)-pyridinone TLC: Rf 0.56 (dichloromethane:methanol:ammonia water=90:10:1); NMR: δ 2.10 (s, 6H), 2.87-2.96 (m, 1H), 2.96-3.09 (m, 1H), 3.15-3.26 (m, 1H), 3.26-3.35 (m, 1H), 3.71-3.85 (m, 1H), 3.97-4.06 (m, 1H), 4.73 (dd, J=9.1, 3.0 Hz, 1H), 6.66 (d, J=9.5 Hz, 1H), 6.87-7.07 (m, 2H), 7.12-7.19 (m, 2H), 7.20-7.29 (m, 1H), 7.45-7.60 (m, 3H).

Example 35(11)

1-(4-chloro-2,6-dimethylphenyl)-5-[5-(2,4-difluorophenyl)-2-(3-morpholinyl)-1,3-oxazol-4-yl]-2(1H)-pyridinone TLC: Rf 0.52 (dichloromethane:methanol=10:1); NMR: δ 7.55-7.45 (m, 3H), 7.17 (s, 2H), 7.05-6.90 (m, 2H), 6.65 (d, J=10.5 Hz, 1H), 4.22-4.10 (m, 2H), 3.90-3.78 (m, 2H), 3.67 (m, 1H), 3.14-2.98 (m, 2H), 2.08 (s, 6H), 1.62 (brs, 1H).

Example 35(12)

1-(4-chloro-2,6-dimethylphenyl)-5-[5-(2,4-difluorophenyl)-2-(1,1-dioxide-3-thiomorpholinyl)-1,3-oxazol-4-yl]-2(1H)-pyridinone TLC: Rf 0.42 (dichloromethane:methanol:triethylamine=160:8:3); NMR: δ 2.07 (s, 6H), 3.04-3.15 (m, 2H), 3.28 (dd, J=13.8, 11.1 Hz, 1H), 3.36-3.63 (m, 3H), 4.57 (dd, J=11.1, 2.7 Hz, 1H), 6.61-6.70 (m, 1H), 6.89-7.08 (m, 2H), 7.16 (s, 2H), 7.40-7.55 (m, 3H).

Example 35(13)

1-(4-chloro-2,6-dimethylphenyl)-5-[5-(2,4-difluorophenyl)-2-(1,3-thiazolidin-4-yl)-1,3-oxazol-4-yl]-2(1H)-pyridinone TLC: Rf 0.46 (dichloromethane:methanol:triethylamine=90:10:1); NMR: δ 2.08 (s, 6H), 3.21 (dd, J=10.6, 7.0 Hz, 1H), 3.37 (dd, J=10.6, 7.0 Hz, 1H), 4.23-4.44 (m, 2H), 4.52 (t, J=7.0 Hz, 1H), 6.63-6.70 (m, 1H), 6.89-7.07 (m, 2H), 7.17 (s, 2H), 7.45-7.57 (m, 3H).

Example 35(14)

5-[2-(4-aminotetrahydro-2H-pyran-4-yl)-5-(2,4-difluorophenyl)-1,3-oxazol-4-yl]-1-(4-chloro-2,6-dimethylphenyl)-2(1H)-pyridinone TLC: Rf 0.56 (ethyl acetate:methanol=10:1); NMR: δ 7.55-7.47 (m, 2H), 7.43 (dd, J=2.1, 0.6 Hz, 1H), 7.18 (s, 2H), 7.06-6.90 (m, 2H), 6.68 (dd, J=9.6, 0.6 Hz, 1H), 4.00-3.92 (m, 2H), 3.74-3.67 (m, 2H), 2.38-2.29 (m, 2H), 2.09 (s, 6H), 1.85-1.70 (m, 2H), 1.62 (brs, 2H).

Example 35(15)

5-[2-(4-amino-1,1-dioxidetetrahydro-2H-thiopyran-4-yl)-5-(2,4-difluorophenyl)-1,3-oxazol-4-yl]-1-(4-chloro-2,6-dimethylphenyl)-2(1H)-pyridinone TLC: Rf 0.70 (dichloromethane:methanol:triethylamine=90:10:1); NMR: δ 2.09 (s, 6H), 2.23-2.39 (m, 2H), 2.68-2.84 (m, 2H), 2.93-3.07 (m, 2H), 3.44-3.60 (m, 2H), 6.67 (dd, J=9.5, 0.7 Hz, 1H), 6.91-7.09 (m, 2H), 7.19 (s, 2H), 7.41-7.55 (m, 3H).

Example 36

1-(4-chloro-2,6-dimethylphenyl)-5-{5-(2,4-difluorophenyl)-2-[(2R)-1-methyl-2-pyrrolidinyl]-1,3-oxazol-4-yl}-2(1H)-pyridinone By the same procedure as a reaction of Example 16, using the compound prepared in Example 35 instead of the compound prepared in Example 14, the compound of the present invention having the following physical data was obtained.

TLC: Rf 0.49 (dichloromethane:methanol=19:1); NMR: δ 1.81-1.96 (m, 1H), 1.97-2.12 (m, 7H), 2.12-2.33 (m, 2H), 2.32-2.51 (m, 4H), 3.14-3.30 (m, 1H), 3.49 (t, J=8.0 Hz, 1H), 6.58-6.71 (m, 1H), 6.84-7.07 (m, 2H), 7.10-7.20 (m, 2H), 7.41-7.62 (m, 3H).

Example 36(1)-Example 36(6)

By the same procedure as a reaction of Example 36, using the compounds prepared in Example 35(1)-Example 35(6) instead of the compound prepared in Example 35, the compounds of the present invention having the following physical data were obtained.

Example 36(1)

1-(4-chloro-2,6-dimethylphenyl)-5-[5-(2,4-difluorophenyl)-2-[(2S)-1-methyl-2-pyrrolidinyl]-1,3-oxazol-4-yl]-2(1H)-pyridinone TLC: Rf 0.35 (dichloromethane:methanol:triethylamine=150:10:1); NMR: δ 1.81-2.33 (m, 10H), 2.33-2.46 (m, 4H), 3.16-3.28 (m, 1H), 3.49 (t, J=8.0 Hz, 1H), 6.59-6.68 (m, 1H), 6.86-7.05 (m, 2H), 7.15 (s, 2H), 7.43-7.60 (m, 3H).

Example 36(2)

1-(2,6-difluorophenyl)-5-{5-(2,4-difluorophenyl)-2-[(2S)-1-methyl-2-piperidinyl]-1,3-oxazol-4-yl}-2(1H)-pyridinone TLC: Rf 0.36 (dichloromethane:methanol=9:1); NMR: δ 1.30-1.46 (m, 1H), 1.66-1.78 (m, 2H), 1.79-1.97 (m, 3H), 2.11-2.26 (m, 4H), 2.97-3.08 (m, 1H), 3.23-3.33 (m, 1H), 6.61 (d, J=9.70 Hz, 1H), 6.89-7.12 (m, 4H), 7.35-7.48 (m, 2H), 7.49-7.59 (m, 1H), 7.72-7.76 (m, 1H).

Example 36(3)

1-(2,6-difluorophenyl)-5-{5-(2,4-difluorophenyl)-2-[(2R)-1-methyl-2-piperidinyl]-1,3-oxazol-4-yl}-2(1H)-pyridinone TLC: Rf 0.36 (dichloromethane:methanol=9:1); NMR: δ 1.30-1.48 (m, 1H), 1.64-1.79 (m, 2H), 1.79-1.99 (m, 3H), 2.10-2.19 (m, 1H), 2.21 (s, 3H), 2.98-3.07 (m, 1H), 3.27 (dd, J=9.70, 3.84 Hz, 1H), 6.61 (d, J=9.70 Hz, 1H), 6.88-7.15 (m, 4H), 7.36-7.48 (m, 2H), 7.49-7.63 (m, 1H), 7.74 (d, J=2.56 Hz, 1H).

Example 36(4)

1-(4-chloro-2,6-dimethylphenyl)-5-[5-(2,4-difluorophenyl)-2-[(2S)-1-methyl-2-piperidinyl]-1,3-oxazol-4-yl]-2(1H)-pyridinone TLC: Rf 0.46 (ethyl acetate:triethylamine=19:1); NMR: δ 1.31-1.48 (m, 1H), 1.67-1.77 (m, 2H), 1.81-1.95 (m, 3H), 2.09 (s, 6H), 2.12-2.19 (m, 1H), 2.21 (s, 3H), 2.99-3.08 (m, 1H), 3.24-3.31 (m, 1H), 6.65 (dd, J=9.6, 0.8 Hz, 1H), 6.89-7.05 (m, 2H), 7.16 (s, 2H), 7.46-7.60 (m, 3H).

Example 36(5)

1-(4-chloro-2,6-dimethylphenyl)-5-{5-(2,4-difluorophenyl)-2-[(2R)-1-methyl-2-piperidinyl]-1,3-oxazol-4-yl}-2(1H)-pyridinone TLC: Rf 0.54 (dichloromethane:methanol=9:1); NMR: δ 1.29-1.49 (m, 1H), 1.66-1.79 (m, 2H), 1.79-1.99 (m, 3H), 2.09 (s, 6H), 2.12-2.25 (m, 4H), 2.97-3.08 (m, 1H), 3.22-3.33 (m, 1H), 6.65 (dd, J=9.51, 0.73 Hz, 1H), 6.88-7.06 (m, 2H), 7.16 (s, 2H), 7.45-7.62 (m, 3H).

Example 36(6)

1-(4-chloro-2,6-dimethylphenyl)-5-{5-(2,4-difluorophenyl)-2-[(3R)-2-methyl-1,2,3,4-tetrahydro-3-isoquinolinyl]-1,3-oxazol-4-yl}-2(1H)-pyridinone TLC: Rf 0.51 (hexane:ethyl acetate=1:4); NMR: δ 2.06-2.13 (m, 6H), 2.45 (s, 3H), 3.19 (dd, J=16.5, 4.8 Hz, 1H), 3.41 (dd, J=16.5, 8.4 Hz, 1H), 3.80 (d, J=15.6 Hz, 1H), 3.93-4.07 (m, 2H), 6.66 (d, J=9.5 Hz, 1H), 6.85-7.22 (m, 8H), 7.41-7.57 (m, 3H).

Example 37

1-(4-chloro-2,6-dimethylphenyl)-5-[5-(2,4-difluorophenyl)-2-(hydroxymethyl)-1,3-oxazol-4-yl]-2(1H)-pyridinone By the same procedure as a reaction of Example 35, using the sodium salt of corresponding carboxylic acid (however the deprotection reaction in final step has not been conducted), the compound of the present invention having the following physical data was obtained.

TLC: Rf 0.20 (ethyl acetate:hexane=7:3); NMR: δ 2.08 (s, 6H), 2.21-2.36 (m, 1H), 4.79 (s, 2H), 6.67 (d, J=10.43 Hz, 1H), 6.90-7.07 (m, 2H), 7.16-7.18 (m, 2H), 7.46-7.59 (m, 3H).

Example 37(1)-Example 37(8)

By the same procedure as a reactions of Example 37, using the sodium salts of corresponding carboxylic acids and the corresponding aniline compounds instead of 2,6-dimethyl-4-chloroaniline, the compounds of the present invention having the following physical data were obtained.

Example 37(1)

5-[2-(1-tert-butyl-4-piperidinyl)-5-(2,4-difluorophenyl)-1,3-oxazol-4-yl]-1-(4-fluoro-2,6-dimethylphenyl)-2(1H)-pyridinone TLC: Rf 0.31 (dichloromethane:methanol=10:1); NMR: δ 7.54-7.40 (m, 3H), 7.04-6.82 (m, 4H), 6.66 (dd, J=9.9, 0.6 Hz, 1H), 3.20-3.05 (m, 2H), 2.81 (m, 1H), 2.35-1.85 (m, 6H), 2.09 (s, 6H), 1.10 (s, 9H).

Example 37(2)

5-[2-(1-tert-butyl-4-piperidinyl)-5-(2,4-difluorophenyl)-1,3-oxazol-4-yl]-1-(4-chloro-2,6-dimethylphenyl)-2(1H)-pyridinone TLC: Rf 0.21 (dichloromethane:methanol=10:1); NMR: δ 7.55-7.46 (m, 2H), 7.41 (m, 1H), 7.16 (s, 2H), 7.04-6.88 (m, 2H), 6.66 (dd, J=9.6, 0.6 Hz, 1H), 3.20-3.05 (m, 2H), 2.80 (m, 1H), 2.30-1.82 (m, 6H), 2.08 (s, 6H), 1.10 (s, 9H).

Example 37(3)

5-[5-(2,4-difluorophenyl)-2-(1-methyl-1,2,3,6-tetrahydro-4-pyridinyl)-1,3-oxazol-4-yl]-1-(2,6-dimethylphenyl)-2(1H)-pyridinone TLC: Rf 0.32 (dichloromethane:methanol:triethylamine=50:5:1); NMR: δ 2.10 (s, 6H), 2.42 (s, 3H), 2.60-2.77 (m, 4H), 3.12-3.25 (m, 2H), 6.68 (dd, J=9.5, 0.7 Hz, 1H), 6.71-6.78 (m, 1H), 6.86-7.07 (m, 2H), 7.11-7.22 (m, 2H), 7.20-7.31 (m, 1H), 7.44-7.61 (m, 3H).

Example 37(4a)

5-[2-(1-aminocyclopropyl)-5-(2,4-difluorophenyl)-1,3-oxazol-4-yl]-1-(2,6-dimethylphenyl)-2(1H)-pyridinone

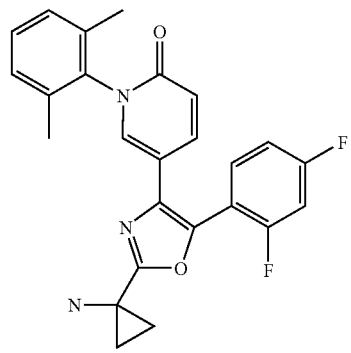

TLC: Rf 0.41 (dichloromethane:methanol=10:1); NMR: δ 7.53-7.42 (m, 3H), 7.28-7.14 (m, 3H), 7.02-6.88 (m, 2H), 6.68 (dd, J=9.3, 0.9 Hz, 1H), 2.11 (s, 6H), 1.70 (brs, 2H), 1.37-1.33 (m, 2H), 1.21-1.17 (m, 2H).

Example 37(4b)

5-[2-(1-aminocyclopropyl)-5-(2,4-difluorophenyl)-1H-imidazol-4-yl]-1-(2,6-dimethylphenyl)-2(1H)-pyridinone

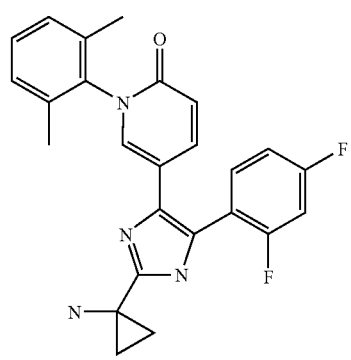

TLC: Rf 0.37 (dichloromethane:methanol=10:1); NMR: δ 7.55 (m, 1H), 7.39 (m, 1H), 7.26-7.10 (m, 4H), 6.94-6.82 (m, 2H), 6.64 (dd, J=9.6, 0.6 Hz, 1H), 2.05 (s, 6H), 1.70 (brs, 2H), 1.43-1.39 (m, 2H), 1.08-1.04 (m, 2H).

Example 37(5a)

5-{5-(2,4-difluorophenyl)-2-[1-(methylamino)cyclopropyl]-1,3-oxazol-4-yl}-1-(2,6-dimethylphenyl)-2(1H)-pyridinone TLC: Rf 0.41 (dichloromethane:methanol=10:1); NMR: δ 7.55-7.43 (m, 3H), 7.29-7.14 (m, 3H), 7.03-6.88 (m, 2H), 6.68 (dd, J=9.6, 0.6 Hz, 1H), 2.56 (s, 3H), 2.11 (s, 6H), 1.75 (brs, 1H), 1.35-1.30 (m, 2H), 1.20-1.15 (m, 2H).

Example 37(5b)

5-{5-(2,4-difluorophenyl)-2-[1-(methylamino)cyclopropyl]-1H-imidazol-4-yl}-1-(2,6-dimethylphenyl)-2(1H)-pyridinone TLC: Rf 0.28 (dichloromethane:methanol=10:1); NMR: δ 9.80 (brs, 1H), 7.57 (m, 1H), 7.40 (m, 1H), 7.32-7.10 (m, 4H), 6.96-6.82 (m, 2H), 6.66 (d, J=9.6 Hz, 1H), 2.43 (s, 3H), 2.07 (s, 6H), 1.65 (brs, 1H), 1.35-1.30 (m, 2H), 1.10-1.02 (m, 2H).

Example 37(6a)

5-{5-(2,4-difluorophenyl)-2-[1-(dimethylamino)cyclopropyl]-1,3-oxazol-4-yl}-1-(2,6-dimethylphenyl)-2(1H)-pyridinone TLC: Rf 0.44 (dichloromethane:methanol=10:1); NMR: δ 7.56-7.43 (m, 3H), 7.29-7.14 (m, 3H), 7.03-6.88 (m, 2H), 6.68 (dd, J=9.6, 0.6 Hz, 1H), 2.61 (s, 6H), 2.11 (s, 6H), 1.35-1.25 (m, 2H), 1.15-1.05 (m, 2H).

Example 37(6b)

5-{5-(2,4-difluorophenyl)-2-[1-(dimethylamino)cyclopropyl]-1H-imidazol-4-yl}-1-(2,6-dimethylphenyl)-2(1H)-pyridinone TLC: Rf 0.33 (dichloromethane:methanol=10:1); NMR: δ 9.43 (brs, 1H), 7.61 (m, 1H), 7.45-7.10 (m, 5H), 6.96-6.85 (m, 2H), 6.67 (m, 1H), 2.37 (s, 6H), 2.08 (s, 6H), 1.20-1.10 (m, 4H).

Example 37(7)

5-{5-(2,4-difluorophenyl)-2-[3-(4-morpholinyl)propyl]-1,3-oxazol-4-yl}-1-(2,6-dimethylphenyl)-2(1H)-pyridinone TLC: Rf 0.50 (dichloromethane:methanol=9:1); NMR: δ 1.93-2.06 (m, 2H), 2.10 (s, 6H), 2.39-2.53 (m, 6H), 2.85 (t, J=7.4 Hz, 2H), 3.63-3.72 (m, 4H), 6.67 (d, J=9.3 Hz, 1H), 6.87-7.06 (m, 2H), 7.12-7.20 (m, 2H), 7.20-7.30 (m, 1H), 7.43-7.56 (m, 3H).

Example 37(8)

5-[5-(2,4-difluorophenyl)-2-(4-hydroxycyclohexyl)-1,3-oxazol-4-yl]-1-(4-fluoro-2,6-dimethylphenyl)-2(1H)-pyridinone TLC: Rf 0.22 (ethyl acetate); NMR: δ 1.30-1.39 (m, 1H), 1.66-1.96 (m, 6H), 2.05-2.25 (m, 8H), 2.86-3.00 (m, 1H), 3.95-4.05 (m, 1H), 6.66 (d, J=9.70 Hz, 1H), 6.83-7.06 (m, 4H), 7.41-7.57 (m, 3H).

Example 38

1-(4-chloro-2,6-dimethylphenyl)-5-[5-(2,4-difluorophenyl)-2-(4-morpholinylmethyl)-1,3-oxazol-4-yl]-2(1H)-pyridinone To a solution of the compound prepared in Example 37 (40 mg) in dichloromethane (1.0 mL) were added triethylamine (30.2 μL) and methanesulfonyl chloride (15.4 μL) at 0° C. and the mixture was stirred for 2 hours. The reaction mixture was added by morpholine (78 mg), stirred at room temperature for 2 hours.

The reaction mixture was added by ethyl acetate, washed with water and brine, dried and concentrated. The obtained residue was purified by preparative TLC (ethyl acetate:methanol=50:1) to give the compound of the present invention (29 mg) having the following physical data.

TLC: Rf 0.29 (ethyl acetate); NMR: δ 2.08 (s, 6H), 2.59-2.66 (m, 4H), 3.69-3.81 (m, 6H), 6.66 (dd, J=9.06, 1.19 Hz, 1H), 6.90-7.07 (m, 2H), 7.17 (s, 2H), 7.45-7.58 (m, 3H).

Example 38(1)

1-(4-chloro-2,6-dimethylphenyl)-5-[5-(2,4-difluorophenyl)-2-(1-pyrrolidinylmethyl)-1,3-oxazol-4-yl]-2(1H)-pyridinone By the same procedure as a reaction of Example 38, using pyrrolidine instead of morpholine, the compound of the present invention having the following physical data was obtained.

TLC: Rf 0.40 (ethyl acetate); NMR: δ 1.80-1.89 (m, 4H), 2.08 (s, 6H), 2.64-2.76 (m, 4H), 3.83 (s, 2H), 6.65 (d, J=10.43 Hz, 1H), 6.88-7.06 (m, 2H), 7.16 (s, 2H), 7.46-7.63 (m, 3H).

Example 39

5-[5-(2,4-difluorophenyl)-2-(4-oxocyclohexyl)-1,3-oxazol-4-yl]-1-(4-fluoro-2,6-dimethylphenyl)-2(1H)-pyridinone Under an atmosphere of argon, oxalyl chloride (110 μL) was dissolved in dichloromethane (6 mL) and cooled at −78° C. The reaction mixture was added by a solution of dimethylsulfoxide (116 μL) in dichloromethane (0.5 mL) and the mixture was stirred for 10 minutes. The reaction mixture was added by a solution of the compound prepared in Example 37(8) (312 mg) in dichloromethane (2.0 mL) and the mixture was stirred at −78° C. for 15 minutes and at −45° C. for 1 hour. The reaction mixture was added by trimethylamine (638 μL) and the mixture was stirred at 0° C. for 20 minutes. The reaction mixture was added by ethyl acetate, washed with 1 N hydrochloric acid, saturated sodium hydrogen carbonate solution and brine, dried and concentrated. The obtained residue was purified by column chromatography on silica gel (hexane:ethyl acetate=1:4→0:1) to give the compound of the present invention (281 mg) having the following physical data.

TLC: Rf 0.37 (ethyl acetate); NMR: δ 2.10 (s, 6H), 2.14-2.32 (m, 2H), 2.35-2.64 (m, 6H), 3.26-3.38 (m, 1H), 6.67 (dd, J=9.51, 0.73 Hz, 1H), 6.85-7.06 (m, 4H), 7.43-7.56 (m, 3H).

Example 40

5-{5-(2,4-difluorophenyl)-2-[4-(4-morpholinyl)cyclohexyl]-1,3-oxazol-4-yl}-1-(4-fluoro-2,6-dimethylphenyl)-2(1H)-pyridinone (low polar compound: 40a) and 5-{5-(2,4-difluorophenyl)-2-[4-(4-morpholinyl)cyclohexyl]-1,3-oxazol-4-yl}-1-(4-fluoro-2,6-dimethylphenyl)-2(1H)-pyridinone (high polar compound: 40b)

To a solution of the compound prepared in Example 39 (50 mg) in dichloroethane (2.0 mL) were added morpholine (18 mg), acetic acid (29 μL) and sodium triacetoxyborohydride (64 mg) and the mixture was stirred at room temperature for 24 hours. The reaction mixture was added by ethyl acetate, washed with saturated sodium hydrogen carbonate solution and brine sequentially, dried and concentrated. The obtained residue was purified by preparative TLC (dichloromethane:methanol:ammonia water=9:1:0.1) to give the compounds of the present invention (40a: 32 mg, 40b: 22 mg) having the following physical data.

Compound 40a:
TLC: Rf 0.36 (dichloromethane:methanol:ammonia water=90:10:1); NMR: δ 1.61-1.85 (m, 6H), 2.10 (s, 6H), 2.16-2.40 (m, 3H), 2.44-2.60 (m, 4H), 3.03-3.15 (m, 1H), 3.64-3.78 (m, 4H), 6.67 (dd, J=9.61, 0.64 Hz, 1H), 6.84-7.05 (m, 4H), 7.41 (d, J=2.01 Hz, 1H), 7.45-7.57 (m, 2H).

Compound 40b:
TLC: Rf 0.32 (dichloromethane:methanol:ammonia water=90:10:1); NMR: δ 1.30-1.50 (m, 2H), 1.55-1.81 (m, 2H), 2.02-2.16 (m, 8H), 2.20-2.40 (m, 3H), 2.55-2.67 (m, 4H), 2.71-2.84 (m, 1H), 3.69-3.81 (m, 4H), 6.66 (dd, J=9.51, 0.73 Hz, 1H), 6.84-7.05 (m, 4H), 7.43 (d, J=2.01 Hz, 1H), 7.45-7.55 (m, 2H).

Example 41

5-(5-(2,4-difluorophenyl)-2-{4-[(2-methoxyethyl)amino]cyclohexyl}-1,3-oxazole-4-yl)-1-(4-fluoro-2,6-dimethylphenyl)-2(1H)-pyridinone (high polar compound: 41a) and 5-(5-(2,4-difluorophenyl)-2-{4-[(2-methoxyethyl)amino]cyclohexyl}-1,3-oxazol-4-yl)-1-(4-fluoro-2,6-dimethylphenyl)-2(1H)-pyridinone (low polar compound: 41b)

By the same procedure as a reaction of Example 40, using methoxyethylamine instead of morpholine, the compounds of the present invention having the following physical data were obtained.

Compound 41a:
TLC: Rf 0.26 (dichloromethane:methanol:triethylamine=90:10:1); NMR: δ 1.16-1.37 (m, 2H), 1.55-1.79 (m, 2H), 1.87-1.27 (m, 10H), 2.45-2.61 (m, 1H), 2.73-2.90 (m, 3H), 3.37 (s, 3H), 3.46-3.57 (m, 2H), 6.60-6.72 (m, 1H), 6.81-7.06 (m, 4H), 7.43 (d, J=2.0 Hz, 1H), 7.45-7.57 (m, 2H).

Compound 41b:
TLC: Rf 0.29 (dichloromethane:methanol:triethylamine=90:10:1); NMR: δ 1.45-1.66 (m, 2H), 1.69-1.94 (m, 4H), 2.10 (s, 6H), 2.18-2.34 (m, 2H), 2.63-2.74 (m, 1H), 2.75-2.83 (m, 2H), 2.98-3.12 (m, 1H), 3.35 (s, 3H), 3.46-3.53 (m, 2H), 6.66 (d, J=9.0 Hz, 1H), 6.84-7.05 (m, 4H), 7.42 (d, J=2.0 Hz, 1H), 7.44-7.55 (m, 2H).

Example 42 tert-butyl 4-{5-(2,4-difluorophenyl)-4-[1-(4-hydroxy-2,6-dimethylphenyl-6-oxo-1,6-dihydro-3-pyridinyl]-1,3-oxazol-2-yl}-1-piperidinecarboxylate By the same procedure as a series of reactions of Example 12→Example 7→Example 17→Example 18, using 2,6-dimethyl-4-hydroxyaniline instead of 2,6-difluoroaniline in Example 12 (however the deprotection reaction in final step has not been conducted), the compound of the present invention having the following physical data was obtained.

TLC: Rf 0.24 (hexane:ethyl acetate=1:4); NMR: δ 7.60 (m, 1H), 7.53-7.45 (m, 2H), 7.03-6.89 (m, 2H), 6.72 (d, J=9.3 Hz, 1H), 6.38 (s, 2H), 4.20-4.00 (m, 2H), 3.05-2.90 (m, 3H), 2.10-1.70 (m, 4H), 1.97 (s, 6H), 1.46 (s, 9H).

Example 42(1)

tert-butyl 4-[4-[1-(4-bromo-2,6-dimethylphenyl)-6-oxo-1,6-dihydro-3-pyridinyl]-5-(2,4-difluorophenyl)-1,3-oxazol-2-yl]-1-piperidinecarboxylate By the same procedure as a reaction of Example 42, using 2,6-dimethyl-4-bromoaniline instead of 2,6-dimethyl-4-hydroxyaniline, the compound of the present invention having the following physical data was obtained.

TLC: Rf 0.65 (hexane:ethyl acetate=1:2); NMR: δ 7.55-7.45 (m, 2H), 7.42-7.38 (m, 1H), 7.31 (s, 2H), 7.05-6.88 (m, 2H), 6.65 (dd, J=9.6, 0.3 Hz, 1H), 4.20-4.02 (m, 2H), 3.05-2.88 (m, 3H), 2.12-2.00 (m, 8H), 1.90-1.73 (m, 2H), 1.46 (s, 9H).

Example 43

5-[5-(2,4-difluorophenyl)-2-(4-piperidinyl)-1,3-oxazol-4-yl]-1-{4-[2-(dimethylamino)ethoxy]-2,6-dimethylphenyl}-2(1H)-pyridinone Under an atmosphere of argon, to a solution of the compound prepared in Example 42 (83 mg) in N,N-dimethylformamide (3 mL) were added N,N-dimethylaminoethyl chloride (31 mg) and potassium carbonate (60 mg) and the mixture was stirred at 100° C. for 5 hours. The reaction mixture was poured into ice, then extracted with ethyl acetate. The obtained organic layer was washed with brine, dried and concentrated. The obtained residue was purified by preparative TLC (dichloromethane: methanol=10:1) to give N-Boc compound (61 mg). To a solution of the N-Boc compound (61 mg) in methanol (0.5 mL) was added a solution of 4 N hydrogen chloride in ethyl acetate (2 mL) and the mixture was stirred for 20 minutes. The reaction mixture was poured into iced 5 N aqueous sodium hydroxide, then extracted with ethyl acetate. The obtained organic layer was washed with brine, dried and concentrated to give the compound of the present invention (40 mg) having the following physical data.

TLC: Rf 0.14 (ethyl acetate:acetic acid:water=3:1:1); NMR: δ 7.53-7.43 (m, 3H), 7.02-6.88 (m, 2H), 6.71 (s, 2H), 6.66 (dd, J=9.6, 0.6 Hz, 1H), 4.06 (t, J=5.7 Hz, 2H), 3.26-3.15 (m, 2H), 2.98 (m, 1H), 2.84-2.70 (m, 2H), 2.73 (t, J=5.7 Hz, 2H), 2.34 (s, 6H), 2.20-2.00 (m, 3H), 2.06 (s, 6H), 1.95-1.78 (m, 2H).

Example 43(1)

2-{4-[5-[5-(2,4-difluorophenyl)-2-(4-piperidinyl)-1,3-oxazol-4-yl]-2-oxo-1(2H)-pyridinyl]-3,5-dimethylphenoxy}-N,N-dimethylacetamide By the same procedure as a reaction of Example 43, using N,N-dimethylchloroacetamide instead of N,N-dimethylaminoethyl chloride, the compound of the present invention having the following physical data was obtained.

TLC: Rf 0.46 (dichloromethane:methanol:acetic acid=10:2:1); NMR: δ 7.54-7.43 (m, 3H), 7.03-6.88 (m, 2H), 6.74 (s, 2H), 6.66 (dd, J=9.6, 0.6 Hz, 1H), 4.68 (s, 2H), 3.24-3.13 (m, 2H), 3.10 (s, 3H), 3.00 (s, 3H), 2.98 (m, 1H), 2.83-2.70 (m, 2H), 2.16-1.76 (m, 5H), 2.06 (s, 6H).

Example 44

4-[5-[5-(2,4-difluorophenyl)-2-(4-piperidinyl)-1,3-oxazol-4-yl]-2-oxo-1(2H)-pyridinyl]-3,5-dimethylphenyl methanesulfonate Under an atmosphere of argon, to a solution of the compound prepared in Example 42 (80 mg) in pyridine (2 mL) was added methanesulfonyl chloride (13 μL) and the mixture was stirred for 2.5 hours. The reaction mixture was poured into iced 10% aqueous citric acid, then extracted with ethyl acetate. The obtained organic layer was washed with brine, dried and concentrated. The obtained residue was purified by preparative TLC (hexane:ethyl acetate=1:4) to give N-Boc compound (81 mg). To a solution of the N-Boc compound (80 mg) in methanol (0.5 mL) was added a solution of 4 N hydrogen chloride in ethyl acetate (2 mL) and the mixture was stirred for 30 minutes. The reaction mixture was poured into iced 1 N aqueous sodium hydroxide, then extracted with ethyl acetate. The obtained organic layer was washed with brine, dried and concentrated to give the compound of the present invention (43 mg) having the following physical data.

TLC: Rf 0.57 (dichloromethane:methanol:acetic acid=10:2:1); NMR: δ 7.55-7.44 (m, 3H), 7.11 (s, 2H), 7.05-6.90 (m, 2H), 6.67 (dd, J=9.6, 0.6 Hz, 1H), 3.26-3.14 (m, 2H), 3.20 (s, 3H), 2.98 (m, 1H), 2.84-2.70 (m, 2H), 2.24-1.76 (m, 5H), 2.13 (s, 6H).

Example 45

5-[5-(2,4-difluorophenyl)-2-(4-piperidinyl)-1,3-oxazol-4-yl]-1-[2,6-dimethyl-4-(4-morpholinyl)phenyl]-2(1H)-pyridinone To a solution of the compound prepared in Example 42(1) (383 mg) in toluene (6 mL) were added morpholine (63 μL), sodium tert-butoxide (86 mg), tris(bibenzylideneacetone)dipalladium(0) (Pd$_2$(dba)$_3$, 5.5 mg) and (±)-2,2'-bis(diphenylphosphino)-1,1'-binaphthyl (BINAP, 11 mg) and the mixture was stirred at 100° C. for 1 hour. The reaction mixture was added by Pd$_2$(dba)$_3$ (55 mg) and BINAP (112 mg), then stirred at 100° C. for 3 hours. Moreover, the reaction mixture was added by morpholine (63 μL), sodium tert-butoxide (86 mg), Pd$_2$(dba)$_3$ (55 mg) and BINAP (112 mg), then stirred overnight at 100° C. The reaction mixture was poured into iced water, filtrated with Celite (proprietary name) to remove an insoluble matter, and washed ethyl acetate. The filtrate and wash fraction were combined. The obtained organic layer was washed with 1 N hydrochloric acid, saturated sodium hydrogen carbonate solution and brine sequentially, dried and concentrated. The obtained residue was purified by preparative medium pressure liquid chromatography W-prep 2XY (column: main column L, inject column M; automatic condition setting: hexane:ethyl acetate:1:2, Rf=0.30, preparative isolation mode GR) to give the Boc compound (86 mg). To a solution of the Boc compound (80 mg) in ethyl acetate (2 mL) was added a solution of 4 N hydrogen chloride in ethyl acetate (2 mL) and the mixture was stirred at room temperature for 2 hours. The reaction mixture was poured into iced water, and added by ethyl acetate. The reaction mixture was added by 1 N aqueous sodium hydroxide to alkalify, then extracted with ethyl acetate. The obtained organic layer was washed with brine, dried and concentrated to give the compound of the present invention (62 mg) having the following physical data.

TLC: Rf 0.42 (dichloromethane:methanol:ammonia water=90:10:1); NMR: δ 1.72-1.93 (m, 2H), 1.94-2.21 (m, 8H), 2.67-2.84 (m, 2H), 2.88-3.05 (m, 1H), 3.10-3.28 (m, 6H), 3.78-3.90 (m, 4H), 6.60-6.72 (m, 3H), 6.81-7.03 (m, 2H), 7.36-7.57 (m, 3H).

Example 46 benzyl 1-(2,6-dimethylphenyl)-6-oxo-1,4,5,6-tetrahydro-3-pyridinecarboxylate

By the same procedure as a series of reactions of Example 1→Example 2, using benzyl 5-[(2,6-dimethylphenyl)amino]-5-oxopentanoate instead of ethyl 5-[(2,6-dichlorophenyl)amino]-5-oxopentanoate, the compound of the present invention having the following physical data was obtained.

TLC: Rf 0.61 (hexane:ethyl acetate=1:1); NMR: δ 2.14 (s, 6H), 2.71-2.87 (m, 4H), 5.18 (s, 2H), 7.06-7.14 (m, 2H), 7.14-7.23 (m, 2H), 7.28-7.45 (m, 5H).

Example 47

1-(2,6-dimethylphenyl)-6-oxo-1,4,5,6-tetrahydro-3-pyridinecarboxylic acid

To a solution of the compound prepared in Example 46 (4.77 g) in ethanol (140 mL) was added 5% palladium/carbon (0.5 g) and the mixture was stirred at room temperature for 2 hours under an atmosphere of hydrogen. The reaction mixture was filtrated with Celite (proprietary name) and the filtrate was concentrated to give the compound of the present invention (2.93 g) having the following physical data.

NMR: δ 2.16 (s, 6H), 2.75-2.84 (m, 4H), 7.08-7.16 (m, 2H), 7.17-7.25 (m, 1H), 7.28 (s, 1H).

Example 48

5-[5-(2,4-difluorophenyl)-2-(4-piperidinyl)-1,3-oxazol-4-yl]-1-(2,6-dimethylphenyl)-3,4-dihydro-2(1H)-pyridinone By the same procedure as a series of reactions of Example 5→Example 6→Example 7→Example 17→Example 18, using the compound prepared in Example 47 instead of the compound prepared in Example 4 used in the reaction of Example 5 and 2,4-difluorobenzyl bromide instead of 2-chloro-4-fluorobenzyl bromide used in the reaction of Example 6, the compound of the present invention having the following physical data was obtained.

TLC: Rf 0.25 (dichloromethane:methanol:triethylamine=60:10:1); NMR: δ 1.68-1.90 (m, 2H), 1.97-2.10 (m, 2H), 2.18 (s, 6H), 2.52-2.64 (m, 2H), 2.65-2.80 (m, 4H), 2.84-3.00 (m, 1H), 3.09-3.23 (m, 2H), 6.55 (s, 1H), 6.84-7.02 (m, 2H), 7.05-7.20 (m, 3H), 7.36-7.49 (m, 1H).

Example 49

5-[5-(2,4-difluorophenyl)-2-(1-methyl-4-piperidinyl)-1,3-oxazol-4-yl]-1-(2,6-dimethylphenyl)-3,4-dihydro-2(1H)-pyridinone By the same procedure as a reaction of Example 16, using the compound prepared in Example 48 instead of the compound prepared in Example 14, the compound of the present invention having the following physical data was obtained.

TLC: Rf 0.38 (dichloromethane:methanol:triethylamine=60:10:1); NMR: δ 1.84-2.15 (m, 6H), 2.18 (s, 6H), 2.31 (s, 3H), 2.54-2.64 (m, 2H), 2.67-2.84 (m, 3H), 2.84-2.97 (m, 2H), 6.51-6.59 (m, 1H), 6.86-7.03 (m, 2H), 7.06-7.21 (m, 3H), 7.37-7.50 (m, 1H).

Example 50 methyl 1-(2,6-dimethylphenyl)-6-oxo-1,6-dihydro-3-pyridinecarboxylate

By the same procedure as a series of reactions of Example 1→Example 2→Example 3, using methyl 5-[(2,6-dimethylphenyl)amino]-5-oxopentanoate instead of ethyl 5-[(2,6-dichlorophenyl)amino]-5-oxopentanoate, the compound of the present invention having the following physical data was obtained.

TLC: Rf 0.39 (hexane:ethyl acetate=1:1); NMR: δ 2.10 (s, 6H), 3.86 (s, 3H), 6.69 (dd, J=9.3, 0.9 Hz, 1H), 7.14-7.24 (m, 2H), 7.24-7.32 (m, 1H), 7.90-8.04 (m, 2H).

Example 51 methyl 1-(2,6-dimethylphenyl)-6-oxo-3-piperidinecarboxylate

Under an atmosphere of argon, to a solution of the compound prepared in Example 50 (100 mg) in methanol (4 mL) was added 5% palladium/carbon (wet, 20 mg) and the mixture was stirred for 15 hours under an atmosphere of hydrogen. The reaction mixture was filtrated with Celite (proprietary name) and the filtrate was concentrated. The obtained residue was purified by column chromatography on silica gel (hexane:ethyl acetate=2:1→1:1→1:4→0:1→ethyl acetate:methanol=10:1) to give the compound of the present invention (94 mg) having the following physical data.

TLC: Rf 0.10 (hexane:ethyl acetate=1:1); NMR: δ 7.18-7.05 (m, 3H), 3.74 (s, 3H), 3.71 (m, 1H), 3.54 (ddd, J=12.6, 5.7, 1.5 Hz, 1H), 3.02 (m, 1H), 2.76-2.54 (m, 2H), 2.34-2.11 (m, 2H), 2.20 (s, 3H), 2.19 (s, 3H).

Example 52

5-[5-(2,4-difluorophenyl)-2-(1-methyl-4-piperidinyl)-1,3-oxazol-4-yl]-1-(2,6-dimethylphenyl)-2-piperidinone

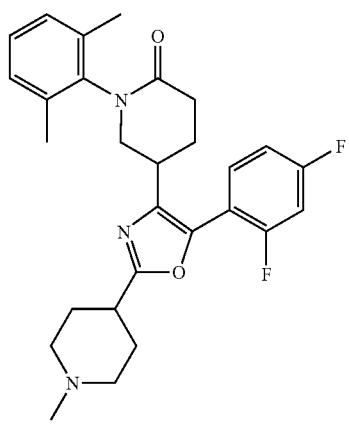

By the same procedure as a series of reactions of Example 4→Example 5→Example 6→Example 7→Example 17→Example 18→Example 16, using the compound prepared in Example 51 instead of the compound prepared in Example 3 used in the reaction of Example 4 and 2,4-difluorobenzyl bromide instead of 2-chloro-4-fluorobenzyl bromide used in the reaction of Example 6, the compound of the present invention having the following physical data was obtained.

TLC: Rf 0.47 (dichloromethane:methanol:water=80:20:1); NMR: δ 7.45 (m, 1H), 7.14-6.92 (m, 5H), 3.85 (t, J=11.1 Hz, 1H), 3.40-3.21 (m, 2H), 2.96-2.70 (m, 4H), 2.61 (m, 1H), 2.42-1.88 (m, 8H), 2.32 (s, 3H), 2.27 (s, 3H), 2.19 (s, 3H).

Example 53

1-(2,6-dimethylphenyl)-6-oxo-1,6-dihydro-3-pyridinecarboxylic acid

By the same procedure as a reaction of Example 4, using the compound prepared in Example 50 instead of the compound prepared in Example 3, the compound of the present invention having the following physical data was obtained.

NMR: δ 2.11 (s, 6H), 6.74 (d, J=9.5 Hz, 1H), 7.15-7.23 (m, 2H), 7.24-7.34 (m, 1H), 7.99 (dd, J=9.5, 2.7 Hz, 1H), 8.08 (dd, J=2.7 Hz, 1H).

Example 54 ethyl [1-(2,6-dimethylphenyl)-6-oxo-1,6-dihydro-3-pyridinyl]acetate

To a solution of the compound prepared in Example 53 (4.11 g) in dichloromethane (80 mL) was added oxalyl chloride (3.22 g). Stirring continually, N,N-dimethylformamide (0.3 mL) was dropped thereto, and the mixture was stirred for 30 minutes and concentrated. To a solution of obtained residue in tetrahydrofuran (80 mL) were added trimethylsilyldiazomethane (2 mol/L in hexane, 42.3 mL) and triethylamine (8.55 g) and the mixture was stirred at 60° C. The reaction mixture was added by water, then extracted with ethyl acetate. The obtained organic layer was dried and concentrated. To a solution of obtained residue in mixed solvent of tetrahydrofuran (60 mL) and ethanol (20 mL) were added argent benzoate (I) (0.77 g) and triethylamine (5.13 g) and the mixture was stirred at 70° C. The reaction mixture was concentrated, added by water, and extracted with ethyl acetate. The obtained organic layer was dried and concentrated. The obtained residue was purified by column chromatography on silica gel (hexane:ethyl acetate=1:2) to give the compound of the present invention (1.00 g) having the following physical data.

TLC: Rf 0.44 (ethyl acetate); NMR: δ 1.26 (t, J=7.1 Hz, 3H), 2.10 (s, 6H), 3.37 (s, 2H), 4.17 (q, J=7.1 Hz, 2H), 6.70 (d, J=9.5 Hz, 1H), 7.03 (dd, J=2.6, 0.8 Hz, 1H), 7.13-7.19 (m, 2H), 7.20-7.28 (m, 1H), 7.41 (dd, J=9.5, 2.6 Hz, 1H).

Example 55

[1-(2,6-dimethylphenyl)-6-oxo-1,6-dihydro-3-pyridinyl]acetic acid

By the same procedure as a reaction of Example 4, using the compound prepared in Example 54 instead of the compound prepared in Example 3, the compound of the present invention having the following physical data was obtained.

NMR: δ 2.08 (s, 6H), 3.40 (s, 2H), 6.78 (d, J=9.5 Hz, 1H), 7.04 (dd, J=2.6, 0.7 Hz, 1H), 7.12-7.19 (m, 2H), 7.20-7.28 (m, 1H), 7.45 (dd, J=9.5, 2.6 Hz, 1H).

Example 56

5-[2-(2,4-difluorophenyl)-2-oxoethyl]-1-(2,6-dimethylphenyl)-2(1H)-pyridinone

To a solution of the compound prepared in Example 55 (418 mg) in dichloromethane (8 mL) was added oxalyl chloride (309 mg). Stirring continually, N,N-dimethylformamide (0.1 mL) was dropped thereto. The reaction mixture was stirred for 5 minutes and concentrated. To a solution of obtained residue in dichloromethane (16 mL) were added 1,3-difluorobenzene (3 mL) and aluminum chloride (III) (649 mg) and the mixture was stirred at room temperature. The reaction mixture was added by sodium hydrogen carbonate solution, filtrated with Celite (proprietary name), and extracted with dichloromethane. The obtained organic layer was dried and concentrated. The obtained residue was purified by column chromatography on silica gel (hexane:ethyl acetate=1:3) to give the compound of the present invention (201 mg) having the following physical data.

TLC: Rf 0.55 (ethyl acetate); NMR: δ 2.08 (s, 6H), 4.02 (d, J=2.7 Hz, 2H), 6.71 (dd, J=9.4, 0.6 Hz, 1H), 6.84-6.95 (m, 1H), 6.95-7.06 (m, 2H), 7.13-7.20 (m, 2H), 7.20-7.29 (m, 1H), 7.35 (dd, J=9.4, 2.7 Hz, 1H), 7.89-8.03 (m, 1H).

Example 57

5-[4-(2,4-difluorophenyl)-2-(1-methyl-4-piperidinyl)-1,3-oxazol-5-yl]-1-(2,6-dimethylphenyl)-2(1H)-pyridinone

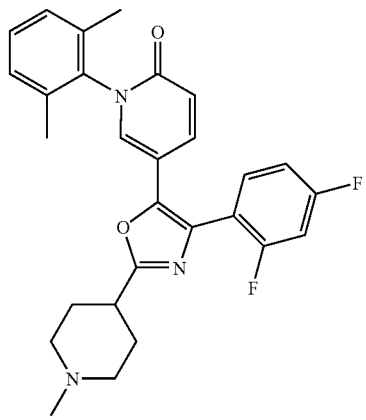

By the same procedure as a series of reactions of Example 7→Example 17→Example 18→Example 16, using the compound prepared in Example 56 instead of the compound prepared in Example 6, the compound of the present invention having the following physical data was obtained.

TLC: Rf 0.52 (dichloromethane:methanol:triethylamine=60:10:1); NMR: δ 1.92-2.33 (m, 12H), 2.38 (s, 3H), 2.76-3.10 (m, 3H), 6.69 (d, J=9.7 Hz, 1H), 6.80-6.91 (m, 1H), 6.93-7.03 (m, 1H), 7.13-7.21 (m, 2H), 7.21-7.31 (m, 2H), 7.37-7.48 (m, 1H), 7.53-7.66 (m, 1H).

Biological Examples

The whole operation was performed using the conventional method based on a fundamental biological technique. Also, as shown below, the measurement method used in the present invention is a method of which the measurement precision and/or the measurement sensitivity were enhanced and/or improved in order to evaluate the compounds of the present invention. Details of such experimental methods were shown below.

It was proven by the following Examples that the compounds of the present invention have inhibitory activity on p38α MAP kinase.

(1) Study on p38α Map Kinase Inhibitory Activity

Using activating transcription factor –2 (hereinafter abbreviated to ATF2) which is a substrate for p38α MAP kinase, the inhibitory action of the compounds of the present invention was investigated on the phosphorylation by a recombinant human p38α MAP kinase.

[Experimental Method]

A kinase buffer (25 mM Tris-HCl (pH 7.5), 5 mM β-glycerophosphate, 2 mM dithiothreitol, 0.1 mM $Na_3VO_4$, 10 mM $MgCl_2$) containing a recombinant human p38a MAP kinase was added to a 384-well plate (5 μL)(6.25 ng protein/well) for fluorescence measurement. After addition of a kinase buffer (5 μL) containing the compound of the present invention, the resulting mixture was incubated at room temperature for 20 minutes. A substrate mixture (5 μL) of biotinylated ATF2 of 5 μg/mL (Upstate Biotechnology #14-432), adenosine triphosphate (90 μmol/L)(Sigma #FL-AAS) and anti-phosphorylated ATF2 antibody (20-fold dilution)(Cell Signaling Technology #9221L) prepared separately was added thereto, and enzyme reaction was carried out at 30° C. for 30 minutes. After the reaction, Hepes buffer (5 µL) containing 0.25% BSA and 100 mM EDTA was added to stop the enzyme reaction. The amount of a complex of the phosphorylated ATF2 and anti-phosphorylated ATF2 antibody produced by the reaction was measured using an Alpha Screen™ Rabbit Detection kit (Packard #6760607).

The p38α MAP kinase inhibitory activity, which is the effect of the compound of the present invention, was calculated as an inhibition rate (%) according to the following equation:

$$\text{Inhibition rate (\%)} = \{(A_C - A_X)/(A_C - A_B)\} \times 100$$

wherein $A_B$ is a measured value without addition of the enzyme;

$A_C$ is a measured value with addition of the enzyme in the absence of a test compound; and $A_X$ is a measured value with addition of the enzyme in the presence of a test compound.

Inhibition rate of compounds with each concentration was calculated, and a value indicating 50% inhibition ($IC_{50}$) was determined from the inhibition curve.

As a result, it was confirmed that the compound of the present invention has p38 MAP kinase inhibitory activity. For example, the $IC_{50}$ values of the compounds described in Examples 10(2) was 1.4 nM.

Also, it was proven by the following Examples that the compounds of the present invention have inhibitory activity on TNF-α production.

(2) Inhibitory Activity Against TNF-α Production Using Human Cell Lines

Using THP-1 which is a human monocytic cell line, the inhibitory effect of the compound of the present invention against TNF-α production stimulated by lipopolysaccharide (LPS) was studied.

[Experimental Method]

Each 50 µL of lipopolysaccharide (LPS; Difco #3120-25-0) prepared to a concentration of 40 ng/mL using RPMI-1640 medium containing 10% fetal calf serum (hereinafter abbreviated to RPMI-1640) and RPMI-1640 containing the compound of the present invention was added to a 96-well plate for cell culture. One hundred µL of the cell suspension of THP-1 (Dainippon Pharmaceutical Co., Ltd, #06-202) prepared to a cell density of 2×10⁶ cells/mL using RPMI-1640 was added and cultured for 90 minutes at 37° C. in an incubator (5% $CO_2$, 95% air). After completion of the reaction, the culture medium supernatant was recovered and the amount of produced TNF-α was measured using an ELISA kit (Invitrogen, #850090192).

The inhibitory activity against TNF-α production, which is the effect of the compound of the present invention, was calculated as an inhibition rate (%) by the following equation:

$$\text{Inhibition rate (\%)} = \{(A_C - A_X)/(A_C - A_B)\} \times 100$$

wherein $A_B$ is a measured value without LPS induction;

$A_C$ is a measured value with LPS induction in the absence of a test compound; and $A_X$ is a measured value with LPS induction in the presence of a test compound.

Inhibition rate of compounds with each concentration was calculated, and a value indicating 50% inhibition ($IC_{50}$) was determined from the inhibition curve.

As a result, the compound of the present invention showed the inhibitory activity against TNF-α production. For example, the $IC_{50}$ values of the compounds described in Examples 10(2) was 1.4 nM.

(3) Rat Cytokine-production Model

The in vivo effect of the compound of the present invention was studied on TNF-α production induced by lipopolysaccharide (LPS) in rats.

[Experimental Method]

A vehicle containing the compound of the present invention was orally administered to male Lew mice (Charles River Japan, Inc.), and after 2 hours, lipopolysaccharide (LPS, 055: B5, Difco) was intravenously administered at the dose of 10 µg/kg (5 animals/group). Only a vehicle was orally administered to a control group (5 animals). Ninety minutes after the LPS treatment, heparinized blood collection was performed via the abdominal cava vein under anesthesia with ether, and blood plasma was obtained by centrifugation (12,000 rpm, 3 minutes, 4° C.). The obtained blood plasma sample was stored at −80° C. until it was used. TNF-α in the blood plasma was measured using an ELISA kit from Genzyme/Techne (#10516).

The inhibitory activity of the compound of the present invention against TNF-α production was calculated as an inhibition rate (%) according to the following equation:

$$\text{Inhibition rate (\%)} = \{(A_C - A_X)/A_C\} \times 100$$

wherein $A_C$ is a measured value in case where no test compound was administered under LPS induction, and $A_X$ is a measured value in case where a test compound was administered under LPS induction.

The results showed that the compound of the present invention has inhibitory activity against TNF-α production. For example, the compound of Example 10(2) of the present invention at the dose of 1 mg/kg showed an inhibition of 90% against in vivo TNF-α production induced by LPS stimulation. On the other hand, the compound disclosed in WO 01/030778 (4-[4-(4-fluorophenyl)-2-(1-methyl-4-piperidinyl)-1,3-thiazol-5-yl]-N-[(1S)-1-phenylethyl]-2-pyridinamine) showed an inhibition of 95% at the dose of 10 mg/kg in same experimental model. In view of this, by comparison in same experimental model, the TNF-α production inhibitory activity of the compound of Example 10(2) is stronger by a factor of 10 or more than that of the compound disclosed in WO 01/030778.

Formulation Examples

Formulation Example 1

5-[5-(2-chloro-4-fluorophenyl)-2-(1-methylpiperidin-4-yl)-1,3-thiazol-4-yl]-1-(2,6-dichlorophenyl)pyridine-2(1H)-one (5.0 kg), carboxymethylcellulose calcium (disintegrator) (0.2 kg), magnesium stearate (lubricant) (0.1 kg) and microcrystalline cellulose (4.7 kg) were admixed in a conventional manner, and tableted to obtain 100,000 tablets containing an active ingredient of 50 mg/tablet.

Formulation Example 2

5-[5-(2-chloro-4-fluorophenyl)-2-(1-methylpiperidin-4-yl)-1,3-thiazol-4-yl]-1-(2,6-dichlorophenyl)pyridine-2(1H)-one (2.0 kg), mannitol (20 kg), and distilled water (500 L) were admixed in a conventional manner, filtered with a dust filter, filled in ampoules (5 mL each), and heat-sterilized in an autoclave to obtain 100,000 ampoules containing an active ingredient of 20 mg/ampoule.

INDUSTRIAL APPLICABILITY

Since the compounds represented by general formula (I), or their salts, N-oxides or solvates, or prodrugs thereof have a low toxicity, they can be used as raw materials for drug medicines. Also, they are useful as an agent for the prevention and/or treatment of cytokine-mediated diseases such as rheumatoid arthritis and so forth, because they have p38 MAP kinase inhibitory activity.

The invention claimed is:
1. A compound represented by general formula (I):

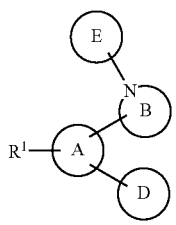

(I)

wherein ring A represents

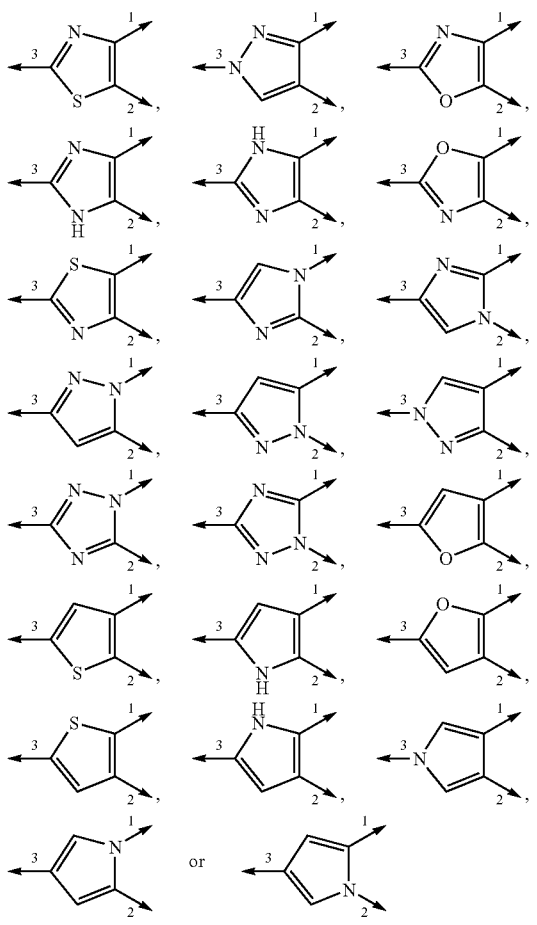

in which arrowhead 1 represents a bond with ring B; arrowhead 2 represents a bond with ring D; arrowhead 3 represents a bond with $R^1$; and the nitrogen atom represented by NH may have a substituent; and which may have a further substituent(s);
ring B represents

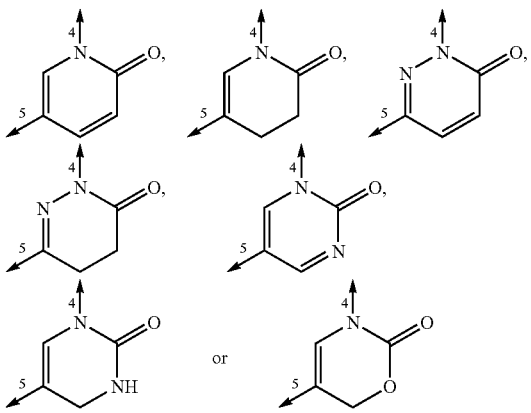

in which arrowhead 4 represents a bond with ring E; and arrowhead 5 represents a bond with ring A;
ring D represents an optionally substituted 5-to 10-membered carbon ring or an optionally substituted 5- to 10-membered hetero ring;
ring E represents an optionally substituted 5-to 10-membered carbon ring or an optionally substituted 5- to 10-membered hetero ring; and
$R^1$ represents a substituent which contains nitrogen atom(s) having basicity;
or a salt thereof.

2. The compound according to claim 1, wherein ring A is

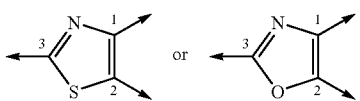

in which all symbols have the same meanings as described in claim 1.

3. The compound according to claim 1, wherein $R^1$ is an optionally substituted hetero ring which contains at least one nitrogen atom having basicity, an optionally substituted amino, an aliphatic hydrocarbon group substituted by an optionally substituted amino, or an aliphatic hydrocarbon group substituted by an optionally substituted hetero ring which contains at least one nitrogen atom having basicity.

4. The compound according to claim 1, wherein $R^1$ is an optionally substituted hetero ring which contains at least one nitrogen atom having basicity.

5. The compound according to claim 1, wherein $R^1$ is pyrrolidine, piperidine or perhydroazepine ring, which may have substituent(s).

6. The compound according to claim 1, wherein $R^1$ is

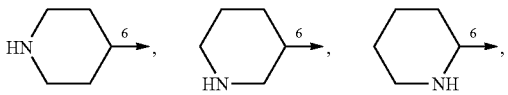

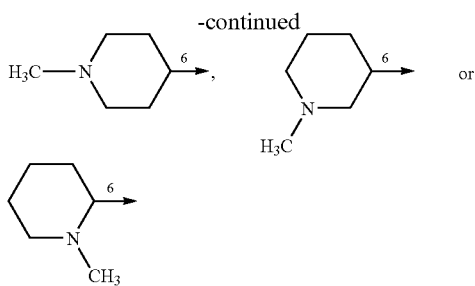

in which arrowhead 6 represents a bond with ring A.

7. The compound according to claim 1, represented by general formula (Ia), (Ib), (Ic), or (Id):

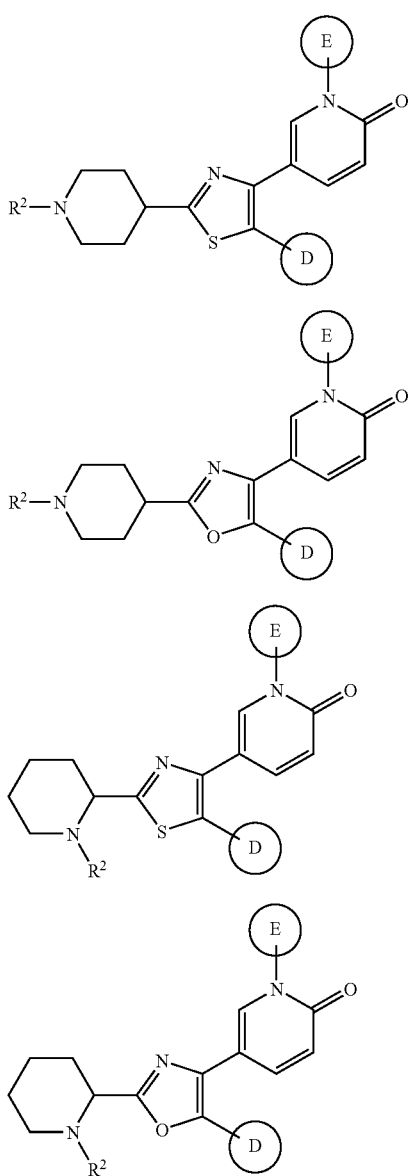

in which R² represents a hydrogen atom or a substituent; and all other symbols have the same meanings as described in claim 1.

8. The compound according to claim 1, wherein ring D is an optionally substituted benzene ring.

9. The compound according to claim 1, wherein ring E is an optionally substituted benzene ring.

10. The compound according to claim 8 or 9, wherein the substituent of ring D and/or ring E is C1-4 alkyl, C1-4 alkoxy and/or halogen atom.

11. The compound according to claim 1, selected from the group consisting of
    (1) 5-[5-(2-chloro-4-fluorophenyl)-2-piperidin-4-yl-1,3-thiazol-4-yl]-1-(2,6-dichlorophenyl)pyridin-2(1H)-one,
    (2) 5-[5-(2-chloro-4-fluorophenyl)-2-(1-ethylpiperidin-4-yl)-1,3-thiazol-4-yl]-1-(2,6-dichlorophenyl)pyridin-2(1H)-one,
    (3) 5-[5-(2-chloro-4-fluorophenyl)-2-(1-isopropylpiperidin-4-yl)-1,3-thiazol-4-yl]-1-(2,6-dichlorophenyl)pyridin-2(1H)-one,
    (4) 5-[5-(2-chloro-4-fluorophenyl)-2-(1-methylpiperidin-4-yl)-1,3-thiazol-4-yl]-1-(2,6-dichlorophenyl)pyridin-2(1H)-one,
    (5) 5-(5-(2-chloro-4-fluorophenyl)-2-{1-[2-(dimethylamino)ethyl]piperidin-4-yl}-1,3-thiazol-4-yl)-1-(2,6-dichlorophenyl)pyridin-2(1H)-one,
    (6) 5-[5-(2,4-difluorophenyl)-2-(1-methylpiperidin-4-yl)-1,3-thiazol-4-yl]-1-(2,6-dimethylphenyl)pyridin-2(1H)-one,
    (7) 5-[5-(2,4-difluorophenyl)-2-(1-methylpiperidin-4-yl)-1,3-oxazol-4-yl]-1-(2,6-dimethylphenyl)pyridin-2(1H)-one,
    (8) 1-(2,6-difluorophenyl)-5-[5-(2,4-difluorophenyl)-2-(1-methylpiperidin-4-yl)-1,3-thiazol-4-yl]pyridin-2(1H)-one,
    (9) 5-[5-(2,4-difluorophenyl)-2-(1-methylpiperidin-4-yl)-1,3-oxazol-4-yl]-1-(4-fluoro-2,6-dimethylphenyl)pyridin-2(1H)-one,
    (10) 1-(2,6-difluorophenyl)-5-[5-(2,4-difluorophenyl)-2-(1-methylpiperidin-4-yl)-1,3-oxazol-4-yl]pyridin-2(1H)-one,
    (11) 5-[5-(2,4-difluorophenyl)-2-(1-methylpiperidin-4-yl)-1,3-thiazol-4-yl]-1-(4-methoxy-2,6-dimethylphenyl)pyridin-2(1H)-one,
    (12) 1-(4-chloro-2,6-dimethylphenyl)-5-[5-(2,4-difluorophenyl)-2-(1-methylpiperidin-4-yl)-1,3-oxazol-4-yl]pyridin-2(1H)-one,
    (13) 1-(2-chloro-6-methylphenyl)-5-[5-(2,4-difluorophenyl)-2-(1-methylpiperidin-4-yl)-1,3-oxazol-4-yl]pyridin-2(1H)-one,
    (14) 5-[5-(2,4-difluorophenyl)-2-(1-methylpiperidin-4-yl)-1,3-oxazol-4-yl]-1-(2-fluorophenyl)pyridin-2(1H)-one,
    (15) 5-[5-(2,4-difluorophenyl)-2-(1-methylpiperidin-4-yl)-1,3-oxazol-4-yl]-1-(2,4,6-trifluorophenyl)pyridin-2(1H)-one,
    (16) 5-[5-(2,4-difluorophenyl)-2-(1-methylpiperidin-4-yl)-1,3-oxazol-4-yl]-1-(2,3,6-trifluorophenyl)pyridin-2(1H)-one,
    (17) 5-[5-(2,4-difluorophenyl)-2-(1-methylpiperidin-4-yl)-1,3-oxazol-4-yl]-1-(2-fluoro-6-methylphenyl)pyridin-2(1H)-one,
    (18) 1-(2,6-difluorophenyl)-5-[5-(4-fluorophenyl)-2-(1-methylpiperidin-4-yl)-1,3-oxazol-4-yl]pyridin-2(1H)-one,

(19) 5-[5-(2,4-difluorophenyl)-2-(1-methylpiperidin-4-yl)-1,3-oxazol-4-yl]-1-(4-methoxy-2,6-dimethylphenyl)pyridin-2(1H)-one,

(20) 1-(2,6-dimethylphenyl)-5-[5-(2-fluoro-4-methylphenyl)-2-(1-methylpiperidin-4-yl)-1,3-oxazol-4-yl]pyridin-2(1H)-one,

(21) 5-{5-(2,4-difluorophenyl)-2-[(3R)-piperidin-3-yl]-1,3-oxazol-4-yl}-1-(2,6-dimethylphenyl)pyridin-2(1H)-one,

(22) 5-{5-(2,4-difluorophenyl)-2-[(3R)-1-methylpiperidin-3-yl]-1,3-oxazol-4-yl}-1-(2,6-dimethylphenyl)pyridin-2(1H)-one,

(23) 5-{5-(2,4-difluorophenyl)-2-[(3S)-piperidin-3-yl]-1,3-oxazol-4-yl}-1-(2,6-dimethylphenyl)pyridin-2(1H)-one,

(24) 5-{5-(2,4-difluorophenyl)-2-[(3S)-1-methylpiperidin-3-yl]-1,3-oxazol-4-yl}-1-(2,6-dimethylphenyl)pyridin-2(1H)-one,

(25) 1-(2,6-difluorophenyl)-5-{5-(2,4-difluorophenyl)-2-[(2S)-1-methyl-2-piperidinyl]-1,3-oxazol-4-yl}-2(1H)-pyridinone, and

(26) 1-(2,6-difluorophenyl)-5-{5-(2,4-difluorophenyl)-2-[(2R)-1-methyl-2-piperidinyl]-1,3-oxazol-4-yl}-2(1H)-pyridinone.

12. A pharmaceutical composition comprising a compound represented by general formula (I)

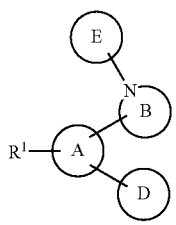

(I)

wherein ring A represents

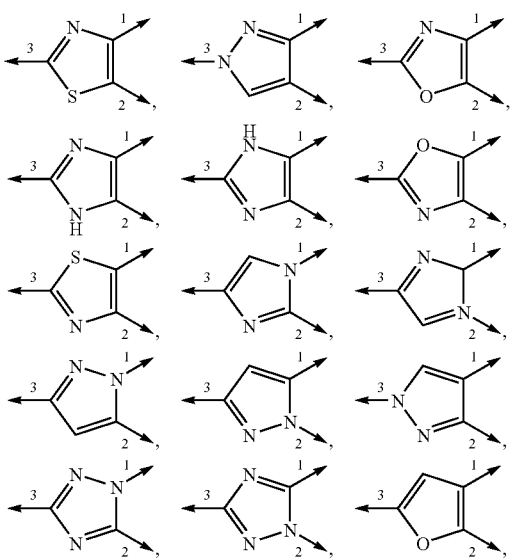

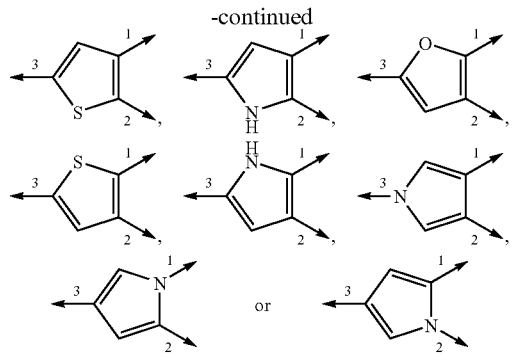

in which arrowhead 1 represents a bond with ring B; arrowhead 2 represents a bond with ring D; arrowhead 3 represents a bond with $R^1$, and the nitrogen atom represented by NH may have a substituent; and which may have a further substituent(s);

ring B represents

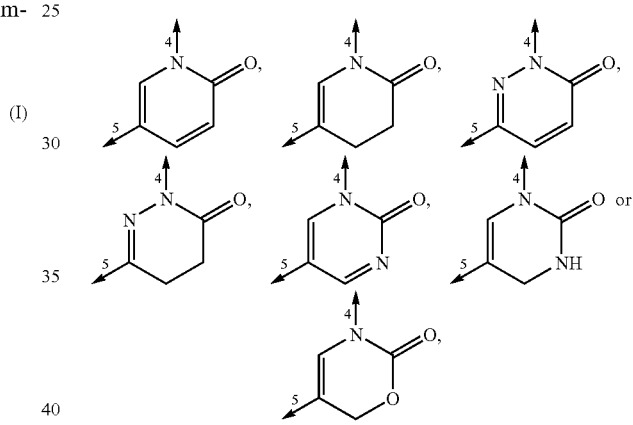

in which arrowhead 4 represents a bond with ring E; and arrowhead 5 represents a bond with ring A;

ring D represents an optionally substituted 5- to 10-membered carbon ring or an optionally substituted 5- to 10-membered hetero ring;

ring E represents an optionally substituted 5- to 10-membered carbon ring or an optionally substituted 5- to 10-membered hetero ring; and $R^1$ represents a substituent which contains nitrogen atom(s) having basicity;

or a salt thereof, and a pharmaceutically acceptable carrier.

13. The composition according to claim 12, wherein the compound represented by formula (I) is 5-[5-(2-chloro-4-fluorophenyl)-2-(1-methylpiperidin-4-yl)-1,3-thiazol-4-yl]-1-(2,6-dichlorophenyl)pyridine-2-(1H)-one, or, 1-(2,6-difluorophenyl)-5-[5-(2,4-difluorphenyl)-2-(1-methylpiperidin-4-yl)-1,3-oxazol-4-yl]pyridine-2-(1H)-one, which is an agent for treatment of rheumatoid athritis.

* * * * *